United States Patent [19]

Janssens et al.

[11] Patent Number: 4,839,374

[45] Date of Patent: Jun. 13, 1989

[54] 4-((BICYCLIC HETEROCYCLYL)-METHYL AND -HETERO)-PIPERIDINES

[75] Inventors: Frans E. Janssens, Bonheiden; Ludo E. J. Kennis, Turnhout; Jozef F. Hens, Nijlen; Joseph L. G. Torremans, Beerse; Gaston S. M. Diels, Ravels, all of Belgium

[73] Assignee: Janssen Pharmaceutica, N.V., Beerse, Belgium

[21] Appl. No.: 94,987

[22] Filed: Sep. 10, 1987

Related U.S. Application Data

[60] Division of Ser. No. 747,754, Jun. 24, 1985, Pat. No. 4,695,575, which is a continuation-in-part of Ser. No. 671,135, Nov. 13, 1984, abandoned, which is a continuation-in-part of Ser. No. 569,369, Jan. 9, 1984, abandoned.

[51] Int. Cl.$^4$ ............................................. A61K 31/435

[52] U.S. Cl. ................................... 514/394; 514/258; 514/299; 514/395

[58] Field of Search ............... 514/299, 394, 395, 397, 514/398, 399, 300

[56] References Cited

U.S. PATENT DOCUMENTS

| | | | |
|---|---|---|---|
| 4,219,559 | 8/1980 | Janssens | 546/118 |
| 4,477,276 | 10/1984 | Willms | 546/118 |
| 4,556,660 | 12/1985 | Janssens | 546/118 |
| 4,588,722 | 5/1986 | Janssens | 514/228 |

*Primary Examiner*—Christopher Henderson

[57] ABSTRACT

4-[Bicyclic heterocyclyl)methyl and -hetero]-piperidines having antihistaminic and serotonin-antagonistic properties which compounds are useful agents in the treatment of allergic diseases.

6 Claims, No Drawings

4-((BICYCLIC HETEROCYCLYL)-METHYL AND -HETERO)-PIPERIDINES

CROSS-REFERENCE TO RELATED APPLICATIONS

This is a division of application Ser. No. 747,754, filed June 24, 1985, now U.S. Pat. No. 4,695,575, which is a continuation-in-part of our co-pending application Ser. No. 671,135, filed Nov. 13, 1984., now abandoned, which in turn is a continuation-in-part of our co-pending application Ser. No. 569,369, filed Jan. 9, 1984, now abandoned.

BACKGROUND OF THE INVENTION

In U.S. Pat. No. 4,219,559 there are described a number of N-heterocyclyl-4-piperidinamines having the formula

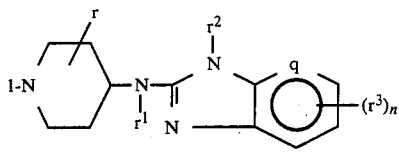

which compounds are useful as antihistaminic agents.

The compounds of the present invention differ from the prior art compounds essentially by the nature of the 4-piperidinyl substituent which is invariably a bicyclic heterocyclyl-methyl or -hetero group and by the fact that the compounds of the present invention are not only potent histamine-antagonists but also potent serotoninantagonists.

DESCRIPTION OF THE PREFERRED EMBODIMENTS

This invention is concerned with novel 4-[bicyclic heterocyclylmethyl and -hetero]-piperidines which may structurally be represented by the formula

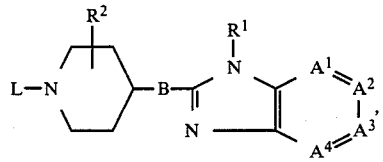

the pharmaceutically acceptable acid addition salts and the possible stereochemically isomeric forms thereof, wherein:

$A^1=A^2-A^3=A^4$ is a bivalent radical having the formula

| —CH=CH—CH=CH— | (a-1), |
| —N=CH—CH=CH— | (a-2), |
| —CH=N—CH=CH— | (a-3), |
| —CH=CH—N=CH— | (a-4), or |
| —CH=CH—CH=N— | (a-5), | wherein one or two hydrogen atoms in said radicals (a-1)–(a-5) may, each independently from each other, be replaced by halo, lower alkyl, lower alkyloxy, trifluoromethyl or hydroxy;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen and lower alkyl;

B is $CH_2$, O, S, SO or $SO_2$;

L is a member selected from the group consisting of a radical of formula

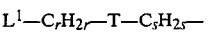

$$L^1-C_rH_{2r}-T-C_sH_{2s}- \qquad \text{(b-1); and}$$

a radical of formula

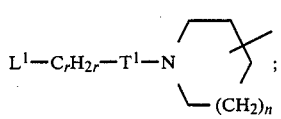

(b-2)

wherein one or two hydrogen atoms in the bivalent radical $-C_sH_{2s}-$ may, each independently from each other, be replaced by halo, hydroxy, mercapto, isothiocyanato, isocyanato, lower alkyloxy, lower alkylthio, $Ar^1$, $Ar^1O-$, $Ar^1S-$, $Ar^1SO_2-$, or $NHR^3R^5$; and n is 0 or the integer 1 or 2;

r and s are, independently from each other, 0 or an integer of from 1 to 6 inclusive;

T is

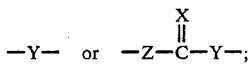

$T^1$ is

or a direct bond;

said Y being O, S, $NR^3$ or a direct bond;

X being O, S, $CH-NO_2$ or $NR^4$;

Z being O, S, $NR^5$ or a direct bond; and said $R^3$ being hydrogen, lower alkyl, ($Ar^2$)lower alkyl, 2-lower alkyloxy-1,2-dioxoethyl or a radical of formula $-C(=X)-R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-amino, $Ar^2$-lower alkylamino or $Ar^2$-lower alkyl(lower alkyl)amino;

said $R^4$ being hydrogen, lower alkyl, cyano, nitro, $Ar^2$-sulfonyl, lower alkylsulfonyl, lower alkylcarbonyl or $Ar^2$-carbonyl; and said $R^5$ being hydrogen or lower alkyl;

wherein $L^1$ is a member selected from the group consisting of hydrogen; halo; hydroxy; lower alkyloxy; lower alkylthio; cyano; mercapto; isocyanato; isothiocyanato; $Ar^1$; $Ar^1$-carbonyl; $Ar^1$-sulfonyl; lower alkylsulfonyl; cycloalkyl being optionally substituted with up to two substituents each independently selected from the group consisting of lower alkyl, cyano and $Ar^2$; [10,11-dihydro-5H-dibenzo[a,d]cyclohepten-5-ylidene]methyl; Het; and furan substituted with substituted lower alkyl; said substituted lower alkyl being lower alkyl substituted with a member selected from the group consisting of hydroxy, mercapto, lower alkyloxy, lower alkylthio, aminolower alkylthio, $Ar^2$-oxy and a radical of formula

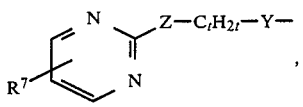
(c)

wherein: t is 0 or an integer of from 1 to 6 inclusive; and
R⁷ is hydrogen or lower alkyl;
provided that: when in said radical of formula (c) t is 0, then Z or Y is a direct bond; and
where r is 0, $L^1$ may also be lower alkenyl, $Ar^1$-lower alkenyl or lower alkyl substituted with two lower alkyloxy radicals; and
where r is 0 and T is $NR^3$, or T is —N($R^5$)—C(=X)—Y or $T^1$ is —N($R^5$)—C(=X)—, $L^1$ may also be amino, lower alkylamino or $Ar^1$-amino; and
where r is 0, and T is —N($R^5$)—C(=X)—Y or $T^1$ is —N($R^5$)—C(=X)—, $L^1$ may also be nitro;
said Het being an optionally substituted five- or six-membered heterocyclic ring, being optionally condensed with an optionally substituted five- or six-membered carbocyclic or heterocyclic ring;
provided that:
(i) when L is a radical of formula (b-1) wherein $L^1$ is hydrogen and wherein T is —Z—C(=X)—Y— wherein Y is other then a direct bond and Z and X are each independently O or S, then r is not 0; or when L is a radical of formula (b-2) wherein $L^1$ is hydrogen and wherein $T^1$ is —Z—C(=X)— wherein Z and X are each independently O or S, then r is not 0;
(ii) when L is a radical of formula (b-1) wherein $L^1$ is halo, hydroxy, lower alkyloxy, mercapto, lower alkylthio, isocyanato, isothiocyanato or Het connected to $C_rH_{2r}$ on a nitrogen atom, and wherein r is 0, then T is a direct bond or a radical —C(=X)—Y—; or when L is a radical of formula (b-2) wherein $L^1$ is halo, hydroxy, lower alkyloxy, mercapto, lower alkylthio, isocyanato, isothiocyanato or Het connected to $C_rH_{2r}$ on a nitrogen atom, and wherein r is 0, then $T^1$ is a radical —C(=X)—;
(iii) when L is a radical of formula (b-1) wherein T is Y, said Y being other than a direct bond, or wherein T is —Z—C(=X)—Y—, wherein Y is other than a direct bond, then s is not 0;
wherein $Ar^1$ is a member selected from the group consisting of phenyl, substituted phenyl, naphthalenyl, thienyl, halothienyl, lower alkylthienyl, pyridinyl, mono- and di(lower alkyloxy)pyridinyl, pyrrolyl, lower alkylpyrrolyl, furanyl, furanyl substituted with lower alkyl, pyrazinyl, thiazolyl, imidazolyl, lower alkylimidazolyl; said substituted phenyl, being phenyl substituted with up to 3 substituents each independently selected from the group consisting of halo, hydroxy, nitro, cyano, trifluoromethyl, lower alkyl, lower alkyloxy, lower alkylthio, mercapto, amino, mono- and di(lower alkyl)amino, lower alkylsulfonyl, lower alkylsulfonyllower alkyl, phenyllower alkylsulfonyl, phenylsulfonyllower alkyl, a radical of formula $R^8$—$C_pH_{2p}$—Y—, a radical of formula $R^9$—Z—C(=X)—Y—, and a radical of formula $R^{10}SO_2Y$—; wherein p is an integer of from 1 to 6 inclusive and $R^8$ is a member selected from the group consisting of amino, cyano, phenyl aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl, 1-pyrrolidinylcarbonyl, and lower alkenyl; wherein $R^9$ is member selected from the group consisting of hydrogen, lower alkyl and $Ar^2$; provided that, when $R^9$ is hydrogen and Y is other than a direct bond, then Z is not O or S; and wherein $R^{10}$ is lower alkyl or $Ar^2$;

wherein $Ar^2$ is a member selected from the group consisting of phenyl, substituted phenyl, thienyl and furanyl, said substituted phenyl being phenyl optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

As used in the foregoing definitions the term halo is generic to fluoro, chloro, bromo and iodo; the term "lower alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "alkyl" is meant to include lower alkyl radicals, as defined hereinabove, and the higher homologs thereof having from 7 to 10 carbon atoms; the term "lower alkenyl" is meant to include straigth and branch chained hydrocarbons radicals having from 2 to 6 carbon atoms, such as, for example, 2-propenyl, 2-butenyl, 3-butenyl, 2-pentenyl and the like; the term "cycloalkyl" is generic to cyclopropyl, cyclobutyl, cyclopentyl and cyclohexyl; and "lower alkanediyl" is meant to include bivalent straight or branch chained alkanediyl radicals having from 1 to 6 carbon atoms.

Preferred compounds within the invention are those wherein Het is a five- or six-membered heterocyclic ring containing a number of heteroatoms which varies of from 1 to 4, said heteroatoms being selected from the group consisting of oxygen, sulfur and nitrogen, provided that no more than two oxygens or sulfurs are present, said five or six-membered ring being optionally condensed with a five- or six-membered carbocyclic or heterocyclic ring also containing a number of heteroatoms which varies from 1 to 4, the latter heteroatoms being selected from the group consisting of oxygen, sulfur and nitrogen, provided that no more than 2 oxygens or sulfurs are present, and wherein said Het being a bicyclic ring system may optionally be substituted with up to 6 substituents, or said Het being a monocyclic ring system may optionally be substituted with up to 3 substituents, said substituents of Het being selected from te group consisting of a bivalent radical of formula =X, said =X independently having the same meaning of the previously defined X; halo; isocyanato; isothiocyanato; nitro, cyano, trifluoromethyl; a radical of formula R—Y—, wherein R is hydrogen, $Ar^1$ or lower alkyl being optionally substituted with $Ar^1$, lower alkyloxy, $Ar^1O$, hydroxy, lower alkyloxycarbonyl and Y independently has the same meaning of the previously defined Y; and a radical R—Z—C(=X)—Y—, wherein R is as defined hereinabove and Z, X and Y independently have the same meanings of the previously defined Z, X and Y; provided that (i) when in the radical R—Y—R is hydrogen, then Y is other than a direct bond, or (ii) when in the radical R—Z—C(=X)—Y—R is hydrogen and Y is $NR^3$, O or S, then Z is other than O or S.

Particularly preferred compounds within the invention are those wherein Het is a member selected from the group consisting of (i) pyridinyl which is optionally substituted with one or two substituents each independently selected from the group consisting of halo, amino, mono- and dilower alkyl amino, $Ar^2$ lower alkylamino, nitro, cyano, aminocarbonyl, lower alkyl, lower alkyloxy, lower alkylthio, lower alkyloxycarbonyl, hydroxy, lower alkylcarbonyloxy, $Ar^2$-lower alkyl and carboxyl;

pyridinyloxide optionally substituted with nitro;

quinolinyl which is optionally substituted with lower alkyl;

pyrimidinyl which is optionally substituted with one or two substituents are independently selected from the group consisting of halo, amino, hydroxy, lower alkyl, lower alkyloxy, lower alkylthio and $(Ar^2)$-lower alkyl;

quinazolinyl which is optionally substituted with hydroxy or lower alkyl;

pyridazinyl which is optionally substituted with lower alkyl or halo;

quinoxalinyl which is optionally substituted with lower alkyl;

pyrazinyl which is optionally substituted with halo, amino or lower alkyl;

phthalazinyl which is optionally substituted with halo;

morfolinyl;

thiomorfolinyl;

piperidinyl;

2,3-dihydro-3-oxo-4H-benzoxazinyl and 2,3-dihydro-1,4-benzodioxinyl, both being optionally substituted with lower alkyl or halo;

dioxanyl being optionally substituted with lower alkyl; 2-oxo-2H-1-benzopyranyl and 4-oxo-4H-1-benzopyranyl both being optionally substituted with lower alkyl;

1,4-dihydro-2,4-dioxo-3(2H)-pyrimidinyl being optionally substituted with lower alkyl; and 4-oxo-2(1H)-pyrimidinyl;

(ii) 5,6-dihydro-4H-1,3-thiazin-2-yl, thiazolyl, 4,5-dihydrothiazolyl, oxazolyl, imidazolyl, tetrazolyl, 1,3,4-thiadiazolyl, benzimidazolyl, benzothiazolyl, benzoxazolyl, 4,5-dihydro-5-oxo-1H-tetrazolyl, 2-oxo-3-oxazolidinyl and indolyl whereby each of the Het-radicals of group (ii) may optionally be substituted where possible with up to two substituents selected from the group consisting of lower alkyl, $Ar^1$, $Ar^1$-lower alkyl, benzimidazolyllower alkyl, amino, (aminoiminomethyl)amino, mono- and di(lower alkyl)amino, $Ar^1$-amino, nitro, lower alkyloxycarbonyl and pyrimidinyl;

(iii) a radical of formula

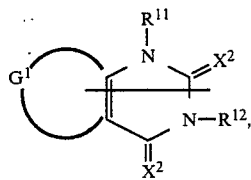  (e-1)

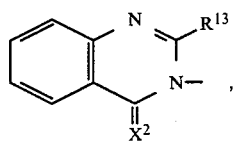  (e-2)

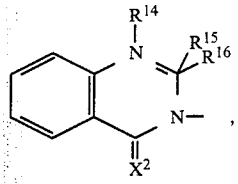  (e-3)

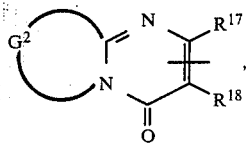  (e-4)

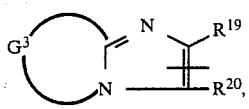  (e-5)

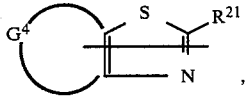  (e-6)

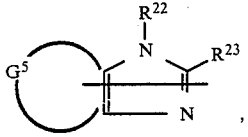  (e-7)

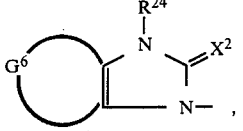  (e-8)

and

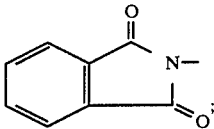  (e-9)

wherein each $X^2$ is independently O or S;

$R^{11}$, $R^{12}$, $R^{14}$, $R^{22}$ and $R^{24}$ are each independently hydrogen, lower alkyl, $Ar^2$-lower alkyl, hydroxylower alkyl or lower alkyloxycarbonyl;

$R^{13}$, $R^{16}$, $R^{17}$, $R^{18}$, $R^{19}$, $R^{20}$, $R^{21}$ and $R^{23}$ are each independently hydrogen, lower alkyl, hydroxy, mercapto, lower alkyloxy, lower alkylthio, halo and (lower alkyloxycarbonyl)lower alkyl;

$G^1$ is —CH=CH—CH=CH—, —S—CH=CH— or —N=CH—NH—;

$G^2$ is —CH=CH—CH=CH—, —S—(CH$_2$)$_2$, —S—(CH$_2$)$_3$, —(CH$_2$)$_4$ or S—CH=CH—;

$G^3$ is —CH=CH—CH=CH—, —CH$_2$—NH—(CH$_2$)$_2$—, —S—CH=CH—, —N=CH—CH=CH—, —CH=N—CH=CH—, —CH=CH—N=CH—, —CH=CH—CH=N—, —N=CH—N=CH— or —CH=N—CH=N—;

$G^4$ is —CH$_2$—NH—(CH$_2$)$_2$—, —N=CH—CH=CH—, —CH=N—CH=CH—, —CH=CH—N=CH—, —CH=CH—CH=N—, —N=CH—N=CH— or —CH=N—CH=N—;

$G^5$ is —N=CH—CH=CH—, —CH=N—CH=CH—, —CH=CH—N=CH—, —CH=CH—CH=N—, —N=CH—N=CH— or —CH=N—CH=N—;

$G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in said radicals $G^1$, $G^2$, $G^3$, $G^4$, $G^5$ or $G^6$ or in the benzene part of the radicals of formula (e-2), (e-3) or (e-9) may be replaced by lower alkyl, lower alkylthio, lower alkyloxy or halo where said hydrogen atom is bonded on a carbon atom, or by lower alkyl, lower alkyloxycarbonyl, $Ar^2$-lower alkyl, where said hydrogen is bonded on a nitrogen atom.

It is clear that $R^{11}$, $R^{12}$, $R^{17}$, $R^{18}$, $R^{19}$, $R^{20}$, $R^{21}$, $R^{22}$ or $R^{23}$ is absent where the radical of formula (e-1), respectively (e-4), (e-5), (e-6) or (e-7) is connected to $C_sH_{2s}$ on the atom bearing $R^{11}$, $R^{12}$, $R^{17}$, $R^{18}$, $R^{19}$, $R^{20}$, $R^{21}$, $R^{22}$ or $R^{23}$.

More particularly preferred compounds within the invention are those wherein Het is as described hereinabove for the particularly preferred compounds, r is 0 and $L^1$ is hydrogen, hydroxy, lower alkyloxy, lower alkylthio, mercapto, Het, $Ar^1$, cyanato or isothiocyanato.

Especially preferred compounds within the invention are those wherein Het is as described hereinabove for the more particularly preferred compound, r is 0 and $L^1$ is as described hereinabove for the preferred compounds and wherein $R^1$ is lower alkyl substituted with one $Ar^1$ radical.

More especially preferred compounds within the invention are those wherein L is a radical of formula (b-1), wherein r is 0 and $L^1$ is as described hereinabove for the preferred compounds and wherein $R^1$ is lower alkyl substituted with one $Ar^1$ radical.

The most preferred compounds within the invention are selected from the group consisting of 1-[(4-fluorophenyl)methyl]-2-[[1-[2-(4-hydroxyphenyl)ethyl]-4-piperidinyl]methyl]-1H-benzimidazol-6-ol and the pharmaceutically acceptable acid-addition salts thereof.

It is evident that in the compounds of formula (I) wherein $L^1$ is Het, said Het may be unsaturated or partly or completely saturated.

The compounds of formula (I) wherein Het is a heterocycle which is substituted with a hydroxy, mercapto or amino radical may contain in their structure a keto-enol tautomeric system or a vinylog system thereof, and consequently these compounds may be present in their keto form as well as their enol form.

The compounds of formula (I) can generally be prepared by reacting a piperidine of formula (II) with a diamine of formula (III).

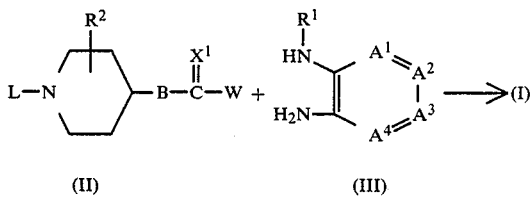

In (II) $X^1$ is O, S or NH.

W as used in the foregoing and following reaction schemes is an appropriate leaving group such as, for example, halo, e.g. chloro, bromo or iodo, a sulfonyloxy group, e.g. methylsulfonyloxy or 4-methylphenylsulfonyloxy, and where W is connected to a —C(=X)—, —C(=X$^1$)— or —C(=X$^2$)— radical it may also be lower alkyloxy, lower alkylthio, $Ar^2$—O—, or $Ar^2$—S—.

The piperidine of formula (II) may in situ be generated, for example, by converting a piperidine which is substituted in its 4-position with a —B—C(=X$^1$)—OH radical into a piperidine of formula (II) by reacting the former piperidine with thionyl chloride, phosphor trichloride, polyphosphoric acid, phosphoroxychloride and the like. The reaction of (II) with (III) may be conducted in a suitable solvent such as, for example, a hydrocarbon, e.g., benzene, hexane, an ether, e.g., 1,1'-oxybisethane, tetrahydrofuran, a ketone, e.g., propanone, an alcohol, e.g., methanol, ethanol, 2-propanol, 1-butanol, a halogenated hydrocarbon, e.g., trichloromethane, dichloromethane, an acid, e.g., acetic acid, propanoic acid, N,N-dimethylformamide, N,N-dimethylacetamide and the like, and mixtures of such solvents. Depending upon the solvent and nature of W it may be appropriate to add an appropriate base and/or an iodide salt, preferably an alkali metal iodide, to the reaction mixture. Elevated temperatures may enhance the reaction rate.

The compounds of formula (I) can also be prepared by reacting an intermediate of formula (V) with a piperidine of formula (IV) wherein $E^1$ and $E^2$ are selected so that during the reaction a radical —B— is formed.

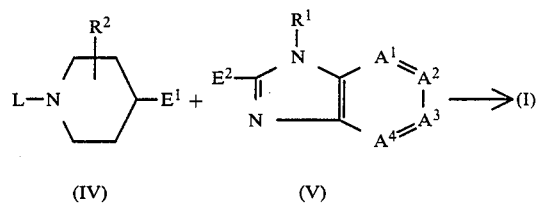

For example, the compounds of formula (I) can be prepared by reacting a piperidine of formula (IV) wherein $E^1$ is a radical of formula —B—M with an intermediate of formula (V) wherein $E^2$ is a radical of formula —W.

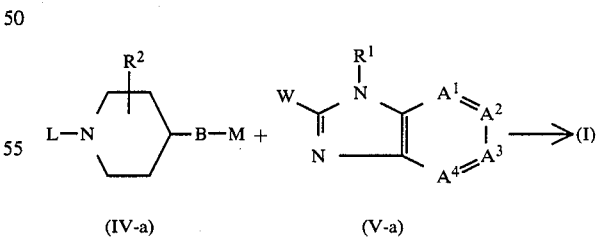

In (IV-a) M is, depending upon the nature of B, hydrogen or an appropriate alkalimetal or earth alkaline metal and in (V-a) W has the previously described meaning. Additionally, the compounds of formula (I) can also be prepared by reacting a piperidine of formula (IV) wherein $E^1$ is W with an intermediate of formula (V) wherein $E^2$ is a radical of formula —B—M, said W and M having the previously described meanings.

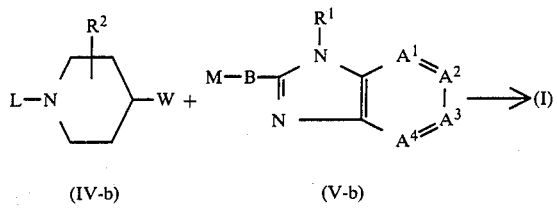

(IV-b)    (V-b)

More particularly, the compounds of formula (I) wherein B is —CH$_2$— can also be prepared by reacting a piperidine of formula (IV) wherein E$^1$ represents a radical of formula —CH$_2$—W, (IV-c), with an intermediate of formula (V) wherein E$^2$ represents M, (V-c) or alternatively, by reacting a piperidine of formula IV, wherein E$^1$ is a radical of formula —M, (IV-d), with an intermediate of formula (V) wherein E$^2$ is a radical of formula —CH$_2$—W, (V-d).

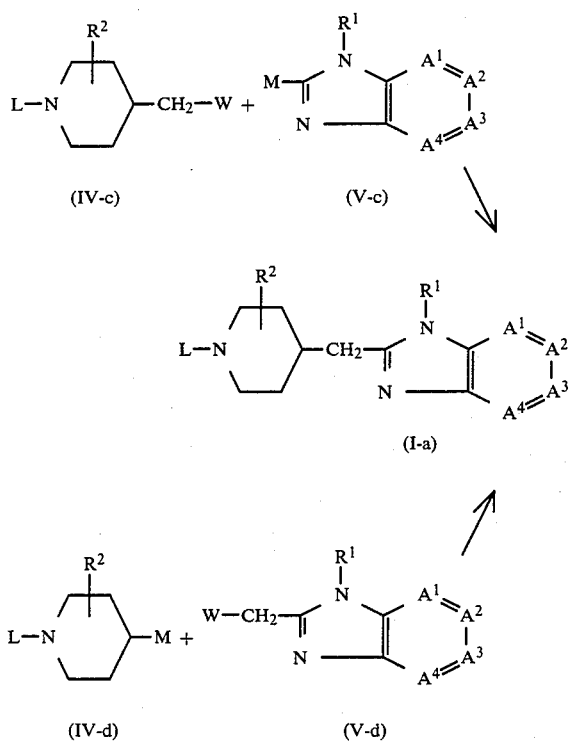

The reaction of (IV) with (V) may conveniently conducted in an appropriate solvent such as for example, an aromatic hydrocarbon, e.g., benzene, methylbenzene; an ether, e.g. 1,4-dioxane, 1,1'-oxybisethane, tetrahydrofuran and the like; a halogenated hydrocarbon, e.g. trichloromethane and the like; N,N-dimethylformamide (DMF); N,N-dimethylacetamide (DMA); and where M is hydrogen, said solvent may also be a lower alkanol, e.g., methanol, ethanol, 1-butanol and the like; a ketone, e.g., 2-propanone, 4-methyl-2-pentanone and the like. In some circumstances, the addition of an appropriate base such as, for example, an alkali metal carbonate or hydrogen carbonate, sodium hydride or an organic base such as, for example, N,N-diethylethanamine or N-(1-methylethyl)-2-propanamine and/or the addition of an iodide salt, preferably an alkali metal iodide, may be appropriate. Somewhat elevated temperatures may enhance the rate of the reaction.

The compounds of formula (I) can also be derived from a 1,4-dihydropyridine derivative of formula (VI) following art-known reducing procedures.

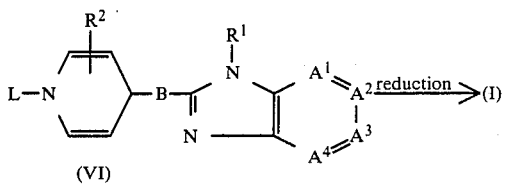

Suitable reducing procedures are, for example, a catalytic hydrogenation in a suitable solvent, e.g. methanol, ethanol and the like, in the presence of a suitable catalyst, e.g., platinum-on-charcoal, palladium-on-charcoal and the like catalysts.

The compounds of formula (I) can also be converted into each other. A number of such reactions will be described hereinafter in more detail.

In order to simplify the structural representations of the compounds of formula (I) and of certain precursors and intermediates thereof the

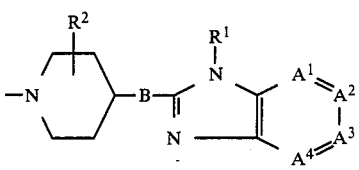

-radical will hereafter be represented by the symbol D.

The compounds of formula (I) wherein L is L$^2$, said compounds being represented by the formula (I-b) can be prepared by alkylating an intermediate of formula (VII) with a compound of formula (I) wherein L is Q$^2$, said compound being represented by the formula (I-c).

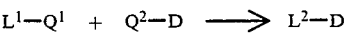

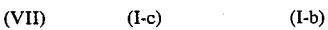

L$^2$ as defined hereinabove is a radical of formula (b-1) other then hydrogen, said radical being represented by the formula (b-1-a), or a radical of formula (b-2).

In (VII) and (I-c), Q$^1$ and Q$^2$ are selected so that a bivalent radical of formula (b-1-a) or (b-2) is formed during the alkylation reaction, said (b-1-a) and (b-2) having the previously described meaning.

For example, the compounds of formula (I-b) can be prepared by N-alkylating a piperidine of formula (I-c) wherein Q$^2$ is hydrogen, said piperidine being represented by the formula (I-c-1), with a reagent of formula (VII-a)

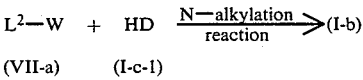

(VII-a)    (I-c-1)

Additionally, the compounds of formula (I-b), wherein L$^2$ is a radical of formula (b-1-a), wherein T is T$^2$, said T$^2$ being O, S, NR$^3$ or —Z$^1$—C(=X)—Y—, said Z$^1$ being O, S or NR$^5$, or a radical of formula (b-2) wherein T$^1$ is T$^3$, said T$^3$ being —Z$^1$—C(=X)— or a direct bond, said compounds being represented by the formulae (I-b-1-a), respectively (I-b-1-b), can be prepared by alkylating a piperidine of formula (I-c-2) with a reagent of formula (VII-b).

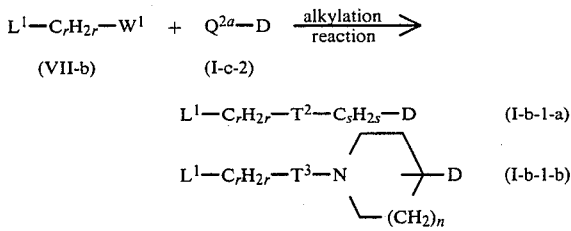

In (I-c-2) $Q^{2a}$ is a radical of formula $HT^2—C_sH_{2s}—$, respectively a radical of formula

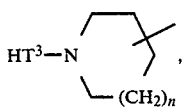

and $W^1$ has the previously defined meaning of W, and where $r=0$, and $L^1$ is Het or $Ar^1$, it may also be lower alkyloxy or lower alkylthio.

The compounds of formula (I-b), wherein $L^2$ is a radical of formula (b-1-a), wherein T is $T^4$, said $T^4$ being O, S, $NR^3$ or $—Z—C(=X)—Y^1—$, said $Y^1$ being O, S or $NR^3$, and said compounds being represented by the formula (I-b-2), may also be prepared by alkylating a piperidine of formula (I-c) wherein $Q^2$ is a radical of formula $—C_sH_{2s}—W$, said piperidine being represented by the formula (I-c-3), with a reagent of formula (VII) wherein $Q^1$ is a radical of formula $—C_rH_{2r}—T^4H$, said reagent being represented by the formula (VII-c).

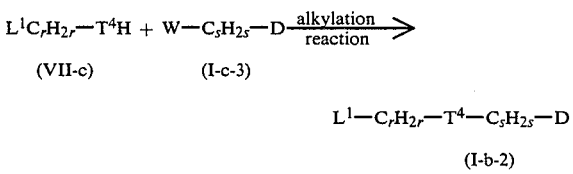

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); dimethyl sulfoxide (DMSO); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I-b) can also be prepared by the reductive N-alkylation reaction of (I-c-1) with an appropriate carbonyl-compound of formula $L^{2-a}=C=O$ (VIII), said $L^{2-a}=C=O$ being a compound of formula $L^2-H$ wherein a $—CH_2—$ radical is oxidated to a carbonyl radical.

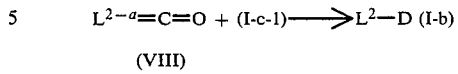

The compounds of formula (I-b), wherein $L^2$ is a radical of formula $L^1—C_rH_{2r}—NR^3—C_sH_{2s}—$, said compounds being represented by the formula (I-b-3) may alternatively be prepared by the reductive N-alkylation reaction of a compound of formula (I), wherein L is a radical of formula $HN(R^3)—C_sH_{2s}—$, (I-d), with an appropriate carbonyl-compound of formula $L^1—(C_rH_{2r-1})=O$, (IX), said $L^1—(C_rH_{2r-1})=O$ being a compound of formula $L^1—C_rH_{2r}—H$ wherein a $—CH_2—$ radical is oxidated to a carbonyl radical. The compounds of formula (I-b-3) can also be prepared by the reductive N-alkylation of an amine of formula (X), with a compound of formula (I) wherein L is a radical of formula $O=(C_2H_{2s-1})—$, said compound being represented by the formula (I-e), and said $O=(C_sH_{2s-1})—$ being a radical of formula $H—C_sH_{2s}—$ wherein a $—CH_2—$ radical is oxidated to a carbonyl radical.

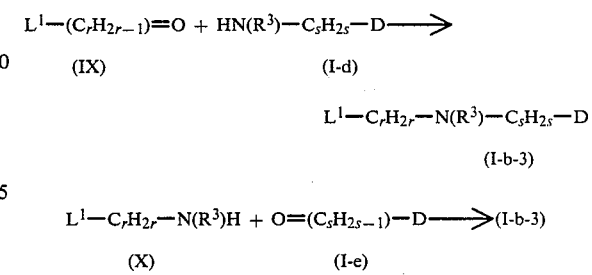

Said reductive N-alkylation reaction may conveniently be carried out by catalytically hydrogenating a mixture of the reactants in a suitable reaction-inert organic solvent according to art-known catalytic hydrogenating procedures. The reaction mixture may be stirred and/or heated in order to enhance the reaction rate. Suitable solvents are, for example, water; lower alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; dimethyl sulfoxide and the like; or a mixture of 2 or more of such solvents. The term "art-known catalytic hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I-b), wherein L is a radical of formula (b-1-a) wherein T is $Z^1—C(=X^2)—NH—$, $Z^1$ being as previously described, $X^2$ being O or S, and said compounds being represented by the formula (I-b-4), can generally be prepared by reacting an isocyanate or isothiocyanate of formula (I-f) with a reagent of formula (XI):

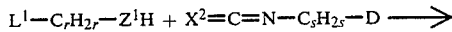

(XI)  (I-f)

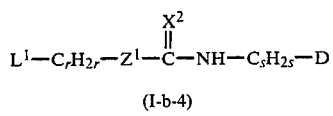

(I-b-4)

The compounds of formula (I-b), wherein $L^2$ is a radical of formula (b-1-a), wherein T is $-NH-C(=X^2)-Y^1-$, $Y^1$ being as previously described, and the compounds of formula (I-b), wherein $L^2$ is a radical of formula (b-1-a), wherein T is $-NH-C(=X^2)-$ and s is 0, and the compounds of formula (I-b), wherein $L^2$ is a radical of formula (b-2), wherein $T^1$ is $-NH-C(=X^2)-$, said compounds being represented by the formula (I-b-5-a), respectively (I-b-5-b) and (I-b-5-c), can be prepared by reacting an isocyanate or isothiocyanate of formula (XII) with a piperidine of formula (I-c-4), respectively (I-c-1) and (I-c-5).

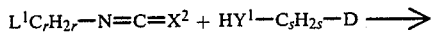

(XII)  (I-c-4)

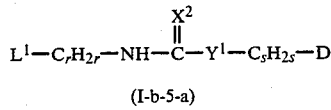

(I-b-5-a)

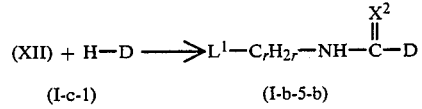

(I-c-1)  (I-b-5-b)

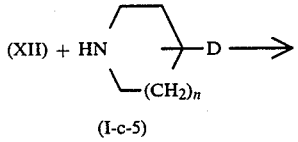

(I-c-5)

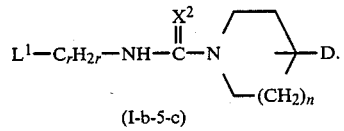

(I-b-5-c)

The reaction of (XI) with (I-f) and of (XII) with (I-c-4), respectively (I-c-1) and (I-c-5) may be conducted in a suitable reaction-inert solvent such as, for example, a hydrocarbon, e.g., benzene, a ketone, e.g., acetone, a halogenated hydrocarbon, e.g., dichloromethane, trichloromethane, an ether, e.g., 1,1'-oxybisethane, tetrahydrofuran and the like. Elevated temperatures may be suitable to enhance the rate of the reaction.

The compounds of formula (I-b), wherein $L^2$ is a radical of formula (b-1-a), wherein T is $-C(=X^2)-Y^1-$, and the compounds of formula (I-b), wherein L is a radical of formula (b-1-a), wherein s is 0 and T is a radical of formula $-C(=X^2)-$, and the compounds of formula (I-b) wherein $L^2$ is a radical of formula (b-2), wherein $T^1$ is $-C(=X^2)-$, said compounds being represented by the formula (I-b-6-a), respectively (I-b-6-b) and (I-b-6-c), may be prepared by reacting a piperidine of formula (I-c-4), respectively (I-c-1) and (I-c-5) with a reagent of formula (XIII).

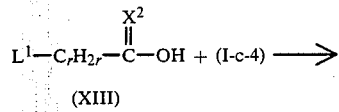

(XIII)

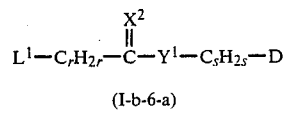

(I-b-6-a)

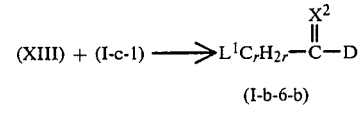

(I-b-6-b)

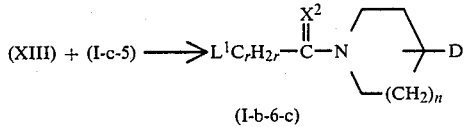

(I-b-6-c)

The reaction of (XIII) with (I-c-4), respectively (I-c-1) and (I-c-5) may generally be conducted following art-known esterification- or amidation reaction-procedures. For example, the carboxylic acid may be converted into a reactive derivative, e.g., an anhydride or a carboxylic acid halide, which subsequently, is reacted with (I-c-4), (I-c-1) or (I-c-5); or by reacting (XIII) and (I-c-4), respectively (I-c-1) and (I-c-5) with a suitable reagent capable of forming amides or esters, e.g., dicyclohexylcarbodiimide, 2-chloro-1-methylpyridinium iodide and the like. Said reactions are most conveniently conducted in a suitable solvent such as, for example, an ether, e.g. tetrahydrofuran, a halogenated hydrocarbon, e.g. dichloromethane, trichloromethane or a polar aprotic solvent, e.g. N,N-dimethylformamide. The addition of a base, e.g. N,N-diethylethanamine may be appropriate.

The compounds of formula (I-b), wherein $L^2$ is a radical of formula (b-1-a) wherein T is $-Z^1-C(=X)-Y^1-$, and the compounds of formula (I-b), wherein $L^2$ is a radical of formula (b-1-a) wherein s is 0 and T is $-Z^1-(C=X)-$, and the compounds of formula (I-b), wherein $L^2$ is a radical of formula (b-2) wherein $T^1$ is $-Z^1-C(=X)-$, said compounds being represented by the formula (I-b-7-a), respectively (I-b-7-a) and (I-b-7-c), can also be prepared by reacting (XI) with (I-c-4), respectively (I-c-1) and (I-c-5) in the presence of an appropriate

generating agent.

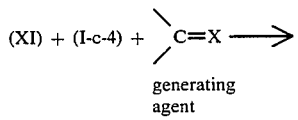

generating agent $$L^1-C_rH_{2r}-Z^1-C(=X)-Y^1-C_sH_{2s}-D$$
(I-b-7-a)

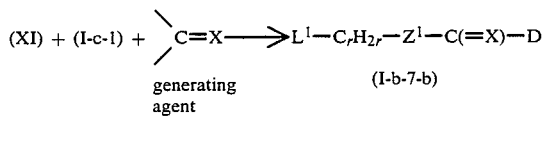
(I-b-7-b)

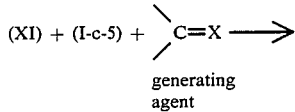

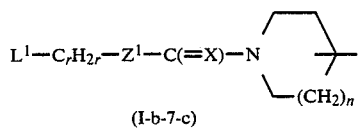
(I-b-7-c)

An appropriate

generating agent is, for example, 1,1'-thiocarbonylbis[1H-imidazole], 1,1'-carbonylbis[1H-imidazole], carbonic dichloride, carbonothioic dichloride, urea, thiourea, trichloroacetyl chloride, and the like. The reaction of (XI) with (I-c-4), (I-c-1) or (I-c-5) is conveniently conducted in a suitable solvent, such as, for example, a hydrocarbon, e.g., benzene, methylbenzene; an ether, e.g., 1,1'-oxybisethane, tetrahydrofuran; a halogenated hydrocarbon, e.g., dichloromethane, trichloromethane and the like. The addition of a base such as, for example, an alkali metal carbonate or hydrogen carbonate or an organic base, e.g., N,N-diethylethanamine and the like, may be appropriate.

The compounds of formula (I-b) wherein $L^2$ is a radical of formula (b-1), wherein s is an integer of from 2 to 6 inclusive, and compounds being represented by the formula (I-g) can be prepared by reacting an appropriate alkene of formula (XIV) with a piperidine of formula (I-c-1).

$$L^1C_rH_{2r}-T-\text{lower alkenediyl-H} + (I-c-1) \longrightarrow$$
(XIV)

$$L^1C_rH_{2r}-T-\text{lower alkenediyl-D}$$
(I-g)

The compounds of formula (I-b) wherein $L^2$ is a radical of formula $L^1-C_rH_{2r}-T-C_{s'-2}H_{2s'-4}-CH(Y^1H)-CH_2-$, wherein s' is an integer of from 2 to 6 inclusive, said compounds being represented by the formula (I-h) may also be prepared by reacting a reagent of formula (XV) with a piperidine of formula (I-c-1).

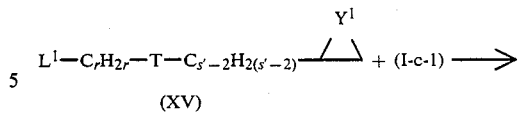
(XV)

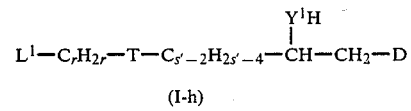
(I-h)

The reactions of (XIV) with (I-c-1), and (XV) with (I-c-1) may be conducted by stirring and, if desired, heating the reactants together. The said reactions may be conducted in a suitable solvent such as, for example, an alkanone, e.g. 2-propanone, 4-methyl-2-propanone, an ether, e.g. tetrahydrofuran, 1,1'-oxybisethane, an alcohol, e.g. methanol, ethanol, 1-butanol, N,N-dimethylformamide, N,N-dimethylacetamide and the like.

It is evident that the radical "-lower alkenyl-", the corresponding "-lower alkanediyl-" radical and the radical $C_{2s'-2}H_{2s'-4}$ may bear the previously described substitutions of the radical $-C_sH_{2s}-$.

The compounds of formula (I) wherein $L^1$ is Het, said compounds being represented by the formula (I-i), may also be prepared following procedures for preparing ring systems which are known in the art or analogous procedures thereof. A number of such cyclization procedures will be described hereinafter.

The bivalent radical K used in the description of these cyclization reactions has the following meaning:

$$-C_rH_{2r}-T-C_sH_{2s}- \quad (d-1);$$

or

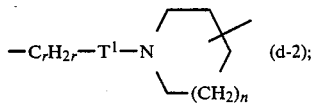

and the radicals (e-1-a), (e-2), (e-3), (e-5-a), (e-6), (e-7) and (e-8) also used in the description of these cyclization reactions have the following meaning:

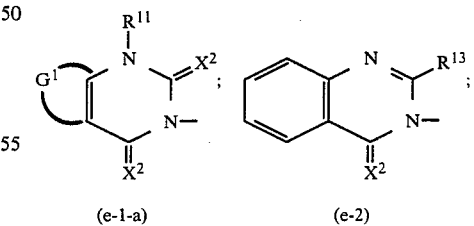

(e-1-a)   (e-2)

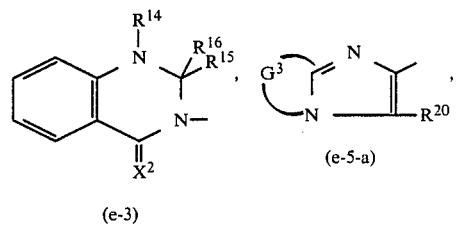

(e-3)   (e-5-a)

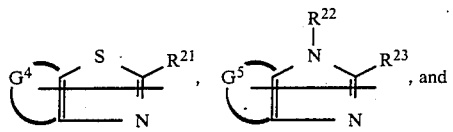

(e-6) (e-7)

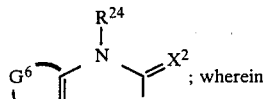

(e-8)

$X^2$, $R^{11}$, $R^{13}$, $R^{14}$, $R^{15}$, $R^{16}$, $R^{20}$, $R^{21}$, $R^{22}$, $R^{23}$, $R^{24}$, $G^1$, $G^3$, $G^4$, $G^5$ and $G^6$ have the same meaning as defined hereinabove for the particularly preferred compounds.

For example, the compounds of formula (I-i) wherein Het is an optionally substituted imidazolyl radical, said compounds being represented by the formula (I-i-1), can be prepared by the cyclization reaction of an appropriate N-(2,2-dilower alkyloxyethyl)imidamide derivative of formula (XVI).

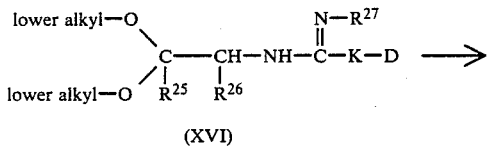

(XVI)

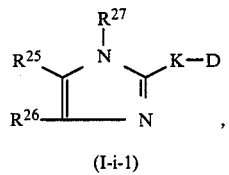

(I-i-1)

wherein $R^{25}$, $R^{26}$ and $R^{27}$ are each independently optional substituents of the imidazole ring.

Said cyclization reaction may conveniently be conducted in a suitable solvent in the presence of an appropriate acid such as, for example, hydrochloric, hydrobromic and the like acids. Elevated temperatures may enhance the rate of the reaction.

The compounds of formula (I-i) wherein Het is an optionally substituted thiazolyl radical, being optionally condensed with a five- or six-membered hetero- or carbocyclic ring, may be prepared by a number of cyclization reactions, yielding, depending upon the case, compounds which may be represented by the formula (I-i-2) or (I-i-3).

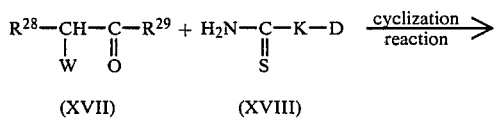

(XVII) (XVIII)

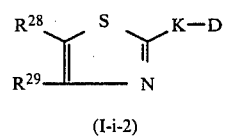

(I-i-2)

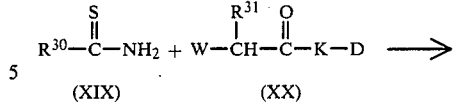

(XIX) (XX)

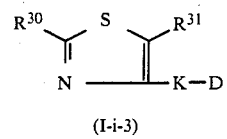

(I-i-3)

$R^{28}$, $R^{29}$, $R^{30}$ and $R^{31}$ are each independently optional substituents of the said thiazolyl ring, or, where in the compounds of formula (I-i-2) said thiazolyl ring is condensed with a five- or six-membered hetero- or carbocyclic ring, $R^{28}$ and $R^{29}$ taken together may form a bivalent radical of formula $G^4$.

Further, where Het is a radical of formula (e-1-a), said Het may be formed by condensing an intermediate (XXI) with a

generating agent, e.g. urea, thiourea, 1,1'-carbonyl-bis[1H-imidazole], lower alkyl carbonohalidate, phosgene, thiophosgene, trichloromethyl carbonohalidate and the like.

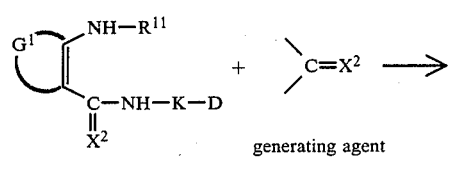

(XXI)

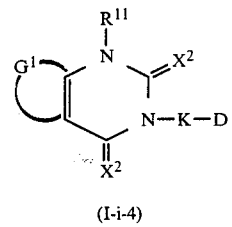

(I-i-4)

The compounds of formula (I-i-4) wherein $R^{11}$ is hydrogen may additionally be prepared by cyclizing an intermediate of formula

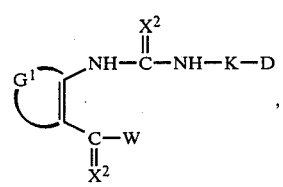

(XXII)

which may in situ be generated by reacting a reagent (XXIII) with an amine (XXIV).

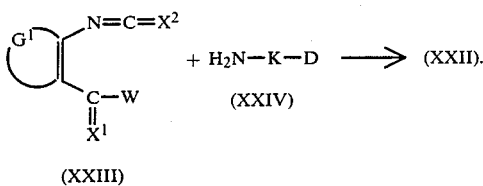

(XXIII)

The reaction of (XXI) with the

generating agent and the cyclization of (XXII) may conveniently be conducted in a suitable solvent such as, for example, an ether, e.g. 1,1-oxybisethane, tetrahydrofuran, an halogenated hydrocarbon, e.g. dichloromethane, trichloromethane, a hydrocarbon, e.g. benzene, methylbenzene, an alcohol, e.g. methanol, ethanol, a ketone, e.g. 2-propanone, 4-methyl-2-pentanone, N,N-dimethylformamide, N,N-dimethylacetamide, or mixture of such solvents, optionally in the presence of an appropriate base such as, for example, N,N-diethylethanamine, an alkali or earth alkaline metal carbonate or hydrogen carbonate. In order to enhance the reaction rate, it may be suitable to heat the reaction mixture.

Further, where Het is a radical of formula (e-2), said Het may be generated by cyclizing an intermediate (XXV) with an acid (XXVI) or a suitable functional derivative thereof, thus preparing a compound of formula (I-i-5). Alternatively an intermediate (XXVII) may be condensed with an aromatic amino acid or -thioacid of formula (XXVIII), preparing also a compound (I-i-5).

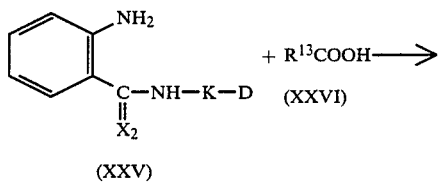

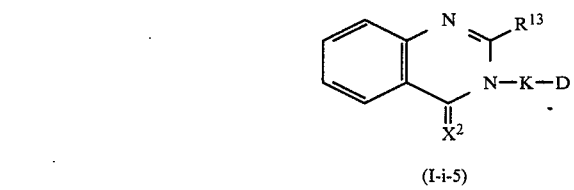

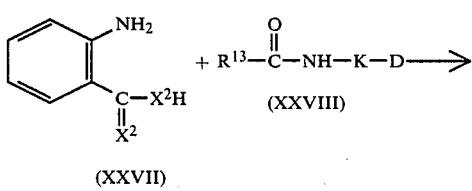

The reaction of (XXV) with (XXVI) and of (XXVII) with (XXVIII) may be conducted in a suitable reaction-inert solvent, such as, for example, a hydrocarbon, e.g. benzene, methylbenzene, an alcohol, water. In some instances it may be appropriate to use higher temperatures in order to reduce the reaction time.

Where Het is a radical of formula (e-3), wherein $R^{16}$ is hydrogen and $R^{15}$ is a radical of formula $R^{15\text{-}a}$—$CH_2$—, said Het may be formed by reacting a compound (XXIV) with an appropriate acetylene derivative (XXX), thus preparing a compound of formula (I-i-6).

Additionally, where Het is a radical of formula (e-3), said Het may be formed by reacting (XXIX) with a ketone of formula (XXXI), thus preparing a compound of formula (I-i-7).

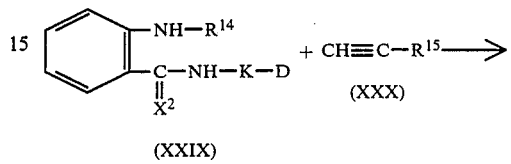

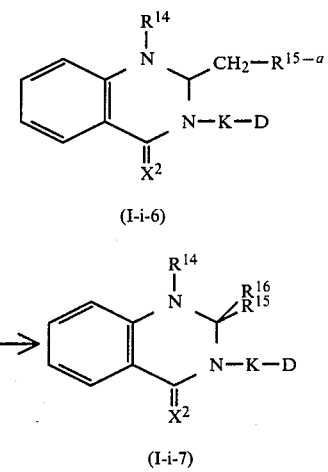

The reaction of (XXIX) with (XXX) may be conducted in a suitable solvent such as, for example, an alcohol, e.g. methanol, ethanol, while the reaction of (XXIX) with (XXXI) may be conducted in a suitable solvent preferably in the presence of an organic acid such as, for example, ethanedioic acid and the like. Elevated temperatures may also be appropriate to shorten the reaction time.

Additionally, where Het is a radical (e-5-a), said Het may be created by condensing a reagent (XXXII) with an intermediate (XXXIII), thus giving a compound (I-i-8).

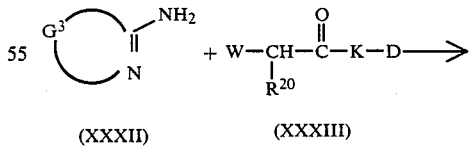

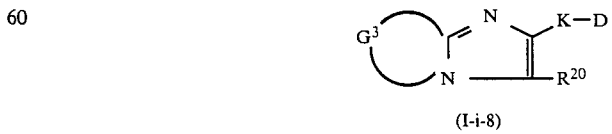

Where Het is a radical (e-6) being connected to K by the $G^4$ containing ring and bearing a 2-mercaptosubstituent, said Het may be formed during the cyclization of an intermediate (XXXII) with CS₂, thus preparing a compound (I-i-9).

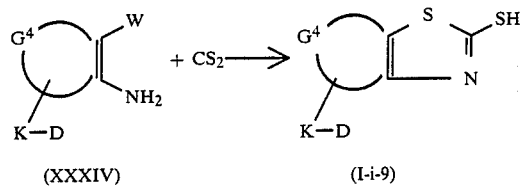

(XXXIV)     (I-i-9)

Where Het is a radical of formula (e-7) being connected to K either by the $G^5$ containing ring or by the imidazole ring, said Het is formed during the condensation reaction of a reagent (XXXV) with an intermediate (XXXVI) respectively by the cyclodesulfurization reaction of an intermediate (XXXVII), thus preparing a compound (I-i-10) respectively (I-i-11).

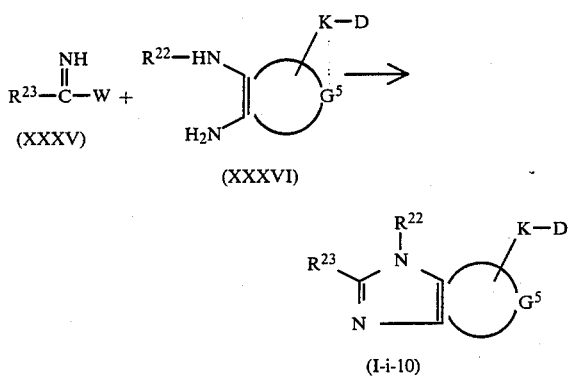

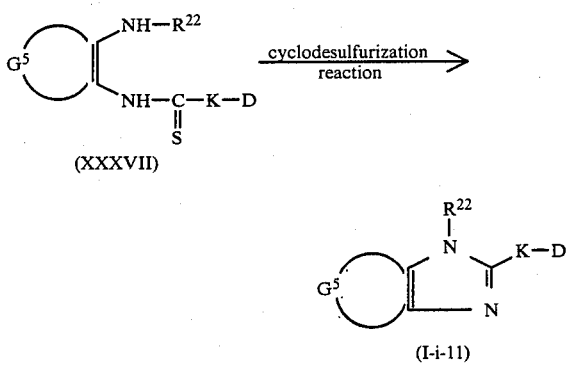

The reactions of (XXXII) with (XXXIII), of (XXXIV) with CS₂ and (XXXV) with (XXXVI) may conveniently conducted in a suitable reaction-inert solvent, such as for example one of the solvents given hereinabove for the preparation of (I-i-4) optionally in the presence of an appropriate base, e.g. one of the bases also described for the preparation of (I-i-4); higher temperatures may be used to enhance the reaction rate.

The cyclodesulfurization of (XXXVII) may be carried out by the reaction of (XXXVII) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (XXXVII) with an appropriate metal oxide or salt in an appropriate solvent according to art-known procedures. For example, the compounds of formula (I) can easily be prepared by the reaction of (XXXVII) with an appropriate Hg(II) or Pb(II) oxide or salt, such as, for example HgO, HgCl₂, Hg(OAc)₂, PbO or Pb(OAc)₂. In certain instances it may be appropriate to supplement the reaction mixture with a small amount of sulfur. Even so methanediimines, especially N,N'-methanetetraylbis[cyclohexaneamine] may be used as cyclodesulfurizing agents.

Where Het is a radical (e-8), said Het may be formed during the condensation of an intermediate (XXXVIII) with a

generating agent, following the same procedure as previously described for the preparation of (I-i-4) starting from (XXXIII).

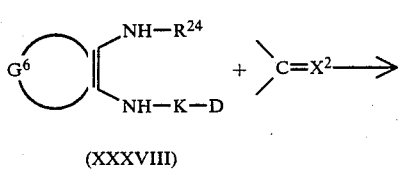

(XXXVIII)

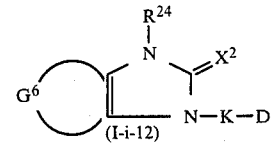

(I-i-12)

The compounds of formula (I) can also be converted into each other following art-known procedures of functional grouptransformation. Some examples will be cited hereinafter.

The compounds of formula (I), wherein —B— is —S— may be converted into the corresponding compounds of formula (I), wherein —B— is —SO— or —SO₂— by an appropriate oxidation reaction, e.g. by reacting the former compounds with a suitable oxidating agent such as, for example, potassium periodate, a peroxide, e.g. 3-chlorobenzenecarboperoxoic acid, hydrogen peroxide, and the like, in a suitable solvent such as, for example, an ether, e.g. tetrahydrofuran, 1,1'-oxybisethane, a hydrocarbon, e.g. benzene, a halogenated hydrocarbon, e.g. dichloromethane, trichloromethane and the like. In the instance where a sulfinyl is desired, said oxidation reaction is preferably conducted at lower temperatures with approximately one equivalent of the oxidating agent, while where a sulfonyl is desired, said oxidation reaction may be conducted at room or elevated temperature with an excess of oxidating agent.

The compounds of formula (I) having a nitro substituent can be converted into the corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g., methanol, ethanol and the like.

In an analogous procedure, the compounds of formula (I) having a cyano substituent, can be converted into the corresponding aminomethyl containing compounds.

The compounds of formula (I) having an hydroxy substituent may be converted into the corresponding halo compounds following art-known halogenating procedures, e.g., by reacting the former compounds with a suitable halogenating agent, e.g. thionyl chloride, phosphoryl chloride, phosphor trichloride, phosphor pentachloride, thionyl bromide, phosphor tribromide and the like.

The compounds of formula (I) containing an ester group may be converted into the corresponding carboxylic acids following art-known saponification procedures, e.g., by treating the said compounds with an aqueous alkaline solution or with an aqueous acidic solution.

The compounds of formula (I) containing a Het substituted with a thioxo group can be converted into the corresponding oxo compounds following art-known procedures, for example, by treating the said thioxo containing compounds with a peroxide, e.g. hydrogen peroxide in a suitable alkaline medium, e.g. an aqueous alkali metal hydroxide solution which may be mixed with an organic solvent, such as, for example, methanol, ethanol and the like.

The compounds of formula (I) containing an unsaturated Het can be converted into the corresponding saturated form following art-known reducing procedures, e.g. by treating the said compounds with hydrogen in the presence of a suitable catalyst such as, for example, platinum-on-charcoal, palladium-on-charcoal an the like catalysts.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst, e.g., palladium-on-charcoal and the like catalysts. Said halo atoms may also be replaced by a lower alkyloxy or a lower alkylthio substituent by reacting the starting halo-compound with an appropriate alcohol or thioalcohol or, preferably, an alkali- or earth alkaline metal salt or an appropriate alcohol or thioalcohol in a suitable solvent.

Lower alkyloxy and lower alkylthio radicals substituted on aryl may be converted into the corresponding hydroxy or thiol radicals by treating them with an aqueous acidic solution, e.g. an aqueous hydrochloric or hydrobromic solution.

The compounds of formula (I) containing an imino group, e.g. where $NR^1$, $NR^3$, $NR^4$ or $NR^5$ is NH, or an amino group, e.g. where $AR^1$, $AR^2$ or Het is substituted with an amino group, the hydrogen atom in said imino or amino may be replaced by a suitable substituent following art-known procedures such as, for example, N-alkylation, reductive N-alkylation, acylation and the like methods. A number of such procedures will be described hereinafter in more detail. For example, lower alkyl groups or substituted lower alkyl groups may be introduced by reacting the starting compounds with an appropriate N-alkylating agent following the procedures described hereinabove for the N-alkylation reactions of (VII) with (I-c), or by reacting the starting compounds with an appropriate carbonyl-compound following the reductive N-alkylation procedures described hereinabove for the reductive N-alkylations of (I-c-1) with (VIII), (I-d) with (IX) and (I-e) with (X).

Lower alkylcarbonyl, $Ar^2$-carbonyl and the like groups may be introduced by reacting the starting amine with an appropriate carboxylic acid or a derivative thereof such as, for example, an acid halide, acid anhydride and the like.

Lower alkyloxycarbonyl and $Ar^2$-oxycarbonyl groups can be introduced by reacting the starting amine compound with an appropriate carbonohalidate, e.g. ethyl carbonohalidate, phenylmethyl carbonohalidate and the like.

$Ar^2$—NH—CO, $Ar^2$—NH—CS, (lower alkylamino)—CO— (lower alkylamino)—CS—, and the like groups can conveniently introduced by reacting the starting amine compounds with an appropriate isocyanate or isothiocyanate following the procedures described hereinabove for the preparation of (I-b-4), (I-b-5-a), (I-b-5-b) and (I-b-5-c).

The compounds of formula (I) containing a substituted nitrogen atom may be converted into the corresponding compounds of formula (I) wherein said nitrogen bears a hydrogen atom following art-known methods for preparing N—H groups such as, for example:

1. where said nitrogen is substituted with an $Ar^2$—$CH_2$ group, by treating the starting compounds with hydrogen in the presence of a suitable catalyst, e.g. palladium-on-charcoal, platinum-on-charcoal, in an appropriate solvent;

2. or, where said nitrogen is substituted with a sulfonyl group, e.g lower alkylsulfonyl and $Ar^2$-sulfonyl, by treating the starting compounds with an aqueous acidic solution preferably in the presence of a catalyst such as, for example, phenol, methoxybenzene and the like;

3. or, where said nitrogen atoms are substituted with an $Ar^2$-carbonyl group by treating the starting compounds with an aqueous basic solution, e.g. a alkali metal solution;

4. where said nitrogen is substituted with lower alkyloxy carbonyl or $Ar^2$-oxycarbonyl, by treating the starting compounds with an aqueous acidic or aqueous basic solution optionally in admixture with an organic solvent or where said nitrogen atom is substituted with $Ar^2$-oxycarbonyl, by catalytically hydrogenating the starting materials in a suitable solvent.

The compounds of formula (I) containing a nitrogen atom substituted with $Ar^2$—$CH_2$— may be converted into the corresponding compounds where said nitrogen is substituted with lower alkyloxycarbonyl, for example by treating the former compounds with a lower alkyl carbonohalidate in the presence of a suitable solvent and, if desired, in the presence of an appropriate base.

The compounds of formula (I) containing a mercapto group may be converted into the corresponding isothiocyanato containing compounds by treating the starting amino compounds with $CS_2$ in the presence of N,N'-methanetetraylbis[cyclohexanamine].

The compounds of formula (I) containing a —$CH_2$—C(=O)— fragment can be converted into the corresponding compounds of formula (I) containing a —CH(halo)—C(=O)— fragment following art-known halogenating procedures, e.g. by treating the starting compound with a halogen.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (II), wherein B is $CH_2$, $X^1$ is NH and W is lower alkyloxy, said intermediates being represented by the formula (II-a), can be prepared by reacting a (cyanomethyl)piperidine of the formula (XXXIX) with an alcohol, e.g. methanol, ethanol and the like, in the presence of an acid, e.g. hydrochloric acid.

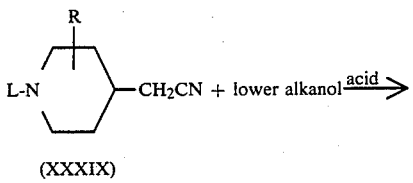

(XXXIX)

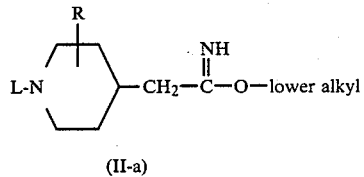

(II-a)

The intermediates of formula (IV) may be prepared by a reduction reaction of an appropriate 4-piperidinone, and, if desired, followed by an appropriate art-known groupstransformation procedure, e.g., where a compound of formula (V-b) is desired, by reacting the thus obtained alcohol with thionyl chloride, methylsulfonyl chloride and the like in order to obtain an appropriate leaving group.

The intermediates of formula (VI) can be prepared by reacting an appropriate bicyclic condensed imidazole derivative with a pyridinium derivative.

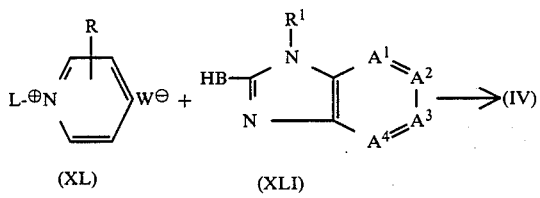

The intermediates of formula (VII) can conveniently be prepared following art-known procedures as described in, for example, U.S. Pat. No. 4,335,127, U.S. Pat. No. 4,342,870 and European Patent Publication No. 0,070,053.

From formula (I) it is evident that the compounds of this invention may have several assymetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The following examples are intended to illustrate and not to limit the scope of the present invention. Unless otherwise stated all parts therein are by weight.

EXPERIMENTAL PART

A. Preparation of Intermediates

EXAMPLE 1

(a) A mixture of 302 parts of ethyl 2-[1-(phenylmethyl)-4-piperidinylidene]acetate hydrochloride and 200 parts of glacial acetic acid was hydrogenated at normal pressure and at a temperature between 24°–36° C., in the presence of 4 parts of platinum oxide. After the calculated amount of hydrogen was taken up, the catalyst was filtered off and the filtrate was evaporated. The residue was washed with 1,1'-oxybisethane, alkalized with sodium hydroxide and extracted with 1,1'-oxybisethane. The extract was dried over potassium carbonate and evaporated. The oily residue was distilled in vacuo, yielding 205 parts of the crude oily free base. From this oil 1 part was taken to prepare the hydrochloride salt. It was dissolved in 1,1'-oxybisethane and gaseous hydrogen chloride was introduced into the solution: a semi-solid salt was precipitated. The solvent was decanted and the residue was dissolved again in a mixture of 6 parts of ethanol and 4 parts of 1,1'-oxybisethane. This solution was concentrated to 5 parts. To the residue were added 12 parts of 1,1'-oxybisethane, whereupon a solid was precipitated. It was filtered off and dried, yielding 0.2 parts of ethyl 1-(phenylmethyl)-4-piperidineacetate hydrochloride; mp. 122.5°–137° C. (intermediate 1).

(b) A mixture of 8 parts of ethyl 1-(phenylmethyl)-4-piperidineacetate hydrochloride and 80 parts of a dilute hydrochloric acid solution was stirred and refluxed for 4 hours. After cooling, the reaction mixture was evaporated. The residue was washed with 2-propanone and the solvent was evaporated again. The solid residue was washed with 2-propanone, filtered off and dried, yielding 6 parts of 1-(phenylmethyl)-4-piperidineacetic acid hydrochloride; mp. 137°–145° C. (2).

EXAMPLE 2

To a suspension of 68.5 parts of ethyl 4-oxo-1-piperidinecarboxylate in 240 parts of methanol was added portionwise 3.8 parts of sodium borohydride at a temperature between 20°–30° C. (the reaction mixture was cooled if necessary in a water-bath). After the addition was complete, the whole was stirred for 30 minutes. The reaction mixture was then poured into a mixture of 53.5 parts of ammonium chloride and 400 parts of water. The methanol was evaporated. The product was extracted with trichloromethane. The extract was dried and evaporated. The oily residue was distilled in vacuo, yielding 60 parts of oily ethyl 4-hydroxy-1-piperidinecarboxylate; bp. 140° C. at 1.4 mm. pressure; $n_D^{20}$: 1.4796; $d_{20}^{20}$: 1.1166 (3).

In a similar manner there was also prepared:
methyl (cis+trans)-4-hydroxy-3-methyl-1-piperidinecarboxylate (4).

EXAMPLE 3

To a stirred solution of 90 parts of 1-[(4-methylphenyl)sulfonyl]-4-piperidinol, 37.5 parts of N,N-diethylethanamine and 1300 parts of dichloromethane was added dropwise a solution of 42.3 parts of methanesulfonyl chloride in 130 parts of dichloromethane (exothermic reaction: temperature rose to 35° C.). Upon completion, stirring was continued for 2 hours at room temperature. Water was added and the layers were separated. The organic phase was washed with water, dried, filtered and evaporated. The residue was suspended in 2,2'-oxybispropane. The product was filtered off and dried, yielding 116 parts (100%) of 1-[(4-methylphenyl)sulfonyl]-4-piperidinol methanesulfonate (ester); mp. 168.5°–175.3° C. (5).

EXAMPLE 4

2350 Parts of hydrogen chloride were bubbled through 5600 parts of cooled ethanol (ice bath) at 10° C. Then there were added dropwise, during a 45 minutes period, 1500 parts of 1-(phenylmethyl)-4-piperidineacetonitrile. Upon completion, the whole was stirred for 20 hours at room temperature. The reaction mixture was evaporated and the residue was stirred in 2400 parts of acetonitrile. The product was filtered off, washed with 560 parts of acetonitrile and dried, yielding 2000 parts (85.7%) of O-ethyl 1-(phenylmethyl)-4-piperidineethanimidate hydrochloride (6).

In a similar manner there was also prepared:
O-methyl 1-(phenylmethyl)-4-piperidineethanimidate dihydrochloride (7).

EXAMPLE 5

A mixture of 180.0 parts of 2-chloro-3-nitropyridine, 122.0 parts of 2-thiophenemethanamine, 191.0 parts of sodium carbonate, 1 part of potassium iodide and 810 parts of N,N-dimethylacetamide was stirred for 1.50 hours at 100° C. The reaction mixture was poured into about 4000 parts of water. The whole was stirred overnight at room temperature. The precipitated product was filtered off and dried in vacuo at 40° C., yielding 251.5 parts of 3-nitro-N-(2-thienylmethyl)-2-pyridinamine; mp. 100° C. (8).

Following the same procedure and using equivalent amounts of the appropriate starting materials, there were also prepared:
N-(2-nitrophenyl)-3-pyridinemethanamine (9);
N-(4-fluorophenylmethyl)-3-nitro-2-pyridinamine; mp. 76° C. (10)
N-(3-nitro-2-pyridinyl)-2-pyridinemethanamine; mp. 113.6° C. (11)
2-nitro-N-(2-thienylmethyl)benzenamine (12);
4-methyl-N-(2-nitrophenyl)benzenemethanamine; mp. 65° C. (13);
N-[(4-methylphenyl)methyl]-3-nitro-2-pyridinamine; mp. 80.0°–87.3° C. (14);
$N^3$-[(4-fluorophenyl)methyl]-2,3-pyridineamine (15);
N-[(4-fluorophenyl)methyl]-3-nitro-4-pyridineamine; mp. 136.8° C. (16);
N-[(4-fluorophenyl)methyl]-4-nitro-3-pyridineamine, 1-oxide (17);
4-fluoro-N-(4-methoxy-2-nitrophenyl)benzenemethanamine (18);
4-fluoro-N-(5-methoxy-2-nitrophenyl)benzenemethanamine (19);
4-fluoro-N-(4-methyl-2-nitrophenyl)benzenemethanamine; mp. 99.9° C. (20).

In a similar manner, there are also prepared:
4-fluoro-N-(3-methoxy-2-nitrophenyl)benzenemethanamine; (21);
4-fluoro-N-(2-methoxy-6-nitrophenyl)benzenemethanamine; (22);
4-fluoro-N-(4,5-dimethoxy-2-nitrophenyl)benzenemethanamine; (23);
4-fluoro-N-(4-chloro-5-methoxy-2-nitrophenyl)benzenemethanamine; (24);
4-fluoro-N-(5-chloro-4-methoxy-2-nitrophenyl)benzenemethanamine; (25);
N-(4-methoxy-2-nitrophenyl)-2-furanmethanamine; (26);
N-(5-methoxy-2-nitrophenyl)-2-furanmethanamine; (27);
N-(4-methoxy-2-nitrophenyl)-2-pyridinemethanamine; (28);
N-(5-methoxy-2-nitrophenyl)-2-pyridinemethanamide; (29);
N-[(4-fluorophenyl)methyl]-6-methoxy-3-nitro-2-pyridinamine; (30);
N-[(2-furanyl)methyl]-6-methoxy-3-nitro-2-pyridinamine; (31); and
N-(3-nitro-6-methoxy-2-pyridinyl)-2-pyridinemethanamine; (32).

EXAMPLE 6

To a stirred and cooled mixture of 40 parts of N-[(4-fluorophenyl)methyl]-4-nitro-3-pyridinamine, 1-oxide and 1050 parts of trichloromethane were added dropwise 47 parts of phosphor pentachloride at a temperature between 0° and −10° C. Upon completion, the whole was stirred and refluxed for 1 hour. While stirring, the reaction mixture was cooled. The precipitated product was filtered off, stirred in water and alkalized with ammonium hydroxide. The product was extracted with trichloromethane. The extract was dried, filtered and evaporated. The residue was stirred in 2,2'-oxybispropane. The product was filtered off and dried, yielding 22.2 parts of N-[(4-fluorophenyl)methyl]-4-nitro-3-pyridinamine; mp. 91.9° C. (33).

EXAMPLE 7

A mixture of 100 parts of N-[(4-methoxyphenyl)methyl]-3-nitro-2-pyridinamine, 3 parts of a solution of thiophene in methanol 4% and 480 parts of methanol saturated with ammonia was hydrogenated at normal pressure and at 50° C. with 5 parts of palladium-oncharcoal catalyst 10%. After the calculated amount of hydrogen was taken up, the catalyst was filtered off and the filtrate was evaporated, yielding 88.4 parts of $N^2$-[(4-methoxyphenyl)methyl]-2,3-pyridinediamine; mp. 118.1° C. (34).

In a similar manner there were also prepared:
N-(3-pyridinylmethyl)-1,2-benzenediamine (35);
$N^2$-[(4-fluorophenyl)methyl]-2,3-pyridinediamine (36);
$N^2$-(2-pyridinylmethyl)-2,3-pyridinediamine; mp. 134.9 (37);
$N^2$-(2-furanylmethyl)-2,3-pyridinediamine (38);
$N^1$-(2-thienylmethyl)-1,2-benzenediamine (39);
$N^2$-(2-thienylmethyl)-2,3-pyridinediamine; mp. 92.1° C. (40);
$N^1$-[(4-methylphenyl)methyl]-1,2-benzenediamine (41);
$N^2$-[(4-methylphenyl)methyl]-2,3-pyridinediamine; mp. 125.1° C. (42);
$N^4$-[(4-fluorophenyl)methyl]-3,4-pyridinediamine; mp. 163.7° C. (43);
$N^3$-[(4-fluorophenyl)methyl]-3,4-pyridinediamine; mp. 159.6° C. (44);
$N^1$-[(4-fluorophenyl)methyl]-4-methoxy-1,2-benzenediamine (45);
$N^2$-[(4-fluorophenyl)methyl]-4-methoxy-1,2-benzenediamine (46);
$N^1$-[(4-fluorophenyl)methyl]-4-methyl-1,2-benzenediamine (47);
N-[(5-methyl-2-furanyl)methyl]-1,2-benzenediamine (48).

In a similar manner there are also prepared:
$N^1$-[(4-fluorophenyl)methyl]-3-methoxy-1,2-benzenediamine (49);
$N^1$-[(4-fluorophenyl)methyl]-6-methoxy-1,2-benzenediamine (50);
$N^1$-[(4-fluorophenyl)methyl]-4,5-dimethoxy-1,2-benzenediamine (51);
$N^1$-[(4-fluorophenyl)methyl]-5-chloro-4-methoxy-1,2-benzenediamine (52);
$N^1$-[(4-fluorophenyl)methyl]-4-chloro-5-methoxy-1,2-benzenediamine (53);
$N^1$-(2-furanylmethyl)-4-methoxy-1,2-benzenediamine (54);
$N^1$-(2-furanylmethyl)-5-methoxy-1,2-benzenediamine (55);
$N^1$-(2-pyridinylmethyl)-4-methoxy-1,2-benzenediamine (56);
$N^1$-(2-pyridinylmethyl)-5-methoxy-1,2-benzenediamine (57);
$N^2$-[(4-fluorophenyl)methyl]-6-methoxy-2,3-pyridinediamine (58);
$N^2$-(2-furanylmethyl)-6-methoxy-2,3-pyridinediamine (59); and
$N^2$-(2-pyridinylmethyl)-6-methoxy-2,3-pyridinediamine (60).

EXAMPLE 8

A mixture of 60 parts of 2-chloro-1H-benzimidazole, 58 parts of 1-(chloromethyl)-4-fluorobenzene, 42.5 parts of sodium carbonate, 0.1 parts of potassium iodide and 135 parts of N,N-dimethylformamide was stirred and heated overnight at 70° C. The reaction mixture was poured into water. The precipitated product was filtered off and dissolved in trichloromethane. The solution was dried, filtered and evaporated. The residue was crystallized from 2,2'-oxybispropane, yielding 62.5 parts of 2-chloro-1-(4-fluorophenylmethyl)-1H-benzimidazole (61).

EXAMPLE 9

A mixture of 8.35 parts of thiourea, 26 parts of 2-chloro-1-[(4-fluorophenyl)methyl]-1H-benzimidazole and 400 parts of ethanol was stirred and refluxed for 5 hours. The reaction mixture was evaporated. The residue was suspended in 2,2'-oxybispropane. The precipitated product was filtered off and crystallized from ethanol, yielding 6.1 parts of 1-[(4-fluorophenyl)methyl]-1H-benzimidazole-2-thiol; mp. 194.7° C. (62).

EXAMPLE 10

To a stirred solution of 6 parts of 1,2-dimethyl-1H-benzimidazole in 50 parts of dry pyridine were added dropwise 6.2 parts of benzoyl chloride at room temperature. Upon completion, stirring was continued for 2 hours at room temperature. The whole was evaporated. The residue was dissolved in 260 parts of dichloromethane. Water was added and the solution was treated with concentrate ammonium hydroxide. The dichloromethane layer was decanted, dried, filtered and evaporated. The residue was taken up twice in 45 parts of methylbenzene and the latter was evaporated each time, yielding 1-benzoyl-1,4-dihydro-4-[(1-methyl-1H-benzimidazol-2-yl)methyl]pyridine as an oily residue (63).

In a similar manner there was also prepared:
ethyl 4-[(1-methyl-1H-benzimidazol-2-yl)methyl]-1(4H)-pyridinecarboxylate as an oily residue (64).

EXAMPLE 11

A mixture of 9.7 parts of 4-fluoro-γ-(4-fluorophenyl)-benzenebutanoyl chloride, 4.1 parts of 2,6-dimethylpyridine and 68 parts of tetrahydrofuran was hydrogenated at normal pressure and at room temperature with 2 parts of palladium-on-charcoal catalyst 10%. After the calculated amount of hydrogen was taken up, the catalyst was filtered off and the filter was evaporated, yielding 8.5 parts of 4-fluoro-γ-(4-fluorophenyl)benzenebutanal (65).

EXAMPLE 12

To a stirred mixture of 26 parts of 1-ethyl-1,4-dihydro-5H-tetrazole-5-thione, 13.8 parts of potassium carbonate and 240 parts of 2-propanone were added dropwise 376 parts of 1,2-dibromoethane. Upon completion, stirring was continued overnight. The precipitate was filtered off and the filtrate was evaporated, yielding 45 parts (95%) of 5-[(2-bromoethyl)thio]-1-ethyl-1H-tetrazole as a residue (66).

EXAMPLE 13

To a stirred and cooled (0°–10° C.) mixture of 59 parts of 2-propanamine and 650 parts of dichloromethane were added dropwise 94.2 parts of 3-bromopropanoyl chloride. Upon completion, stirring was continued for 5 minutes. The whole was washed with water. The organic layer was separated, dried, filtered and evaporated. The residue was crystallized from a mixture of 2,2'-oxybispropane and hexane. The product was filtered off and dried, yielding 70 parts (73%) of 3-bromo-N-(1-methylethyl)propanamide; mp. 60° C. (67).

EXAMPLE 14

A mixture of 4.76 parts of 6-chloro-$N^4$-methyl-4,5-pyridinediamine, 26.6 parts of 1,1,1-triethoxyethane and 30 parts of acetic acid anhydride was stirred and refluxed for 3 hours. The reaction mixture was evaporated. The residue was crystallized from a mixture of hexane and methylbenzene. The product was filtered off and dried, yielding 5.3 parts (96.3%) of 6-chloro-8,9-dimethyl-9H-purine (68).

EXAMPLE 15

A mixture of 4.76 parts of 6-chloro-$N^4$methyl-4,5-pyrimidinediamine and 7.2 parts of urea was stirred and heated for 1 hour at 180° C. After cooling, the residue was suspended in water. The product was filtered off and dried, yielding 3.3 parts (60%) of 6-chloro-9-methyl-9H-purin-8-ol (69).

B. Preparation of Final Compounds

EXAMPLE 16

To 73 parts of hot (70° C.) polyphosphoric acid were added 27 parts of 1-(phenylmethyl)-4-piperidineacetic acid hydrochloride: temperature rose to 100° C. When the addition was complete, there were added portionwise 14 parts of 1,2-benzenediamine and stirring and heating was continued for 50 minutes at 170° C. The hot reaction mixture was poured into 300 parts of warm water. The acid solution was alkalized with a potassium hydroxide solution. The precipitated free base was filtered off, washed with water and extracted with trichloromethane. The extract was dried and evaporated. The solid residue was recrystallized from a mixture of 2-propanone and methanol, yielding 17 parts of 2-[[1-(phenylmethyl)-4-piperidinyl]-methyl]-1H-benzimidazole; mp. 221.5°–222° C. (compound 1).

In a similar manner there was also prepared:
2-[[1-(phenylmethyl)-4-piperidinyl]methyl]-1H-imidazo[4,5-c]pyridine; mp. 172.9° C. (2).

EXAMPLE 17

A mixture of 27.3 parts of O-methyl 1-(phenylmethyl)-4-piperidineethanimidate dihydrochloride, 14 parts of N-(2-furanylmethyl)-1,2-benzenediamine and 250 parts of acetic acid was stirred overnight at room temperature. The reaction mixture was evaporated and water was added to the residue. The whole was alkalized with sodium carbonate and extracted with 4-methyl-2-pentanone. The extract was dried, filtered and evaporated. The residue was crystallized from 1,1′-oxybisethane. The product was filtered off and dried, yielding 15.5 parts (57%) of 1-(2-furanylmethyl)-2-[[1-(phenylmethyl)-4-piperidinyl]methyl]-1H-benzimidazole; mp. 124.8° C. (3).

In a similar manner there were also prepared:
1-phenyl-2-[[1-(phenylmethyl)-4-piperidinyl]methyl]-1H-benzimidazole; mp. 141.6° C. (4); and
2-[[1-(phenylmethyl)-4-piperidinyl]methyl]-1-(3-pyridinylmethyl)-1H-benzimidazole; mp. 125.4° C. (5).

EXAMPLE 18

A mixture of 116.5 parts of O-ethyl 1-(phenylmethyl)-4-piperidineethanimidate hydrochloride, 61.5 parts of $N^1$-[(4-methylphenyl)methyl]-1,2-benzenediamine and 400 parts of methanol was stirred and refluxed overnight. Another portion of 40 parts of O-ethyl 1-(phenylmethyl)-4-piperidineethanimidate hydrochloride was added and stirring was continued for 4 hours at reflux. The reaction mixture was evaporated. Water was added to the residue. The solution was treated with ammonium hydroxide. The product was extracted with trichloromethane. The extract was dried, filtered and evaporated. The residue was crystallized from acetonitrile. The product was filtered off and dried, yielding 74.5 parts (63%) of 1-[(4-methylphenyl)methyl]-2-[[1-(phenylmethyl)-4-piperidinyl]methyl]-1H-benzimidazole; mp. 124.2° C. (6).

Following the same procedure and using equivalent amounts of the appropriate starting materials, there were also prepared:

2-[[1-(phenylmethyl)-4-piperidinyl]methyl]-1-(2-thienylmethyl)-1H-benzimidazole; mp. 156.3° C. (7);

3-[(4-fluorophenyl)methyl]-2-[[1-(phenylmethyl)-4-piperidinyl]-methyl]-3H-imidazo[4,5-b]pyridine; mp. 103.2°–105.8° C. (8);

2-[[1-(phenylmethyl)-4-piperidinyl]methyl]-3-(2-pyridinylmethyl)-3H-imidazo[4,5-b]pyridine; mp. 118.5°–120.9° C. (9);

3-(2-furanylmethyl)-2-[[1-(phenylmethyl)-4-piperidinyl]-methyl]-3H-imidazo[4,5-b]pyridine; mp. 118.5°–119.8° C. (10);

1-[(4-methoxyphenyl)methyl]-2-[[1-(phenylmethyl)-4-piperidinyl]-methyl]-1H-benzimidazole; mp. 95.2° C. (11);

2-[[1-(phenylmethyl)-4-piperidinyl]methyl]-3-(2-thienylmethyl)-3H-imidazo[4,5-b]pyridine; mp. 115.2° C. (12);

3-(phenylmethyl)-2-[[1-(phenylmethyl)-4-piperidinyl]-methyl]-3H-imidazo[4,5-b]pyridine (13);

1-(phenylmethyl)-2-[[1-(phenylmethyl)-4-piperidinyl]-methyl]-1H-benzimidazole; mp. 130° C. (14);

3-[(4-methylphenyl)methyl]-2-[[1-(phenylmethyl)-4-piperidinyl]-methyl]-3H-imidazo[4,5-b]pyridine (15);

3-[(4-methoxyphenyl)methyl]-2-[[1-(phenylmethyl)-4-piperidinyl]-methyl]-3H-imidazo[4,5-b]pyridine; mp. 83.4° C. (16);

1-[(4-fluorophenyl)methyl]-5-methoxy-2-[[1-(phenylmethyl)-4-piperidinyl]methyl]-1H-benzimidazole; mp. 112.6° C. (17);

1-(3-furanylmethyl)-2-[[1-(phenylmethyl)-4-piperidinyl]methyl]-1H-benzimidazole; mp. 102.0° C. (18);

1-[(4-fluorophenyl)methyl]-5-methyl-2-[[1-(phenylmethyl)-4-piperidinyl]methyl]-1H-benzimidazole (19);

1-[(4-fluorophenyl)methyl]-6-methoxy-2-[[1-(phenylmethyl)-4-piperidinyl]methyl]-1H-benzimidazole; mp. 110° C. (20);

5-fluoro-2-[[1-(phenylmethyl)-4-piperidinyl]methyl]-1H-benzimidazole; mp. 206.2° C. (21); and 1-[(5-methyl-2-furanyl)methyl]-2-[[1-(phenylmethyl)-4-piperidinyl]-methyl]-1H-benzimidazole; mp. 96° C. (22).

EXAMPLE 19

A mixture of 43 parts of 1-(phenylmethyl)-4-piperidineacetic acid hydrochloride, 31.5 parts of $N^3$-[(4-fluorophenyl)methyl]-2,3-pyridinediamine, 850 parts of phosphoryl chloride and 20 parts of N,N-diethylbenzenamine was stirred for 6 hours at reflux temperature. The reaction mixture was evaporated. Methylbenzene was added twice to the residue and the whole was each time evaporated. The final residue was poured into ice water and the whole was made alkaline with a dilute sodium hydroxide solution. The product was extracted twice with dichloromethane. The combined extracts were washed twice with water, dried, filtered and evaporated. The residue wa purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 30 parts (50.2%) of 1-[(4-fluorophenyl)methyl]-2-[[1-(phenylmethyl)-4-piperidinyl]methyl]-1H-imidazo[4,5-b]pyridine; mp. 140.7° C. (23).

In a similar manner there were also prepared:
1-[(4-fluorophenyl)methyl]-2-[[1-(phenylmethyl)-4-piperidinyl]-methyl]-1H-imidazo[4,5-c]pyridine; mp. 139.1° C. (24); and
3-[(4-fluorophenyl)methyl]-2-[[1-(phenylmethyl)-4-piperidinyl]-methyl]-3H-imidazo[4,5-c]pyridine; mp. 116.9° C. (25).

EXAMPLE 20

To a stirred mixture of 3.5 parts of ethyl 4-hydroxy-1-piperidinecarboxylate and 135 parts of N,N-dimethylformamide was added 1 part of a sodium hydride dispersion 50% and stirring was continued for 2 hours at room temperature. After the addition of 5.2 parts of 2-chloro-1-[(4-fluorophenyl)methyl]-1H-benzimidazole, the whole was further stirred overnight at room temperature. The reaction mixture was poured into ice water and the product was extracted with trichloromethane. The extract was dried, filtered and evaporated. The residue was crystallized from 2,2'-oxybispropane, yielding 2.5 parts (31.5%) of ethyl 4-[[1-[(4-fluorophenyl)methyl]-1H-benzimidazol-2-yl]oxy]-1-piperidinecarboxylate; mp. 94.0° C. (26).

In a similar manner there was also prepared:
methyl (cis+trans)-4-[[1-[(4-fluorophenyl)methyl]-1H-benzimidazol-2-yl]oxy]-3-methyl-1-piperidinecarboxylate (27).

EXAMPLE 21

To a stirred mixture of 1.5 parts of 1H-benzimidazole-2-thiol and 90 parts of N,N-dimethylformamide were added 0.8 parts of a sodium hydride dispersion 50%. Stirring was continiued for 1 hour. Then there were added 3.3 parts of 1-[(4-methylphenyl)sulfonyl]-4-piperidinol methanesulfonate(ester) and the whole was stirred overnight at room temperature. Stirring was continued overnight at 80° C. The reaction mixture was poured into water. The product was extracted with 4-methyl-2-pentanone. The extract was dried, filtered and evaporated. The residue was crystallized from acetonitrile, yielding 0.7 parts (18%) of 4-[(1H-benzimidazol-2-yl)thio]-1-[(4-methylphenyl)sulfonyl]-piperidine; mp. 194.8° C. (28).

In a similar manner there was also prepared:
4-[[1-[(4-fluorophenyl)methyl]-1H-benzimidazol-2-yl]thio]-1-[(4-methylphenyl)sulfonyl]piperidine; mp. 167.2° C. (29).

EXAMPLE 22

To a stirred and cooled (0° C.) mixture of 7.2 parts of 4-[[1-[(4-fluorophenyl)methyl]-1H-benzimidazol-2-yl]thio]-1-[(4-methylphenyl)sulfonyl]piperidine and 95 parts of dichloromethane was added dropwise a solution of 2.6 parts of 3-chlorobenzenecarboperoxoic acid in dichloromethane. Upon completion, stirring was continued for 2 hours at room temperature. The reaction mixture was washed with a sodium carbonate solution and with water. The organic layer was dried, filtered and evaporated. The residue was purified by column chromatography over silica gel using a mixture of trichloromethane and methanol (96:4 by volume) as eluent. The pure fractions were collected and the eluent was evaporated. The residue was crystallized from acetonitrile. The product was filtered off and dried, yielding 0.7 parts (9%) of 4-[[1-[(4-fluorophenyl)methyl]1H-benzimidazol-2-yl]sulfinyl]-1-[(4-methylphenyl)sulfonyl]piperidine; mp. 166.2° C. (30).

EXAMPLE 23

To a stirred solution of 7.2 parts of 4-[[1-[(4-fluorophenyl)-methyl]-1H-benzimidazol-2-yl]thio]-1-[(4-methylphenyl)sulfonyl]-piperidine in 195 parts of dichloromethane was added dropwise a solution of 7 parts of 3-chlorobenzenecarboperoxoic acid in 65 parts of dichloromethane. Upon completion, stirring was continued for 2 hours at room temperature. The whole was washed with a sodium carbonate solution and twice with water, dried, filtered and evaporated. The residue was crystallized from acetonitrile. The product was filtered off and dried, yielding 3 parts (40%) of 4-[[1-[(4-fluorophenyl)methyl]-1H-benzimidazol-2-yl]sulfonyl]-1-[(4-methylphenyl)sulfonyl]piperidine; mp. 214.7° C. (31).

EXAMPLE 24

A mixture of 16 parts of 1-benzoyl-1,4-dihydro-4-[(1-methyl-1H-benzimidazol-2-yl)methyl]pyridine and 160 parts of methanol was hydrogenated at normal pressure and at 50° C. with 5 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol (97.5:2.5 by volume) as eluent. The pure fractions were collected and the eluent was evaporated. The oily residue was crystallized from 14 parts of 1,1'-oxybisethane. The product was filtered off and dried, yielding 7.8 parts (58.5%) of 1-benzoyl-4-[(1-methyl-1H-benzimidazol-2-yl)methyl]pyridine; mp. 159.3° C. (32).

In a similar manner there was also prepared:
ethyl 4-[(1-methyl-1H-benzimidazol-2-yl)methyl]-1-piperidinecarboxylate; mp. 98.2° C. (33).

EXAMPLE 25

To a stirred mixture of 55 parts of 2-[[1-(phenylmethyl)-4-piperidinyl]methyl]-1H-benzimidazole and 450 parts of N,N-dimethylformamide were added 10.6 parts of a sodium hydride dispersion 50% and stirring was continued for 1 hour. Then there were added dropwise 26 parts of 1-(chloromethyl)-4-fluorobenzene (slightly exothermic reaction). Upon completion, stirring was continued overnight at room temperature. Water was added and the product was extracted with 4-methyl-2-pentanone. The extract was dried, filtered and evaporated. The solid residue was stirred in 1,1'-oxybisethane. The product was filtered off and dried, yielding 67.6 parts (90%) of 1-[(4-fluorophenyl)methyl]-2-[[1-(phenylmethyl)-4-piperidinyl]methyl]-1H-benzimidazole; mp. 127.5° C. (34).

Following the same procedure and using equivalent amounts of the appropriate starting materials, there were also prepared:
2-[[1-(phenylmethyl)-4-piperidinyl]methyl]-1-(4-thiazolylmethyl)-1H-benzimidazole; mp. 98.7°–105.8° C. (35); and
5(or 6)-fluoro-1-[(4-fluorophenyl)methyl]-2-[[1-(phenylmethyl)-4-piperidinyl]methyl]-1H-benzimidazole (36)

EXAMPLE 26

A mixture of 41 parts of 3-[(4-methoxyphenyl)methyl]-2-[[1-(phenylmethyl)-4-piperidinyl]methyl]-3H-imidazo[4,5-b]-pyridine and 480 parts of methanol was hydrogenated at normal pressure and at 50° C. with 5 parts of palladium-on-charcoal catalyst 10%. After the calculated amount of hydrogen was taken up, the catalyst was filtered off and the filtrate was evaporated, yielding 30 parts (89%) of 3-[(4-methoxyphenyl)methyl]-2-(4-piperidinylmethyl)-3H-imidazo[4,5-b]pyridine (37). In a similar manner there were also prepared:

2-(4-piperidinylmethyl)-1H-benzimidazole; mp. 195°–196.5° C. (38);
3-[(4-methylphenyl)methyl]-2-(4-piperidinylmethyl)-3H-imidazo[4,5-b]pyridine (39);
1-(phenylmethyl)-2-(4-piperidinylmethyl)-1H-benzimidazole.monohydrate; mp. 72.5° C. (40);
3-(phenylmethyl)-2-(4-piperidinylmethyl)-3H-imidazo[4,5-b]pyridine (41);
1-[(4-methylphenyl)methyl]-2-(4-piperidinylmethyl)-1H-benzimidazole ethanedioate (1:2). monohydrate; mp. 195.1° C. (42);
1-[(4-methoxyphenyl)methyl]-2-(4-piperidinylmethyl)-1H-benzimidazole ethanedioate (1:2). monohydrate; mp. 172.1° C. (43);
2-(4-piperidinylmethyl)-3-(2-pyridinylmethyl)-3H-imidazo[4,5-b]-pyridine (E)-2-butenedioate (2:3); mp. 191.1°–194.0° C. (44);
3-[(4-fluorophenyl)methyl]-2-(4-piperidinylmethyl)-3H-imidazo[4,5-b]-pyridine (E)-2-butenedioate (1:2); mp. 200.0°–201.2° C. (45);
1-phenyl-2-(4-piperidinylmethyl)-1H-benzimidazole; mp. 142.6° C. (46);
1-[(4-fluorophenyl)methyl]-2-(4-piperidinylmethyl)-1H-benzimidazole (E)-2-butenedioate (2:3); mp. 204.7° C. (47);
1-[(4-fluorophenyl)methyl]-2-(4-piperidinylmethyl)-1H-imidazo[4,5-b]-pyridine (E)-2-butenedioate(2:5); mp. 214.4° C. (48);
1-[(4-fluorophenyl)methyl]-2-(4-piperidinylmethyl)-1H-imidazo[4,5-c]-pyridineethanedioate(2:3).monohydrate; mp. 173.5° C. (49);
3-[(4-fluorophenyl)methyl]-2-(4-piperidinylmethyl)-3H-imidazo[4,5-c]-pyridine (E)-2-butenedioate(2:5); mp. 168.8° C. (50);
1-[(4-fluorophenyl)methyl]-5-methoxy-2-(4-piperidinylmethyl)-1H-benzimidazole dihydrochloride.monohydrate; mp. 214.1° C. (51);
1-[(4-fluorophenyl)methyl]-5-methyl-2-(4-piperidinylmethyl)-1H-benzimidazole (52); and
1-[(4-fluorophenyl)methyl]-6-methoxy-2-(4-piperidinylmethyl)-1H-benzimidazole (53).
5(or 6)-fluoro-1-[(4-fluorophenyl)methyl]-2-(4-piperidinylmethyl)-1H-benzimidazole (54).

EXAMPLE 27

A mixture of 4.95 parts of 4-[[1-[(4-fluorophenyl)methyl]-1H-benzimidazol-2-yl]thio]-1-[(4-methylphenyl)-sulfonyl]piperidine, 225 parts of a hydrobromic acid solution 48% in water and 5 parts of phenol was stirred and refluxed for 2 hours. The reaction mixture was evaporated and the residue as taken up in water and treated with a sodium hydroxide solution. The product was extracted with dichloromethane. The extract was dried, filtered and evaporated. The residue was purified by filtration over silica gel using a mixture of trichloromethane and methanol, saturated with ammonia (95:5 by volume) as eluent. The pure fractions were collected and the eluent was evaporated, yielding 3.4 parts (99%) of 1-[(4-fluorophenyl)methyl]-2-[(4-piperidinyl)thio]-1H-benzimidazole (55).

EXAMPLE 28

A mixture of 3.3 parts of 1-benzoyl-4-[(1-methyl-1H-benzimidazol-2-yl)methyl]piperidine, 1.7 parts of water and 40 parts of 2-propanol was stirred and refluxed for 30 hours. The reaction mixture was concentrated and the residue was shaken with 260 parts of dichloromethane. The formed precipitate was filtered off and the filtrate was washed thoroughly with 20 parts of water. The organic phase was dried, filtered and evaporated. The residue was converted into the ethanedioate salt in ethanol. The salt was filtered off and dried, yielding 3.4 parts (83%) of 1-methyl-2-(4-piperidinylmethyl)-1H-benzimidazole ethanedioate (1:2); mp. 219.7° C. (56).

EXAMPLE 29

To a stirred mixture of 76 parts of 2-[[1-(phenylmethyl)-4-piperidinyl]methyl]-1-(3-pyridinylmethyl)-1H-benzimidazole and 360 parts of methylbenzene were added dropwise 41 parts of ethyl carbonochloridate. Upon completion, stirring was continued for 2 hours at reflux. Another portion of 5 parts of ethyl carbonochloridate was added dropwise. Upon completion, stirring was continued for 2 hours at reflux. After cooling, the organic layer was washed with a sodium carbonate solution, dried, filtered and evaporated. The residue was purified by filtration over silica gel using a mixture of trichloromethane and methanol (90:10 by volume) as eluent. The pure fractions were collected and the eluent was evaporated, yielding 35.6 parts (50%) of ethyl 4-[[1-(3-pyridinylmethyl)-1H-benzimidazol-2-yl]methyl]-1-piperidinecarboxylate (57).

Following the same procedure and using equivalent amounts of the appropriate starting materials, there were also prepared:

methyl 4-[[1-(2-furanylmethyl)-1H-benzimidazol-2-yl]methyl]-1-piperidinecarboxylate (58);
ethyl 4-[[1-(2-thienylmethyl)-1H-benzimidazol-2-yl]methyl]-1-piperidinecarboxylate monohydrochloride; mp. 178.7° C. (59);
ethyl 4-[[1-(4-thiazolylmethyl)-1H-benzimidazol-2-yl]methyl]-1-piperidinecarboxylate monohydrochloride; mp. 197.4°–199.2° C. (60);
ethyl 4-[[1-(2-furanylmethyl)-1H-benzimidazol-2-yl]methyl]-1-piperidinecarboxylate as a residue (61);
ethyl 4-[[3-(2-thienylmethyl)-3H-imidazo[4,5-b]-2-yl]methyl]-1-piperidinecarboxylate as a residue (62); and
ethyl 4-[[3-(2-furanylmethyl)-3H-imidazo[4,5-b]pyridin-2-yl]-methyl]-1-piperidinecarboxylate (63).

EXAMPLE 30

A mixture of 68 parts of ethyl 4-[[1-(2-thienylmethyl)-1H-benzimidazol-2-yl]methyl]-1-piperidinecarboxylate monohydrochloride, 95 parts of potassium hydroxide, 800 parts of 2-propanol and 10 parts of water was stirred and refluxed for 6 hours. The reaction mixture was evaporated and water was added to the residue. The product was extracted with methylbenzene. The extract was dried, filtered and evaporated. The residue was crystallized from 1,1'-oxybisethane. The product was filtered off and dried, yielding 27 parts (49%) of 2-(4-piperidinylmethyl)-1-(2-thienylmethyl)-1H-benzimidazole; mp. 117.4° C. (64).

In a similar manner there were also prepared:
1-(2-furanylmethyl)-2-(4-piperidinylmethyl)-1H-benzimidazole (E)-2-butenedioate (2:3); mp. 219.6° C. (65);
1-[(4-fluorophenyl)methyl]-2-(4-piperidinyloxy)-1H-benzimidazole dihydrochloride; mp. 145.2° C. (66)
2-(4-piperidinylmethyl)-1-(3-pyridinylmethyl)-1H-benzimidazole as a residue (67);
3-(2-furanylmethyl)-2-(4-piperidinylmethyl)-3H-imidazo[4,5-b]pyridine ethanedioate (2:3). monohydrate; mp. 136.7° C. (68);
2-(4-piperidinylmethyl)-3-(2-thienylmethyl)-3H-imidazo[4,5-b]-pyridine (E)-2-butenedioate (2:3); mp. 209.6° C. (69);
cis-1-[(4-fluorophenyl)methyl]-2-[(3-methyl-4-piperidinyl)oxy]-1H-benzimidazole monohydrochloride.monohydrate mp. 143.7° C. (70); and trans-1-[(4-fluorophenyl)methyl]-2-[(3-methyl-4-piperidinyl)oxy]-1H-benzimidazole dihydrochloride; mp. 111.6° C. (71).

EXAMPLE 31

A mixture of 2 parts of ethyl 4-[[1-(4-thiazolylmethyl)-1H-benzimidazol-2-yl]methyl]-1-piperidinecarboxylate and 30 parts of a hydrobromic acid solution 48% was stirred and refluxed for 15 minutes. The reaction mixture was evaporated. The oily residue was crystallized from a mixture of ethanol and 2-propanone, yielding 2 parts of 2-(4-piperidinylmethyl)-1-(4-thiazolylmethyl)-1H-benzimidazole trihydrobromide; mp. 208.3°–226.3° C. (72).

EXAMPLE 32

To a stirred mixture of 72 parts of 1-(3-furanylmethyl)-2-[[1-(phenylmethyl)-4-piperidinyl]methyl]-1H-benzimidazole and 324 parts of methylbenzene were added dropwise 25.5 parts of ethyl carbonochloridate at reflux. Upon completion, stirring was continued for 2 hours at reflux temperature. After cooling, the mixture was washed twice with a sodium hydroxide solution 5%, once with water, dried, filtered and evaporated. This residue, together with 560 parts of 2-propanol, 69.9 parts of potassium hydroxide and 6 parts of water, was stirred and refluxed for 22 hours. The whole was cooled and evaporated. The residue was taken up in water. The product was extracted three times with dichloromethane. The combined extracts were washed twice with water, dried, filtered and evaporated. The residue was purified by column chromatography over silica gel using a mixture of trichloromethane, methanol and ammonium hydroxide (90:10:1 by volume) as eluent. The pure fractions were collected and the eluent was evaporated. The residue was stirred in 2-propanone. The product was filtered off and dried, yielding 28.0 parts (49.8%) of 1-(3-furanylmethyl)-2-(4-piperidinylmethyl)-1H-benzimidazole; mp. 180° C. (73).

In a similar manner there was also prepared:
1-[(5-methyl-2-furanyl)methyl]-2-(4-piperidinylmethyl)-1H-benzimidazole; mp. 90° C. (74).

EXAMPLE 33

To a stirred mixture of 10.2 parts of 1-[(4-fluorophenyl)methyl]-2-[(4-piperidinyl)thio]-1H-benzimidazole, 3.1 parts of N,N-diethylethanamine and 130 parts of dichloromethane was added dropwise a solution of 5.12 parts of (phenylmethyl) carbonochloridate in 65 parts of dichloromethane. Upon completion, stirring was continued for 1 hour at room temperature. The reaction mixture was washed with water. The organic layer was dried, filtered and evaporated, yielding 14.3 parts of (phenylmethyl) 4-[[1-[(4-fluorophenyl)methyl]-1H-benzimidazol-2-yl]thio]-1-piperidinecarboxylate as a residue (75).

In a similar manner there were also prepared:
(phenylmethyl) 4-[[1-[(4-fluorophenyl)methyl]-1H-benzimidazol-2-yl]sulfonyl]-1-piperidinecarboxylate.; mp. 147.3° C. (76); and 1-[(4-fluorophenyl)methyl]-2-(4-piperidinylsulfonyl)-1H-benzimidazole.; mp. 133.5° C. (77).

EXAMPLE 34

A solution of 22.3 parts of 1-[(4-fluorophenyl)methyl]-5-methoxy-2-(4-piperidinylmethyl)-1H-benzimidazole dihydrochloride.monohydrate in 75 parts of a hydrobromic acid solution 48% in water was stirred and refluxed for 18 hours. The whole was slightly cooled and evaporated. The residue was dissolved in water. The solution was treated with an ammonium hydroxide solution. The product was extracted three times with trichloromethane. The combined organic layers were washed with water, dried, filtered and evaporated, yielding 15.7 parts (92%) of 1-[(4-fluorophenyl)methyl]-2-(4-piperidinylmethyl)-1H-benzimidazol-5-ol; mp. 210° C. (78).

In a similar manner there was also prepared:
1-[(4-fluorophenyl)methyl]-2-(4-piperidinylmethyl)-1H-benzimidazol-6-ol (79).

EXAMPLE 35

To a stirred mixture of 19.9 parts of 1-[(4-fluorophenyl)-methyl]-2-(4-piperidinyloxy)-1H-benzimidazole dihydrochloride, 12.2 parts of N,N-diethylethanamine and 65 parts of dichloromethane was added a solution of 6.5 parts of 2-furanacetic acid and 20.6 parts of N,N-methanetetraylbis[cyclohexanine] in 130 parts of dichloromethane. The whole was stirred over weekend at room temperature. The reaction mixture was filtered and the filtrate was poured into water. The organic phase was separated, dried, filtered and evaporated. The residue was purified by column chromatography over silica gel using a mixture of trichloromethane and methanol (95:5 by volume) as eluent. The pure fractions were collected and the eluent was evaporated. The residue was crystallized from 1,1'-oxybisethane. The product was filtered off and dried, yielding 5.3 parts (25%) of 4-[[1-[(4-fluorophenyl)methyl]-1H-benzimidazol-2-yl]oxy]-1-[2-(2-fuanyl)acetyl]piperidine; mp. 128.7° C. (80).

EXAMPLE 36

A mixture of 2 parts of poly(oxymethylene), 3.5 parts of 1-[(4-methylphenyl)methyl]-2-(4-piperidinylmethyl)-1H-benzimidazole, 1 part of a solution of thiophene in ethanol 4% and 120 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was taken up in water. The product was extracted with dichloromethane. The organic layer was dried, filtered and evaporated. The residue was converted into the (E)-2-butenedioate salt in ethanol. The salt was filtered off and dried, yielding 3 parts (536%) of 1-[(4-methylphenyl)methyl]-2-[(1-methyl-4-piperidinyl)methyl]-1H-benzimidazole (E)-2-butenedioate (2:3); mp. 188.9° C. (81).

In a similar manner there wre also prepared:

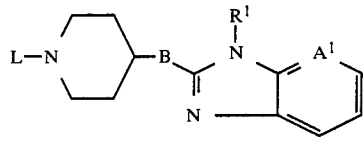

| No. | L | R¹ | A¹ | B | salt/base | mp. °C. |
|---|---|---|---|---|---|---|
| 82 | CH₃ | 4-F—C₆H₄CH₂ | CH | CH₂ | * | 193.1 |
| 83 | (CH₃)₂CH | 4-F—C₆H₄CH₂ | CH | CH₂ | * | 165.7 |
| 84 | (CH₃)₂CH | 4-F—C₆H₄CH₂ | CH | O | * | 210.5 |
| 85 | CH₃ | 4-F—C₆H₄CH₂ | CH | O | * | 161.0 |
| 86 | CH₃ | 2-furanylmethyl | CH | CH₂ | * | 178.4 |
| 87 | (CH₃)₂CH | 2-furanylmethyl | CH | CH₂ | HCl | 206.0 |
| 88 | CH₃ | 4-thiazolylmethyl | CH | CH₂ | ** | 146.9 |
| 89 | (CH₃)₂CH | 4-F—C₆H₄CH₂ | N | CH₂ | *** | 163.0 |
| 90 | CH₃ | 4-F—C₆H₄CH₂ | N | CH₂ | *** | 158.2 |
| 91 | CH₃ | H | CH | CH₂ | base | oil |
| 92 | (4-F—C₆H₄)₂CH(CH₂)₃ | H | CH | CH₂ | *** | 212.5 |
| 93 | CH₃ | C₆H₅CH₂ | CH | CH₂ | base | 96.1 |
| 94 | (CH₃)₂CH | C₆H₅CH₂ | CH | CH₂ | *** | 194.2 |
| 95 | (CH₃)₂CH | CH₃ | CH | CH₂ | *** | 116.3 |
| 96 | CH₃ | 4-F—C₆H₄CH₂ | CH | S | *** | 139.0 |
| 97 | C₆H₅CH₂—N | 4-F—C₆H₄CH₂ | CH | CH₂ | 2HCl H₂O | >300 (dec.) |
| 98 | cyclohexyl | 4-F—C₆H₄CH₂ | N | CH₂ | *** | 163.9 |
| 99 | cyclohexyl | 4-F—C₆H₄CH₂ | CH | CH₂ | *** | 172.1 |

*(E)—2-butenedioate salt (2:3)
**ethanedioate (1:2) salt.monohydrate
***ethanedioate (1:2)

In a similar manner there was also prepared:
1-[(4-fluorophenyl)methyl]-2-[[1-(1-methylethyl)-4-piperidinyl[-methyl]-1H-imidazo[4,5-c]pyridine; mp. 115.9° C. (100).

EXAMPLE 37

A mixture of 7.9 parts of 3-[(4-fluorophenyl)methyl]-2-(4-piperidinylmethyl)-3H-imidazo[4,5-b]pyridine dihydrochloride, 5.3 parts of sodium carbonate and 120 parts of 4-methyl-2-pentanone was stirred and refluxed for 15 minutes using a water separator. 3.2 Parts of 2-ethenylpyridine were added at reflux temperature and stirring was continued for 3 hours at reflux using a water separator. Then there were added 3.2 parts of 2-ethenylpyridine and the whole was stirred and refluxed for 19.50 hours using a water separator. After cooling, the salts were filtered off and the filtrate was washed with water, dried, filtered and evaporated. The residue was converted into the ethanedioate salt in 2-propanone. The salt was filtered off and crystallized from a mixture of ethanol and 2-propanone, yielding 2.5 parts (17%) of 3-[(4-fluorophenyl)methyl]-2-[[1-[2-pyridinyl)ethyl]-4-piperidinyl]methyl]-3H-imidazo[4,5-b]-pyridine ethanedioate (1:3); mp. 143.1° C. (101).

In a similar manner there were also prepared: 4-[4-[[1-[(4-fluorophenyl)methyl]-1H-benzimidazol-2-yl]methyl]-1-piperidinyl]-2-butanone ethanedioate(2:5).; mp. 163.4° C. (102); and 1-[(4-fluorophenyl)methyl]-2-[[1-[2-(2-pyridinyl)ethyl]-4-piperidinyl]-methyl]-1H-benzimidazole ethanedioate(1:3). monohydrate; mp. 138.3° C. (103).

EXAMPLE 38

1.8 Parts of gaseous oxirane were bubbled through a stirred mixture of 8.5 parts of 1-[(4-fluorophenyl)methyl]-2-[(4-piperidinyl)thio]-1H-benzimidazole and 120 parts of methanol. Stirring was continued overnight at room temperature. The reaction mixture was evaporated. The residue was purified by column chromatography over silica gel using a mixture of trichloromethane and methanol (95:5 by volume) as eluent. The pure fractions were collected and the eluent was evaporated. The residue was converted into the ethanedioate salt in 2-propanone. The salt was filtered off and dried, yielding 5.5 parts (48%) of 4-[[1-[(4-fluorophenyl)-methyl]-1H-benzimidazol-2-yl]thio]-1-piperidineethanol ethanedioate (1:1); mp. 165.2° C. (104).

In a similar manner there were also prepared:
4-[[1-[(4-fluorophenyl)methyl]-1H-benzimidazol-2-yl]oxy]-1-piperidineethanol (E)-2-butenedioate (2:3); mp. 156.1° C. (105);
4-[(1-phenyl-1H-benzimidazol-2-yl)methyl]-1-piperidineethanol; mp. 112.2° C. (106);
4-[[1-[(4-fluorophenyl)methyl]-1H-benzimidazol-2-yl]methyl]-1-piperidineethanol; mp. 135.6° C. (107);
4-[[1-(2-furanylmethyl)-1H-benzimidazol-2-yl]methyl]-1-piperidineethanol (108);
4-[[1-(4-thiazolylmethyl)-1H-benzimidazol-2-yl]methyl]-1-piperidineethanol ethanedioate (2:5); mp. 123.5°–137.8° C. (109);
4-[[1-[(4-methoxyphenyl)methyl]-1H-benzimidazol-2-yl]methyl]-1-piperidineethanol ethanedioate (1:2); mp. 148.5° C. (110);
4-[[3-(2-pyridinylmethyl)-3H-imidazo[4,5-b]pyridin-2-yl]methyl]-1-piperidineethanol (E)-2-butenedioate (2:3); mp. 151.0° C. (111);
4-[[1-(phenylmethyl)-1H-benzimidazol-2-yl]methyl-1-piperidineethanol; mp. 136.9° C. (112);
4-[[1-[(4-methylphenyl)methyl]-1H-benzimidazol-2-yl]methyl]-1-piperidineethanol ethanedioate (1:2); mp. 167.7° C. (113);
4-[[3-[(4-fluorophenyl)methyl]-3H-imidazo[4,5-b]pyridin-2-yl]methyl]-α-[(1-naphthalenyloxy)methyl]-1-piperidineethanol (E)-2-butenedioate (2:3); mp. 144.7° C. (114);
4-[[3-[(4-fluorophenyl)methyl]-3H-imidazo[4,5-b]pyridin-2-yl]methyl]-1-piperidineethanol; mp. 116.8° C. (115); and 4-[[1-[(4-fluorophenyl)methyl]-1H-benzimidazol-2-yl]methyl]-α-[(2-naphthalenyloxy)methyl]-1-piperidineethanol ethanedioate(1:2); mp. 152.9° C. (116).

EXAMPLE 39

A mixture of 7.9 parts of 3-[(4-fluorophenylmethyl]-2-(4-piperidinylmethyl)-3H-imidazo[4,5-b]pyridine dihydrochloride, 8.5 parts of sodium carbonate and 120 parts of 4-methyl-2-pentanone was stirred and refluxed for 30 minutes using a water separator. 7.8 Parts of 2-thiopheneethanol methanesulfonate (ester) were added and the whole was stirred and refluxed for 4 hours using a water separator. After cooling, the salts were filtered off, washed with 4-methyl-2-pentanone and the filtrate was washed with water. The organic layer was dried, filtered and evaporated. The residue was converted into the hydrochloride salt in 2-propanol and 2-propanone. The salt was filtered off and dried in vacuo at 60° C., yielding 8.0 parts (76%) of 3-[(4-fluorophenyl)methyl]-2-[[1-[2-thienyl)-ethyl]-4-piperidinyl]-methyl]-3H-imidazo[4,5-b]pyridine dihydrochloride. monohydrate; mp. 210.8° C. (117).

Following the same procedure and using equivalent amounts of the appropriate starting materials, there was also prepared: 1-[(4-fluorophenyl)methyl]-2-[[1-[2-(2-thienyl)ethyl]-4-piperidinyl]-methyl]-1H-benzimidazole ethanedioate (1:2).hemihydrate; mp. 142.0° C. (118).

EXAMPLE 40

A mixture of 6.5 parts of 1-[(4-fluorophenyl)methyl]-2-(4-piperidinylmethyl)-1H-benzimidazole, 4.2 parts of sodium carbonate and 120 parts of 4-methyl-2-pentanone was stirred and refluxed for 30 minutes using a water separator. 5.2 Parts of 1-(3-chloropropoxy)-4-fluorobenzene were added at reflux temperature and stirring was continued for 3 hours at this temperature using a water separator. After cooling to room temperature, the salts were filtered off and the filtrate was washed twice with water, dried, filtered and evaporated. The residue was converted into the ethanedioate salt in 2-propanone. The salt was filtered off, washed with 2-propanone and crystallized from methanol. The product was filtered off and dried in vacuo at 80° C., yielding 7 parts (53%) of 2-[[1-[3-(4-fluorophenoxy)-propyl]-4-piperidinyl]methyl]-1-[(4-fluorophenyl)methyl]-1H-benzimidazole ethanedioate (1:2); mp. 186.7° C. (119).

Following the same procedure and using equivalent amounts of the appropriate starting materials, there were also prepared:

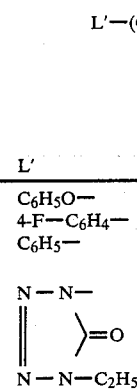

| No. | L' | s | R¹ | A¹ | salt/base | mp. (°C.) |
|---|---|---|---|---|---|---|
| 120 | $C_6H_5O$— | 2 | H | CH | base | 143–144.5 |
| 121 | 4-F—$C_6H_4$— | 3 | H | CH | base | 140–144 |
| 122 | $C_6H_5$— | 2 | H | CH | base | 183–187 |
| 123 | 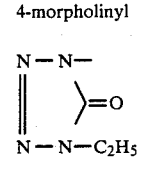 | 2 | 4-F—$C_6H_4CH_2$ | CH | $2(COOH)_2$ | 127.6 |
| 124 | 4-morpholinyl | 2 | 4-F—$C_6H_4CH_2$ | N | $2(COOH)_2$ | 205.2 |
| 125 | (same as 123) | 2 | 4-F—$C_6H_4CH_2$ | N | $2(COOH)_2$ | 182.2 |
| 126 | $C_2H_5O$— | 2 | 4-F—$C_6H_4CH_2$ | N | 2HCl $H_2O$ | 180.0 |
| 127 | 4-F—$C_6H_4C(O)$— | 3 | 4-F—$C_6H_4CH_2$ | N | 2HCl $H_2O$ | 167.1 |
| 128 | $(CH_3)_2CHNHC(O)$— | 1 | 4-F—$C_6H_4CH_2$ | N | $(COOH)_2$ | 227.5 |
| 129 | $C_6H_5S$— | 2 | 4-F—$C_6H_4CH_2$ | CH | $2(COOH)_2$ | 173.5 |
| 130 | $C_6H_5SO_2$ | 2 | 4-F—$C_6H_4CH_2$ | CH | $2(COOH)_2$ | 193.0 |
| 131 | 4-morpholinyl | 2 | 4-F—$C_6H_4CH_2$ | CH | * | 207.7 |
| 132 | 1H—benzimidazol-2-yl | 1 | 4-F—$C_6H_4CH_2$ | N | $3(COOH)_2$ | 165.5 |
| 133 | $C_2H_5O$— | 2 | 4-F—$C_6H_4CH_2$ | CH | *** | 113.0 |
| 134 | $(CH_3)_2CHNHC(O)$— | 1 | 4-F—$C_6H_4CH_2$ | CH | *** | 151.0 |
| 135 | 4-F—$C_6H_4O$— | 3 | 4-F—$C_6H_4CH_2$ | N | $2(COOH)_2$ | 157.1 |
| 136 | 1H—benzimidazol-2-yl | 1 | 4-F—$C_6H_4CH_2$ | CH | ** | 205.1 |
| 137 | 2,3-dihydro-1,4-benzodioxin-2-yl | 1 | 4-F—$C_6H_4CH_2$ | N | $2(COOH)_2$ | 176.8 |

*(E)—2-butenedioate salt (1:2)
**(E)—2-butenedioate salt (2:3)
***ethanedioate salt (2:5)

In a similar manner there was also prepared:

2-[[1-[[1-(1H-benzimidazol-2-ylmethyl)-1H-benzimidazol-2-yl]methyl]-4-piperidinyl]methyl]-3-[(4-fluorophenyl)methyl]-3H-imidazo[4,5-b]-pyridine; mp. 247.7° C. (138).

EXAMPLE 41

A mixture of 3.16 parts of 1-(3-chloropropyl)-1,3-dihydro-2H-benzimidazol-2-one, 4.4 parts of 1-(2-furanylmethyl)-2-(4-piperidinylmethyl)-1H-benzimidazole, 2 parts of sodium hydrogen carbonate and 80 parts of ethanol was stirred and refluxed for 32 hours. The reaction mixture was cooled and filtered over Hyflo. The filtrate was evaporated. The residue was purified by column chromatography over silica gel using a mixture of trichloromethane and methanol (90:10 by volume) as eluent. The pure fractions were collected and the eluent was evaporated. The residue was converted into the ethanedioate salt in methanol. The salt was filtered off and dried, yielding 4.2 parts (43%) of 1-[3-[4-[[1-(2-furanylmethyl)-1H-benzimidazol-2-yl]methyl]-1-piperidinyl]propyl]-1,3-dihydro-2H-benzimidazol-2-one ethanedioate (1:2); mp. 214.7°–218.4° C. (139).

In a similar manner there were also prepared:
1-[3-[4-[[1-[(4-fluorophenyl)methyl]-1H-benzimidazol-2-yl]oxy]-1-piperidinyl]propyl]-1,3-dihydro-2H-benzimidazol-2-one; mp. 186.7° C. (140);
3-[2-[4-[[1-[(4-fluorophenyl)methyl]-1H-benzimidazol-2-yl]oxy]-1-piperidinyl]ethyl]-2,4(1H,3H)quinazolinedione; mp. 190.4° C. (141).
3-[(4-fluorophenyl)methyl]-2-[[1-(2-propenyl)-4-piperidinyl]methyl]-3H-imidazo-[4,5-b]pyridine dihydrochloride.monohydrate; mp. 166.9° C. (142);
4-[[3-[(4-fluorophenyl)methyl]-3H-imidazo[4,5-b]pyridin-2-yl]methyl]-N-(1-methylethyl)-1-piperidinepropanamide; mp. 134.0° C. (143);
1-[(4-fluorophenyl)methyl]-2-[[1-(2-propenyl)-4-piperidinyl]methyl]-1H-benzimidazole ethanedioate(1:2); mp. 119.0° C. (144);
4-[[1-[(4-fluorophenyl)methyl]-1H-benzimidazol-2-yl]methyl]-N-(1-methylethyl)-1-piperidinepropanamide (E)-2-butenedioate(2:3); mp. 138.3° C. (145);
3-[(4-fluorophenyl)methyl]-2-[[1-[2-(phenylsulfonyl)ethyl]-4-piperidinyl]methyl]-3H-imidazo-[4,5-b]pyridine ethanedioate(2:3); mp. 159.0° C. (146); and
3-[(4-fluorophenyl)methyl]-2-[[1-[2-(phenylthio)ethyl]-4-piperidinyl]methyl]-3H-imidazo[4,5-b]pyridine ethanedioate(1:2); mp. 190.0° C. (147).

EXAMPLE 42

A mixture of 9.3 parts of 2-iodoacetamide, 20.0 parts of 3-[(4-fluorophenylmethyl)]-2-(4-piperidinylmethyl)-3H-imidazo[4,5-b]pyridine dihydrochloride, 17.0 parts of sodium hydrogen carbonate and 200 parts of ethanol was stirred for 3 hours at at reflux temperature. The salts were filtered off and the filtrate was evaporated. The residue was purified by column chromatography over silica gel using a mixture of trichloromethane, methanol and ammonium hydroxide (90:9:1 by volume) as eluent. The pure fractions were collected and the eluent was evaporated. The residue was crystallized from a mixture of 2,2'-oxybispropane and 2-propanone. The product was filtered off and dried in vacuo at 60° C., yielding 8.5 parts (44.5%) of 4-[[3-[(4-fluorophenyl)methyl]-3H-imidazo[4,5-b]pyridin-2-yl]methyl]-1-piperidineacetamide; mp. 153.4° C. (148).

In a similar manner there was also prepared:
4-[[1-[(4-fluorophenyl)methyl]-1H-benzimidazol-2-yl]methyl]-1-piperidineacetamide; mp. 187.5° C. (149).

EXAMPLE 43

A mixture of 5.55 parts of N-(dihydro-3,3-diphenyl-2(3H)-furanylidene)-N-methylmethanaminium bromide, 4.85 parts of 1-[(4-fluorophenyl)methyl]-2-(4-piperidinylmethyl)-1H-benzimidazole, 2 parts of sodium carbonate and 90 parts of N,N-dimethylformamide was stirred overnight at 70° C. The reaction mixture was poured into water. The product was extracted with 4-methyl-2-pentanone. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 1.8 parts (20%) of 4-[[1-[(4-fluorophenyl)methyl]-1H-benzimidazol-2-yl]methyl]-N,N-dimethyl-α,α-diphenyl-1-piperidinebutanamide; mp. 151.4° C. (150).

EXAMPLE 44

A mixture of 6.62 parts of 6-(2-bromoethyl)-3,7-dimethyl-5H-thiazolo[3,2-a]pyrimidin-5-one monohydrobromide, 4.45 parts of 3-(2-furanylmethyl)-2-(4-piperidinylmethyl)-3H-imidazo[4,5-b]-pyridine, 4.8 parts of sodium carbonate and 90 parts of N,N-dimethylformamide was stirred and heated overnight at 70° C. The reaction mixture was poured into water. The product was extracted with 4-methyl-2-pentanone. The extract was dried, filtered and evaporated. The residue was purified by column chromatography over silica gel using a mixture of trichloromethane and methanol (90:10 by volume) as eluent. The pure fractions were collected and the eluent was evaporated. The residue was converted into the hydrochloride salt in ethanol. The salt was filtered off and dried, yielding 4.5 parts (48%) of 6-[2-[4-[[3-(2-furanylmethyl)-3H-imidazo[4,5-b]pyridin-2-yl]methyl]-1-piperidinyl]ethyl]-3,7-dimethyl-5H-thiazolo[3,2-a]pyrimidin-5-one trihydrochloride.monohydrate; mp. 248.6° C. (151).

Following the same procedure and using equivalent amounts of the appropriate starting materials, there were also prepared:

$$\text{L}'-(\text{CH}_2)_s-\text{N}\underset{\phantom{x}}{\bigcirc}-\text{B}\overset{\displaystyle \phantom{x}}{\underset{\displaystyle N}{=}}\text{C}-\text{N}\overset{\displaystyle \text{CH}-\text{R}^{1-a}}{\underset{\displaystyle \phantom{x}}{\bigg|}}\text{A}^1$$

| No. | L' | s | B | $R^{1-a}$ | $A^1$ | salt/base | mp.(°C.) |
|---|---|---|---|---|---|---|---|
| 152 | 2-(NH-C(=O))-phenyl-N- | 3 | $CH_2$ | 2-furanyl- | N | 1½(COOH)$_2$ | 206.2 |
| 153 | 2-(NH-C(=O))-phenyl-N- | 3 | $CH_2$ | 4-F—C$_6$H$_4$— | N | * | 132.6 |
| 154 | 2-(NH-C(=O))-phenyl-N- | 3 | $CH_2$ | 4-CH$_3$O—C$_6$H$_4$— | CH | ** | 168.7 |
| 155 | 2-(NH-C(=O))-phenyl-N- | 3 | $CH_2$ | C$_6$H$_5$— | CH | 2(COOH)$_2$ | 211.1 |
| 156 | 2-(NH-C(=O))-phenyl-N- | 3 | $CH_2$ | C$_6$H$_5$— | N | 3(COOH)$_2$ | 147.5 |
| 157 | quinazolinedione-N- | 3 | $CH_2$ | 4-F—C$_6$H$_4$— | CH | base | 186.6 |
| 158 | thiazine-pyrimidinone fused | 2 | $CH_2$ | 4-F—C$_6$H$_4$— | CH | *** | 192.6 |
| 159 | quinazolinedione-N- | 3 | $CH_2$ | 2-furanyl- | CH | base | 179.1 |
| 160 | thiazine-pyrimidinone fused | 2 | $CH_2$ | 4-F—C$_4$H$_6$— | CH | ** | 194.9 |
| 161 | chromen-2-one- | 2 | $CH_2$ | 4-F—C$_6$H$_4$— | CH | *** | 174.7 |

-continued

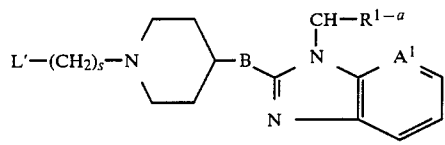

| No. | L¹ | s | B | R¹⁻ᵃ | A¹ | salt/base | mp.(°C.) |
|---|---|---|---|---|---|---|---|
| 162 | (S,N,CH₃,N,O thiazine-dione) | 2 | $CH_2$ | 4-F—$C_6H_4$— | CH | ** | 186.9 |
| 163 | (S,N,CH₃,N,O thiazine-dione) | 2 | $CH_2$ | 2-furanyl | CH | 2(COOH)₂2H₂O | 164.7 |
| 164 | (H,N,O,N,O uracil) | 2 | $CH_2$ | 4-F—$C_6H_4$— | CH | base | 168.6 |
| 165 | (coumarin) | 2 | $CH_2$ | 2-furanyl- | CH | 2HCl.H₂O | 240.1 |
| 166 | (S,N,CH₃,N,O thiazine-dione) | 2 | $CH_2$ | 2-furanyl- | CH | 3HCl.2H₂O | 197.4 |
| 167 | (S,N,CH₃,N,O thiazine-dione) | 2 | $CH_2$ | 2-furanyl | CH | 3HCl.2H₂O | 215.8 |
| 168 | (S,N,CH₃,N,O thiazine-dione) | 2 | $CH_2$ | 2-furanyl | N | 3HCl.H₂O | 250.2 |
| 169 | (H,N,O,N,O quinazolinedione) | 3 | $CH_2$ | 2-furanyl | N | base | 198.2 |
| 170 | ($CH_3$,N,O,N,O quinazolinedione) | 2 | $CH_2$ | 2-furanyl | N | 2HCl.H₂O | 227.4 |

-continued
L'—(CH2)s—N⟨piperidine⟩—B=N—CH—R¹⁻ᵃ / N / A¹ (with CH group)
| No. | L' | s | B | R¹⁻ᵃ | A¹ | salt/base | mp.(°C.) |
|-----|-----|---|-----|-------|-----|-----------|----------|
| 171 |  | 2 | CH₂ | 2-furanyl | N | base | 199.2 |
| 172 | 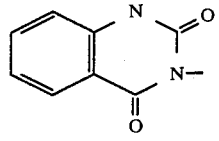 | 3 | CH₂ | 4-F—C₆H₄— | N | base | 183.6 |
| 173 | 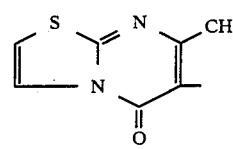 | 2 | CH₂ | 2-furanyl- | N | 3HCl.2H₂O | 186.8 (dec.) |
| 174 | 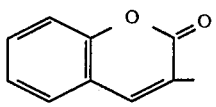 | 2 | CH₂ | 2-furanyl- | N | 2HCl.H₂O | 204.3 (dec.) |
| 175 | 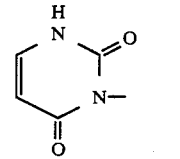 | 2 | CH₂ | 2-furanyl | CH | base | 175.2 |
| 176 | 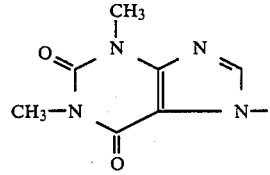 | 2 | CH₂ | 2-furanyl | N | 2HCl.H₂O | 182.1 |
| 177 | 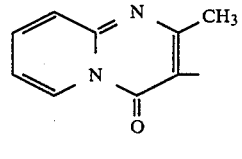 | 2 | CH₂ | 4-F—C₆H₄— | N | 3HCl.H₂O | 229.7 |
| 178 | 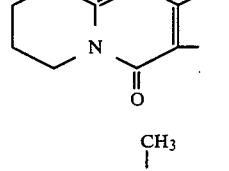 | 2 | CH₂ | 2-furanyl- | N | *** | 183.6 |
| 179 | 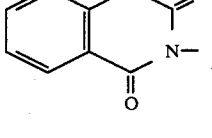 | 2 | CH₂ | 4-F—C₆H₄— | N | 2HCl.H₂O | 240.9 |

-continued

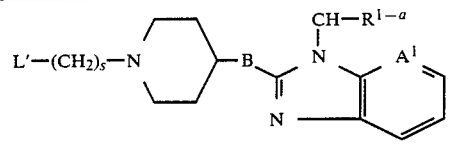

| No. | L' | s | B | R$^{1-a}$ | A$^1$ | salt/base | mp.(°C.) |
|---|---|---|---|---|---|---|---|
| 180 | ![pyridinyl-enone] | 2 | CH$_2$ | 2-furanyl- | N | 2½(COOH)$_2$·H$_2$O | 163.1 |
| 181 | ![tetrazole-SMe with CH$_2$CH$_3$] | 2 | CH$_2$ | 4-F—C$_6$H$_4$— | CH | 2½(COOH)$_2$ | 161.0 |
| 182 | ![thiazolyl-CH$_3$] | 2 | CH$_2$ | 4-F—C$_6$H$_4$— | CH | base | 101.2 |
| 183 | ![pyrimidinyl] | 1 | CH$_2$ | 4-F—C$_6$H$_4$— | CH | base | 164.3 |
| 184 | ![pyridinyl] | 1 | CH$_2$ | 4-F—C$_6$H$_4$— | CH | 3(COOH)$_2$ | 161.4 |
| 185 | ![coumarin] | 2 | O | 4-F—C$_6$H$_4$— | CH | 2HCl | 194.8 |
| 186 | ![quinazolinedione] | 2 | CH$_2$ | 2-thienyl- | CH | base | 196.0 |
| 187 | ![quinazolinedione] | 2 | CH$_2$ | 4-thiazolyl- | CH | base | 210.6 |

*(E)—2-butenedioate salt (2:3)·monohydrate
**(E)—2-butenedioate salt (2:3)
***(E)—2-butenedioate salt (1:2)

In a similar manner there were also prepared:

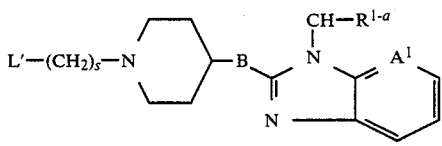

| Comp. No. | L' | s | B | R$^{1-a}$ | A$^1$ | base or salt | mp. °C. |
|---|---|---|---|---|---|---|---|
| 188 | (4-F—C$_6$H$_4$)$_2$—CH— | 3 | O | 4-F—C$_6$H$_4$— | CH | 2HNO$_3$ | 140.3 |

-continued

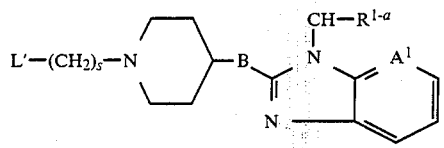

| Comp. No. | L' | s | B | $R^{1-a}$ | $A^1$ | base or salt | mp. °C. |
|---|---|---|---|---|---|---|---|
| 189 | 4-CH$_3$O—C$_6$H$_4$— | 2 | CH$_2$ | 2-furanyl- | N | 2(COOH)$_2$ | 159.4 |
| 190 | 4-CH$_3$O—C$_6$H$_4$— | 2 | O | 4-F—C$_6$H$_4$— | CH | * | 155.2 |
| 191 | 4-CH$_3$O—C$_6$H$_4$— | 2 | CH$_2$ | 4-CH$_3$OC$_6$H$_4$— | CH | ** | 223.8 |
| 192 | (4-F—C$_6$H$_4$)$_2$—CH— | 3 | CH$_2$ | 2-furanyl- | N | 2(COOH)$_2$ | 144.1 |
| 193 | (4-F—C$_6$H$_4$)$_2$—CH— | 3 | CH$_2$ | 2-pyridinyl- | N | 2(COOH)$_2$ | 134.9 |
| 194 | (4-F—C$_6$H$_4$)$_2$—CH— | 3 | CH$_2$ | 4-CH$_3$OC$_6$H$_4$— | CH | 2(COOH)$_2$ | 126.7 |
| 195 | (4-F—C$_6$H$_4$)$_2$—CH— | 3 | CH$_2$ | 4-F—C$_6$H$_4$— | N | 2(COOH)$_2$ | 182.2 |
| 196 | (4-F—C$_6$H$_4$)$_2$—CH— | 3 | CH$_2$ | C$_6$H$_5$— | CH | 2½(COOH)$_2$ | 140.4 |
| 197 | (4-F—C$_6$H$_4$)$_2$—CH— | 3 | CH$_2$ | C$_6$H$_5$— | N | 2(COOH)$_2$ | 190.2 |
| 198 | 4-CH$_3$O—C$_6$H$_4$— | 2 | CH$_2$ | C$_6$H$_5$— | N | *.H$_2$O | 123.4 |
| 199 | 2,3-dihydro-1,4-benzodioxin-2-yl | 1 | CH$_2$ | C$_6$H$_5$— | CH | 2½(COOH)$_2$ | 224.5 |
| 200 | 4-CH$_3$O—C$_6$H$_4$— | 2 | S | 4-F—C$_6$H$_4$— | CH | 2½(COOH)$_2$ | 148.1 |
| 201 | C$_2$H$_5$O—C(=O)— | 1 | CH$_2$ | 4-F—C$_6$H$_4$— | CH | 2HCl.H$_2$O | 174.7 |

*(E)—2-butenedioate(1:2)
**(E)—2-butenedioate(1:1)

In a similar manner there were also prepared:
1-[(4-fluorophenyl)methyl]-2-[[1-[2-(4-methoxyphenyl)ethyl]-4-piperidinyl]-methyl]-1H-imidazo-[4,5-c]pyridine ethanedioate (1:2); mp. 193.0° C. (202).
1-[(4-fluorophenyl)methyl]-2-[[1-[2-(4-methoxyphenyl)ethyl]-4-piperidinyl]methyl]-1H-imidazo-[4,5-b]pyridine ethanedioate(1:1); mp. 176.7° C. (203).
3-[(4-fluorophenyl)methyl]-2-[[1-[2-(4-methoxyphenyl)ethyl]-4-piperidinyl]methyl]-3H-imidazo-[4,5-c]pyridine ethanedioate(1:2); mp. 191.6° C. (204).

EXAMPLE 45

A mixture of 3.14 parts of 7-(2-bromoethyl)-3,4-dihydro-8-methyl-2H,6H-pyrimido[2,1-b][1,3]thiazin-6-one monohydrobromide, 3.5 parts of 3-[(4-fluorophenyl)methyl]-2-(4-piperidinylmethyl)-3H-imidazo-[4,5-b]pyridin, 4 parts of sodium carbonate, 0.1 parts of potassium iodide and 90 parts of N,N-dimethylformamide was stirred and heated overnight at 70° C. After cooling, water was added. The product was extracted with 4-methyl-2-pentanone. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in ethanol. The salt was filtered off and dried, yielding 3.7 parts (61%) of 7-[2-[4-[[3-[(4-fluorophenyl)methyl]-3H-imidazo[4,5-b]pyridin-2-yl]methyl]-1-piperidinyl]ethyl]-3,4-dihydro-8-methyl-2H,6H-pyrimido[2,1-b][1,3]thiazin-6-one ethanedioate (1:2); mp. 190.5° C. (205).

Following the same procedure and using equivalent amounts of the appropriate starting materials, there were also prepared:

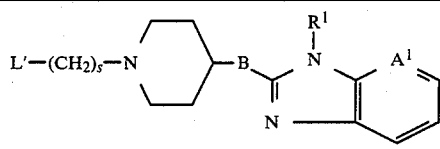

| No. | L' | s | B | $R^1$ | $A^1$ | salt/base | mp. (°C.) |
|---|---|---|---|---|---|---|---|
| 206 | ![benzamide-N] H-N, C=O, N— | 3 | CH$_2$ | C$_6$H$_5$— | CH | base | 160.7 |
| 207 | ![benzamide-N] H-N, C=O, N— | 3 | CH$_2$ | 4-F—C$_6$H$_4$CH$_2$— | CH | ** | 145.7 |
| 208 | ![phthalimide-like] H-N, C=O, N—, C=O | 2 | CH$_2$ | 2-furanylmethyl | CH | base | 210.7 |

-continued

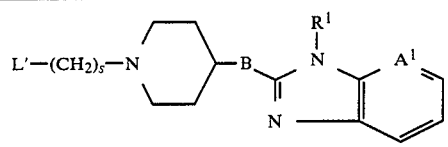

| No. | L' | s | B | R¹ | A¹ | salt/base | mp. (°C.) |
|---|---|---|---|---|---|---|---|
| 209 | 3-oxo-4H-quinazolin-4-yl (N-H, N-) | 2 | $CH_2$ | 4-F—$C_6H_4CH_2$— | CH | base | 177.8 |
| 210 | 1,4-benzodioxin-2-yl | 1 | $CH_2$ | 4-F—$C_6H_4CH_2$— | CH | 2(COOH)$_2$ | 198.6–200.1 |
| 211 | 2,3-dihydro-2-oxo-benzimidazol-1-yl | 3 | $CH_2$ | 4-$CH_3$—$C_6H_4CH_2$— | CH | 2(COOH)$_2$.$H_2O$ | 166.2 |
| 212 | 1,4-benzodioxin-2-yl | 1 | $CH_2$ | 2-thienylmethyl | N | (COOH)$_2$ | 184.1 |
| 213 | 1,4-benzodioxin-2-yl | 1 | $CH_2$ | 4-$CH_3$—$C_6H_4CH_2$— | CH | *.½$H_2O$ | 202.0 |
| 214 | 2,3-dimethyl-4H-pyrido[1,2-a]pyrimidin-4-on-2-yl | 2 | $CH_2$ | 4-F—$C_6H_4CH_2$— | CH | 2(COOH)$_2$ | 195.8 |
| 215 | 2,3-dihydro-2-oxo-benzimidazol-1-yl | 3 | $CH_2$ | 2-thienylmethyl | N | 1½(COOH)$_2$ | 173.3 |
| 216 | 2,3,6-trimethyl-thieno-pyrimidinone | 2 | $CH_2$ | 2-furanylmethyl | CH | base | 155.5 |
| 217 | 1,4-benzodioxin-2-yl | 1 | $CH_2$ | 2-pyridinylmethyl | N | 2½(COOH)$_2$ | 157.2 |
| 218 | 2,3-dimethyl-4H-pyrido[1,2-a]pyrimidin-4-on-2-yl | 2 | $CH_2$ | 2-furanylmethyl | CH | 2½(COOH)$_2$ | 115.2 |

-continued

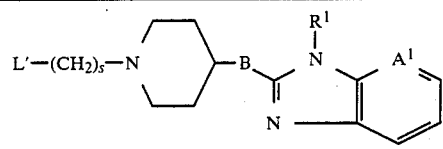

| No. | L' | s | B | R¹ | A¹ | salt/base | mp. (°C.) |
|---|---|---|---|---|---|---|---|
| 219 | [thiazine with S, N, CH₃, CH₃, C=O ring] | 2 | CH₂ | 4-F—C₆H₄CH₂— | CH | 2(COOH)₂ | 139.8 |
| 220 | [quinazoline-2,4-dione N-CH₃] | 2 | CH₂ | 4-F—C₆H₄CH₂— | CH | base | 173.8 |
| 221 | [quinazoline-2,4-dione N-CH₃] | 2 | CH₂ | 2-furanylmethyl | CH | 2(COOH)₂H₂O | 162.8 |
| 222 | [dimethyl pyrimido-pyrazine dione] | 2 | CH₂ | 2-furanylmethyl | CH | * | 192.4 |
| 223 | [dimethyl pyrimido-pyrazine dione] | 2 | CH₂ | 4-F—C₆H₄CH₂— | CH | * | 212.1 |
| 224 | [quinazoline-2,4-dione NH] | 2 | CH₂ | 4-F—C₆H₄CH₂— | N | base | 192.7 |
| 225 | [thiazine ring with S, N, CH₃, C=O] | 2 | CH₂ | 4-F—C₆H₄CH₂— | N | 2½(COOH)₂ H₂O | 125.6 |
| 226 | [pyrido-pyrimidinone with CH₃] | 2 | CH₂ | 2-furanylmethyl | CH | 3(COOH)₂.H₂O | 125.6 |

*(E)—2-butenedioate (2:3)
**(E)—2-butenedioate (1:2)

In a similar manner there were also prepared:

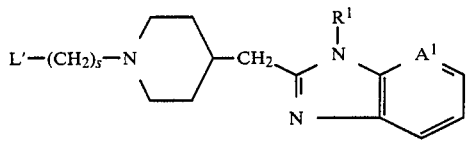

| Comp. No. | L' | s | R¹ | A¹ | base or salt | mp. °C. |
|---|---|---|---|---|---|---|
| 227 | 4-CH₃O—C₆H₄— | 2 | 4-F—C₆H₄CH₂— | CH | * | 190.5 |
| 228 | 4-F—C₆H₄—CO— | 3 | 4-F—C₆H₄CH₂— | N | * | 152.6 |
| 229 | 4-CH₃O—C₆H₄— | 2 | 2-furanylmethyl | CH | *** | 209.0 |
| 230 | C₆H₅—CH=CH— | 2 | 2-furanylmethyl | CH | ** | 167.8 |
| 231 | 4-CH₃O—C₆H₄— | 2 | C₆H₅— | CH | * | 195.8 |
| 232 | 4-CH₃O—C₆H₄— | 2 | 2-thienylmethyl | CH | *** | 205.9–207.6 |
| 233 | (4-F—C₆H₄)₂CH— | 3 | C₆H₅— | CH | 2(COOH)₂ | 163.8–165.6 |
| 234 | 4-CH₃O—C₆H₄— | 2 | 2-pyridinylmethyl | N | ** | 170.5 |
| 235 | (4-F—C₆H₄)₂CH— | 3 | 4-F—C₆H₄CH₂— | CH | 2(COOH)₂ | 130.1 |
| 236 | 4-CH₃O—C₆H₄— | 2 | 4-F—C₆H₄CH₂— | N | 2(COOH)₂ | 155.7 |
| 237 | C₂H₅—O—CO—NH— | 2 | 2-thienylmethyl | N | base | — |
| 238 | 4-CH₃O—C₆H₄— | 2 | 2-thienylmethyl | N | *** | 198.0 |
| 239 | 4-CH₃O—C₆H₄— | 2 | 4-CH₃C₆H₄CH₂ | CH | *** | 214.5 |
| 240 | (4-F—C₆H₄)₂CH— | 3 | 2-thienyl4CH₂— | N | (COOH)₂ | 192.7 |
| 241 | (4-F—C₆H₄)₂CH— | 3 | 4-CH₃C₆H₄CH₂ | CH | 2½(COOH)₂ | 116.1 |
| 242 | 4-CH₃O—C₆H₄— | 2 | CH₃ | CH | 2(COOH)₂ | 164.3 |

*(E)—2-butenedioate (2:3)
**(E)—2-butenedioate (1:2)
***(E)—2-butenedioate (1:1)

In a similar manner there were also prepared:
ethyl [2-[4-[[1-[(4-fluorophenyl)methyl]-1H-benzimidazol-2-yl]-thio]-1-piperidinyl)ethyl]carbamate dihydrobromide.hemihydrate; mp. 191.4° C. (243); and 3-[2-[4-[[1-[(4-fluorophenyl)methyl]-1H-benzimidazol-2-yl]thio]-1-piperidinyl]-ethyl]-2-methyl-4H-pyrido[1,2-a]pyrimidin-4-one trihydrochloride.monohydrate; mp. 177.8° C. (244).

EXAMPLE 46

A mixture of 1.9 parts of 1-(2-chloroethyl)-4-methoxybenzene, 4 parts of 1-(4-piperidinylmethyl)-1-(4-thiazolylmethyl)-1H-benzimidazole trihydrobromide, 8 parts of sodium carbonate, 0.1 parts of sodium iodide and 45 parts of N,N-dimethylacetamide was stirred overnight at 75° C. After cooling, the reaction mixture was poured into water and the product was extracted with 4-methyl-2-pentanone. The extract was dried, filtered and evaporated. The residual oil was converted into the hydrochloride salt in 2-propanol and the whole was evaporated. The sticky residue was crystallized from acetonitrile, yielding 2.54 parts of 2-[[1-[2-(4-methoxyphenyl)ethyl]-4-piperidinyl]methyl]-1-(4-thiazolylmethyl)-1H-benzimidazole dihydrochloride.monohydrate; mp. 154.6°–156.1° C. (245).

In a similar manner there were also prepared:

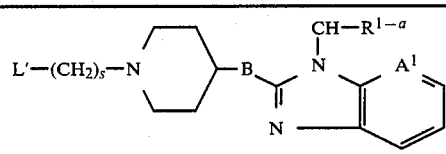

| No. | L' | s | B | R¹⁻ᵃ | A¹ | salt/base | mp. (°C.) |
|---|---|---|---|---|---|---|---|
| 246 | (CH₃)₂CH— | 0 | CH₂ | 4-thiazolylmethyl- | CH | 2(COOH)₂ | 187.5–189.7 |
| 247 | (4-F—C₆H₄)₂—CH— | 3 | CH₂ | 4-thiazolylmethyl- | CH | 2(COOH)₂ | 193.3–195.3 |
| 248 | C₂H₅O(C=O)NH— | 2 | CH₂ | 4-thiazolylmethyl- | CH | 2(COOH)₂.H₂O | 181.1 |
| 249 | 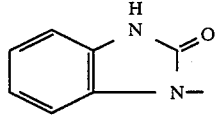 | 3 | CH₂ | 2-pyridinylmethyl- | N | 2(COOH)₂.H₂O | 159.6 |
| 250 | C₆H₅CH=CH— | 1 | CH₂ | H | CH | base | 199.2 |
| 251 | 4-CH₃O—C₆H₄— | 2 | CH₂ | H | CH | base | — |
| 252 | (CH₃)₂CH—NH—C(=O)— | 1 | CH₂ | H | CH | base | 201.3 |
| 253 | C₂H₅OC(=O)— | 1 | CH₂ | 4-F—C₆H₄CH₂— | N | 2HCl.H₂O | 147.8 |
| 254 | 4-CH₃O—C₆H₄— | 2 | SO₂ | 4-F—C₆H₄CH₂— | CH | base | 111.3 |
| 255 | 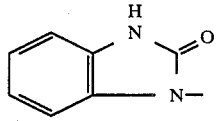 | 3 | S | 4-F—C₆H₄CH₂— | CH | base | 140.6 |

In a similar manner there were also prepared:

L'—(CH$_2$)$_s$—N(piperidine-4-yl)—B—C(=N—)—N(CH—R$^{1-a}$)—(aryl A$^1$)

| No. | L' | s | B | R$^{1-a}$ | A$^1$ | salt/base | mp. (°C.) |
|---|---|---|---|---|---|---|---|
| 256 | 3-methyl-4-oxo-4H-pyrido[1,2-a]pyrimidin-2-yl | 2 | CH$_2$ | 2-pyridinylmethyl- | N | base | 151.6 |
| 257 | 3-methyl-4-oxo-4H-pyrido[1,2-a]pyrimidin-2-yl | 2 | CH$_2$ | 2-thienylmethyl- | CH | base | 127.0 |
| 258 | 3-methyl-4-oxo-6,7,8,9-tetrahydro-4H-pyrido[1,2-a]pyrimidin-2-yl | 2 | CH$_2$ | 2-pyridinylmethyl- | N | base | 178.7 |
| 259 | 2-oxo-2H-1-benzopyran-3-yl | 2 | CH$_2$ | 2-thienylmethyl- | CH | 2(COOH)$_2$ | 216.1 |
| 260 | 4-CH$_3$O—C$_6$H$_4$— | 2 | CH$_2$ | 3-furanylmethyl | CH | 2½(COOH)$_2$ | 161.3 |
| 261 | 3-methyl-4-oxo-4H-pyrido[1,2-a]pyrimidin-2-yl | 2 | CH$_2$ | 4-thiazolylmethyl- | CH | base | 179.5 |
| 262 | 3-methyl-4-oxo-6,7,8,9-tetrahydro-4H-pyrido[1,2-a]pyrimidin-2-yl | 2 | CH$_2$ | 4-thiazolylmethyl- | CH | 2½(COOH)$_2$ H$_2$O | 187.2 |
| 263 | 3-methyl-4-oxo-6,7,8,9-tetrahydro-4H-pyrido[1,2-a]pyrimidin-2-yl | 2 | CH$_2$ | 2-thienylmethyl- | CH | 2(COOH)$_2$ | 194.3 |
| 264 | 3-methyl-4-oxo-6,7,8,9-tetrahydro-4H-pyrido[1,2-a]pyrimidin-2-yl | 2 | O | 4-F—C$_6$H$_4$CH$_2$— | CH | * | 149.8 |
| 265 | 2-oxo-2H-1-benzopyran-3-yl | 2 | CH$_2$ | 4-thiazolylmethyl- | CH | base | 138.2 |
| 266 | 4-CH$_3$O—C$_6$H$_4$— | 2 | CH$_2$ | 5-methyl-2-furanylmethyl- | CH | 2(COOH)$_2$ | 179.9 |

*(E)—2-butenedioate salt (1:2)

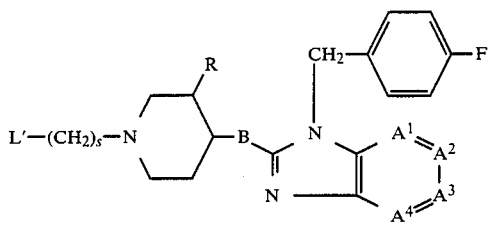

| No. | L' | s | R | B | $A_1=A_2-A_3=A_4$ | isomeric form | salt/base | mp. °C. |
|---|---|---|---|---|---|---|---|---|
| 267 | 4-CH₃O—C₆H₄— | 2 | CH₃ | O | CH=CH—CH=CH | cis | 2(COOH)₂ | 160.2 |
| 268 | 4-CH₃O—C₆H₄— | 2 | CH₃ | O | CH=CH—CH=CH | trans | base | 135.6 |
| 269 | 4-CH₃O—C₆H₄— | 2 | H | CH₂ | CH=CH—C(CH₃)=CH | — | ** | 192.7 |
| 270 | [2-(3-methyl-pyrido-pyrimidinone)] | 2 | H | CH₂ | CH=N—CH=CH | — | 3(COOH)₂ | 155.7 |
| 271 | 4-CH₃O—C₆H₄— | 2 | H | CH₂ | CH=CH—C(OCH₃)=CH | — | 2HCl. 1½H₂O | 171.8 |
| 272 | [2-(3-methyl-pyrido-pyrimidinone)] | 2 | H | CH₂ | CH=CH—CH=N | — | 2(COOH)₂ ½H₂O | 169.6 |
| 273 | 4-CH₃O—C₆H₄— | 2 | H | CH₂ | CH=C(OCH₃)—CH=CH | — | 2(COOH)₂ | 163.9 |
| 274 | [2-(3-methyl-pyrido-pyrimidinone)] | 2 | H | CH₂ | CH=CH—N=CH | — | 2(COOH)₂ H₂O | 178.3 |
| 275 | 4-CH₃O—C₆H₄— | 2 | H | CH₂ | CH=CH—C(OH)=CH | — | *** | 215.5 |
| 276 | 4-CH₃O—C₆H₄— | 2 | H | CH₂ | CH=C(OH)—CH=CH | — | base | 210.7 |

**(E)—2-butenedioate salt (2:3)
***(E)—2-butenedioate salt (1:1)

EXAMPLE 47

A mixture of 13.3 parts of 1-(2-chloroethyl)-4-methoxybenzene, 23.8 parts of 5(or 6)-fluoro-[(4-fluorophenyl)methyl]-2-(4-piperidinylmethyl)-1H-benzimidazole, 14.8 parts of sodium carbonate, 0.5 parts of potassium iodide and 250 parts of N,N-dimethylacetamide was stirred at 100° C. for 5 hours. After cooling, the mixture was poured into ice water. This mixture was extracted three times with methylbenzene. The combined organic layers were washed twice with water, dried, filtered and evaporated. The residue was purified by column chromatography over silica gel using a mixture of ethyl acetate, ethanol and ammonia (96:4:1 by volume) as eluent. The first fraction was collected and the eluent was evaporated. The residue was converted into the hydrochloride salt in 2,2'-oxybispropane and 2-propanol. The salt was filtered off and crystallized from a mixture of 2-propanol and 2,2'-oxybispropane, yielding 9.2 parts (48%) of 5-fluoro-1-[(4-fluorophenyl)methyl]-2-[[1-[2-(4-methoxyphenyl)ethyl]-4-piperidinyl]methyl]-1H-benzimidazole dihydrochloride.dihydrate; mp. 101.9° C. (277). The second fraction was collected and the eluent was evaporated. The residue was converted into the (E)-2-butenedioate salt in 2,2'-oxybispropane and 2-propanol. The salt was filtered off and crystallized from a mixture of 2- propanol and 2,2'-oxybispropane, yielding 6 parts (25%) of 6-fluoro-1-[(4-fluorophenyl)methyl]-2-(4-piperidinylmethyl)-1H-benzimidazole; mp. 191.5° C. (278).

EXAMPLE 48

A mixture of 6.4 parts of 2-chloroacetonitrile, 27 parts of 3-[(4-methylphenyl)methyl]-2-(4-piperidinylmethyl)-3H-imidazo[4,5-b]-pyridine, 13 parts of sodium carbonate and 450 parts of N,N-dimethylformamide was stirred overnight at room temperature. The reaction mixture was poured into water. The product was extracted with 4-methyl-2-pentanone. The extract was washed with water, dried, filtered and evaporated. The residue was crystallized from 1,1'-oxybisethane, yielding 19 parts (62%) of 4-[[3-[(4-methylphenyl)methyl]-3H-imidazo[4,5-b]pyridin-2-yl]methyl]-1-piperidineacetonitrile; mp. 131.3° C. (279).

Following the same procedure and using equivalent amounts of the appropriate starting materials, there were also prepared:

4-[[1-[(4-fluorophenyl)methyl]-1H-benzimidazol-2-yl]methyl]-1-piperidinebutanenitrile (280);
4-[[1-(2-furanylmethyl)-1H-benzimidazol-2-yl]methyl]-1-piperidinebutanenitrile (281);
4-[[3-(2-furanylmethyl)-3H-imidazo[4,5-b]pyridin-2-yl]methyl-1-piperidinebutanenitrile (282).

In a similar manner there were also prepared:

benzimidazol-2-yl]methyl]-1-piperidinebutanamine (302).

Following the same procedure and using equivalent amounts of the appropriate starting materials, there were also prepared:

4-[[1-(2-furanylmethyl)-1H-benzimidazol-2-yl]methyl]-1-piperidineethanamine (E)-2-butenedioate (1:3); mp. 210.9° C. (303);
4-[[3-(2-furanylmethyl)-3H-imidazo[4,5-b]pyridin-2-yl]methyl]-1-piperidineethanamine (E)-2-butenedioate (1:3); mp. 203.0° C. (304);
4-[[1-[(4-fluorophenyl)methyl]-1H-benzimidazol-2-yl]methyl]-1-piperidinebutanamine (305);
4-[[3-(2-furanylmethyl)-3H-imidazo[4,5-b]pyridin-2-yl]methyl]-1-piperidinebutanamine (306);
4-[[1-[(4-fluorophenyl)methyl]-1H-imidazo[4,5-b]pyridin-2-yl]methyl]-1-piperidineethanamine (307);
4-[[3-[(4-fluorophenyl)methyl]-3H-imidazo[4,5-c]pyridin-2-yl]methyl]-1-piperidineethanamine (308);
cis-4-[[1-[(4-fluorophenyl)methyl]-1H-benzimidazol-2-yl]oxy]-3-methyl-1piperidineethanamine (309).

In a similar manner there were also prepared:

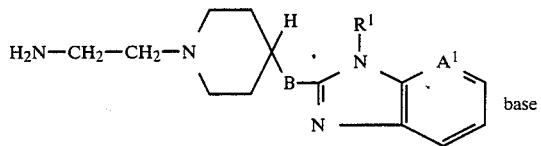

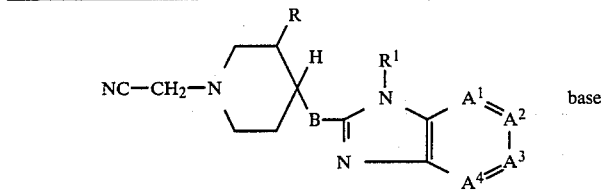

| No. | R | B | R₁ | A₁=A₂—A₃=A₄ | mp. °C. |
|---|---|---|---|---|---|
| 283 | H | CH₂ | 4-F—C₆H₄—CH₂ | CH=CH—CH=CH | 146.1 |
| 284 | H | CH₂ | C₆H₅ | CH=CH—CH=CH | 141.4 |
| 285 | H | CH₂ | 2-furanylmethyl | CH=CH—CH=CH | 152.5 |
| 286 | H | O | 4-F—C₆H₄—CH₂ | CH=CH—CH=CH | — |
| 287 | H | CH₂ | 2-thienylmethyl | CH=CH—CH=CH | — |
| 288 | H | CH₂ | 3-pyridinylmethyl | CH=CH—CH=CH | — |
| 289 | H | CH₂ | 4-thiazolylmethyl | CH=CH—CH=CH | 91.2–93.0 |
| 290 | H | CH₂ | 4-F—C₆H₄—CH₂ | N=CH—CH=CH | 98.9 |
| 291 | H | CH₂ | 2-furanylmethyl | N=CH—CH=CH | 124.2 |
| 292 | H | CH₂ | 2-pyridinylmethyl | N=CH—CH=CH | 137.9 |
| 293 | H | CH₂ | 4-CH₃O—C₆H₄—CH₂ | CH=CH—CH=CH | 129.8 |
| 294 | H | CH₂ | H | CH=CH—CH=CH | 205.4 |
| 295 | H | CH₂ | 4-CH₃—C₆H₄—CH₂ | CH=CH—CH=CH | 161.6 |
| 296 | H | CH₂ | C₆H₅—CH₂ | N=CH—CH=CH | 140.0 |
| 297 | H | CH₂ | C₆H₅—CH₂ | CH=CH—CH=CH | 174.3 |
| 298 | H | CH₂ | 4-CH₃O—C₆H₄—CH₂ | N=CH—CH=CH | 96.6 |
| 299 | H | CH₂ | 4-F—C₆H₄—CH₂ | CH=CH—CH=N | — |
| 300* | CH₃ | CH₂ | 4-F—C₆H₄—CH₂ | CH=CH—CH=CH | 127.4 |
| 301 | H | CH₂ | 4-F—C₆H₄—CH₂ | CH=N—CH=CH | 132.9 |

*cis-isomer

EXAMPLE 49

A mixture of 7.4 parts of 4-[[1-(2-furanylmethyl)-1H-benzimidazol-2-yl]methyl]-1-piperidinebutanenitrile and 240 parts of methanol saturated with ammonia was hydrogenated at normal pressure and at room temperature with 3 parts of Raney-nickel catalyst. After the calculated amount of hydrogen was taken up, the catalyst was filtered off and the filtrate was evaporated, yielding 7.33 parts (99%) of 4-[[1-(2-furanylmethyl)-1H-

| Comp. No. | B | R¹ | A¹ |
|---|---|---|---|
| 310 | CH₂ | 4-F—C₆H₄—CH₂— | CH |
| 311 | CH₂ | C₆H₅— | CH |
| 312 | O | 4-F—C₆H₄—CH₂— | CH |
| 313 | CH₂ | 2-thienylmethyl | CH |
| 314 | CH₂ | 3-pyrindinylmethyl | CH |
| 315 | CH₂ | 4-thiazolylmethyl | CH |
| 316 | CH₂ | 4-F—C₆H₄—CH₂— | N |

-continued

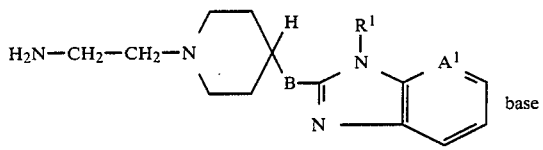

| Comp. No. | B | R¹ | A¹ |
|---|---|---|---|
| 317 | CH₂ | 2-pyrindinylmethyl | N |
| 318 | CH₂ | 4-CH₃O—C₆H₄—CH₂— | CH |
| 319 | CH₂ | H | CH |
| 320 | CH₂ | 4-CH₃—C₆H₄—CH₂— | CH |
| 321 | CH₂ | C₆H₅—CH₂— | CH |
| 322 | CH₂ | C₆H₅—CH₂— | N |
| 323 | CH₂ | 4-CH₃—C₆H₄—CH₂— | N |
| 324 | CH₂ | 4-CH₃O—C₆H₄—CH₂— | N |

EXAMPLE 50

A mixture of 20.7 parts of ethyl [2-[4-[[3-(2-thienylmethyl)-3H-imidazo[4,5-b]pyridin-2-yl]methyl]-1-piperidinyl]ethyl]carbamate, 22.1 parts of potassium hydroxide and 200 parts of 2-propanol was stirred and refluxed overnight. The reaction mixture was evaporated. Water was added to the residue. The product was extracted with dichloromethane. The extract was dried, filtered and evaporated, yielding 13 parts (76%) of 4-[[3-(2-thienylmethyl)-3H-imidazo[4,5-b]pyridin-2-yl]methyl]-1-piperidinethanamine (325).

In a similar manner there was also prepared:
4-[[1-[(4-fluorophenyl)methyl]-1H-benzimidazol-2-yl]thio]-1-piperidineethanamine (326).

EXAMPLE 51

A mixture of 12 parts of 4-[[1-[(4-fluorophenyl)methyl]-1H-benzimidazol-2-yl]methyl]-1'-(phenylmethyl)[1,4'-bipiperidine] and 200 parts of methanol was hydrogenated at normal pressure and 50° C. with 3 parts of palladium-on-charcoal catalyst 10%. After the calculated amount of hydrogen was taken up, the catalyst was filtered off and the filtrate was evaporated. The residue was converted into the (E)-2-butenedioate salt in methanol. The salt was filtered off and dried, yielding 7.87 parts (51.3%) of 4-[[1-[(4-fluorophenyl)methyl]-1H-benzimidazol-2-yl]methyl]-[1,4'-bipiperidine] (E)-2-butenedioate(1:2); mp. 226.9° C. (327).

EXAMPLE 52

A mixture of 3 parts of 2-chloro-1H-benzimidazole, 7.3 parts of 4-[[1-[(4-fluorophenyl)methyl]-1H-benzimidazol-2-yl]methyl]-1-piperidineethanamine and 0.1 parts of potassium iodide was stirred for 1 hour in an oil bath at 160° C. After cooling to room temperature, the whole was pulverized and stirred in a mixture of water, ammonium hydroxide and trichloromethane. The layers were separated. The organic layer was washed twice with water, dried, filtered and evaporated. The residue was purified by column chromatography over silica gel using a mixture of hexane, trichloromethane, methanol and ammonium hydroxide (45:45:9:1 by volume) as eluent. The pure fractions were collected and the eluent was evaporated. The residue was converted into the (E)-2-butenedioate salt in 2-propanone. The salt was filtered off and crystallized from ethanol. The product was filtered off and dried in vacuo at 70° C. overnight, yielding 5 parts (38.0%) of N-[2-[4-[[1-[(4-fluorophenyl)methyl]-1H-benzimidazol-2-yl]methyl]-1-piperidinyl]ethyl]1H-benzimidazol-2-amine (E)-2-butenedioate(2:3); mp. 134.5° C. (328).

In a similar manner there were also prepared:
N-[2-[4-[[3-[(4-fluorophenyl)methyl]-3H-imidazo[4,5-b]pyridin-2-yl]methyl]-1-piperidinyl]ethyl]1H-benzimidazol-2-amine; mp. 161.9° C. (329).

EXAMPLE 53

A mixture of 3 parts of 2-methylthio-thiazolo[5,4-b]pyridine and 5.5 parts of 4-[[1-[(4-fluorophenyl)methyl]-1H-benzimidazol-2-yl]methyl]-1-piperidineethanamine was stirred for 24 hours at 140° C. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in ethanol. The salt was filtered off and dried, yielding 1 part (8.6%) of N-[2-[4-[[1-[(4-fluorophenyl)methyl]-1H-benzimidazol-2-yl]methyl]-1-piperidinyl]ethyl]thiazolo[5,4-b]pyridin-2-amine ethanedioate(1:3); mp. 148.2° C. (330).

In a similar manner there were also prepared:
2-[[2-[4-[[1-[(4-fluorophenyl)methyl]-1H-benzimidazol-2-yl]methyl]-1-piperidinyl]ethyl]amino]-4(1H)-pyrimidinone; mp. 164.0° C. (331);
N-[2-[4-[[1-[(4-fluorophenyl)methyl]-1H-benzimidazol-2-yl]methyl]-1-piperidinyl]ethyl]thiazolo[4,5-c]pyridin-2-amine ethanedioate(1:3); mp. 188.0° C. (332).

EXAMPLE 54

A mixture of 1.7 parts of 2-chloropyrimidine, 5.7 parts of 4-[[1-[(4-fluorophenyl)methyl]-1H-benzimidazol-2-yl]thio]-1-piperidineethanamine, 1.3 parts of sodium hydrogen carbonate and 120 parts of ethanol was stirred and refluxed overnight. The reaction mixture was filtered and the filtrate was evaporated. The residue was taken up in trichloromethane. The solution was washed with water, dried, filtered and evaporated. The residue was purified by column-chromatography over silica gel using a mixture of trichloromethane and methanol (95:5 by volume) as eluent. The pure fractions were collected and the eluent was evaporated. The residue was converted into the ethanedioate salt in ethanol. The salt was filtered off and dried, yielding 3.7 parts (44.6%) of N-[2-[4-[[1-[(4-fluorophenyl)methyl]-1H-benzimidazol-2-yl]thio]-1-piperidinyl]ethyl]-2-pyrimidinamine ethanedioate (1:1); mp. 189.2° C. (333).

In a similar manner there were also prepared:

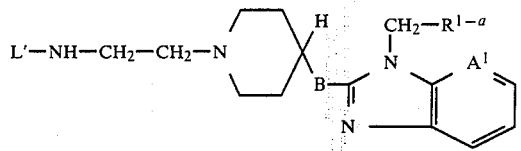

| Comp. No. | L' | B | $R^{1-a}$ | $A^1$ | base or salt | mp. °C. |
|---|---|---|---|---|---|---|
| 334 | 2-pyrimidinyl | $CH_2$ | 2-furanyl- | CH | base | 103.0 |
| 335 | 2-thiazolyl | $CH_2$ | 2-furanyl- | CH | * | 159.6 |
| 336 | 2-pyrimidinyl | $CH_2$ | 2-thienyl- | CH | ** | 184.6–188.6 |
| 337 | 2-pyrimidinyl | $CH_2$ | 3-pyridinyl- | CH | $4(COOH)_2$ | 176.1–180.5 |
| 338 | 2-pyrimidinyl | $CH_2$ | 4-thiazolyl- | CH | $4(COOH)_2$ | 192.3–194.0 |
| 339 | 2-pyrimidinyl | $CH_2$ | 2-furanyl- | N | $3(COOH)_2$ | 107.3 |
| 340 | 2-pyrimidinyl | $CH_2$ | 2-pyridinyl- | N | $3\frac{1}{2}(COOH)_2$ | 151.7 |
| 341 | 2-pyrimidinyl | $CH_2$ | $4-CH_3OC_6H_4-$ | CH | ** | 182.2 |
| 342 | 2-pyrimidinyl | $CH_2$ | 2-thienyl- | N | $**H_2O$ | 152.9 |
| 343 | 2-pyrimidinyl | $CH_2$ | $4-CH_3-C_6H_4-$ | CH | $2\frac{1}{2}(COOH)_2$ | 160.5 |
| 344 | 2-pyrimidinyl | $CH_2$ | $C_6H_5-$ | CH | ** | 194.8 |
| 345 | 2-pyrimidinyl | $CH_2$ | $C_6H_5-$ | N | $3(COOH)_2$ | 172.5 |
| 346 | 2-pyrimidinyl | O | $4-F-C_6H_4-$ | CH | base | 155.1 |

In a similar manner there were also prepared:
4-[[1-[(4-fluorophenyl)methyl]-1H-benzimidazol-2-yl]methyl]-1'-(2-pyrimidinyl)-[1,4'-bipiperidine]ethanedioate(2:7); mp. 169.7° C. (347);

N-[2-[4[[1-[(4-fluorophenyl)methyl]-1H-imidazo[4,5-b]pyridin-2-yl]methyl]-1-piperidinyl]ethyl]-2-pyrimidinamine ethanedioate(2:5); mp. 173.4° C. (348);

cis-N-[2-[4-[[1-[(4-fluorophenyl)methyl]-1H-benzimidazol-2-yl]oxy]-3-methyl-1-piperidinyl]ethyl]-2-pyrimidinamine; mp. 94.0° C. (349);

6-chloro-$N^4$-[2-[4-[[1-[(4-fluorophenyl)methyl]-1H-benzimidazol-2-yl]methyl]-1-piperidinyl]ethyl]-4,5-pyrimidinediamine (350); and N-[2-[4-[[3-[(4-fluorophenyl)methyl]-3H-imidazo[4,5-c]pyridin-2-yl]methyl]-1-piperdinyl]-ethyl]-2-pyrimidinamine ethanedioate(1:2); mp. 192.5° C. (351).

EXAMPLE 55

A mixture of 3.3 parts of 2-bromothiazole, 5.09 parts of 4[[3-(2-furanylmethy)-3H-imidazo[4,5-b]pyridin-2-yl]methyl]-1-piperidineethanamine, 3 parts of sodium carbonate and 45 parts of N,N-dimethylacetamide was stirred overnight at 130° C. The reaction mixture was poured into water and the product was extracted twice with 4-methyl-2-pentanone. The extract was dried, filtered and evaporated. The residue was purified by column chromatography over silica gel using a mixture of trichloromethane and methanol saturated with ammonia (95:5 by volume) as eluent. The pure fractions were collected and the eluent was evaporated. The residue was converted into the ethanedioate salt in ethanol. The salt was filtered off and dried, yielding 2.5 parts (27%) of 4-[[3-(2-furanylmethyl)-3H-imidazo[4,5-b]pyridin-2-yl]methyl]-N-(2-thiazolyl)-1-piperidineethanamine ethanedioate (1:3); mp. 173.0° C. (352).

In a similar manner there were also prepared:

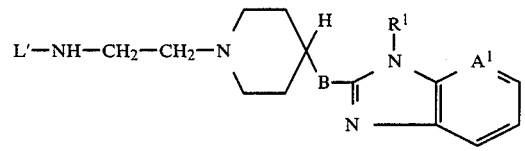

| Comp. No. | L' | B | $R^1$ | $A^1$ | base or salt | mp. °C. |
|---|---|---|---|---|---|---|
| 353 | 2-thiazolyl | $CH_2$ | $4-F-C_6H_4CH_2-$ | CH | base | 115.6 |
| 354 | 2-thiazolyl | $CH_2$ | $C_6H_5-$ | CH | base | 59.5 |
| 355 | 2-thiazolyl | O | $4-F-C_6H_4CH_2-$ | CH | base | 132.1 |
| 356 | 2-thiazolyl | $CH_2$ | 2-thienylmethyl | CH | $3(COOH)_2H_2O$ | 135.6 |
| 357 | 2-thiazolyl | $CH_2$ | $4-F-C_6H_4CH_2-$ | N | $2\frac{1}{2}(COOH)_2H_2O$ | 150.9 |
| 358 | 2-pyrimidinyl | $CH_2$ | H | CH | base | 199.4 |
| 359 | 2-thiazolyl | $CH_2$ | H | CH | base | 180.4 |
| 360 | 5-chloro-2-pyridinyl | $CH_2$ | $4-F-C_6H_4CH_2$ | CH | base | — |
| 361 | 2-thiazolyl | $CH_2$ | 2-thienylmethyl | N | $3(COOH)_2$ | 129.4 |
| 362 | 2-thiazolyl | $CH_2$ | $C_6H_5CH_2-$ | N | $3\frac{1}{2}(COOH)_2$ | 129.4 |
| 363 | 2-thiazolyl | $CH_2$ | $C_6H_5CH_2-$ | CH | $4(COOH)_2$ | 142.7 |
| 364 | 2-thiazolyl | $CH_2$ | $4-CH_3-C_6H_4CH_2-$ | CH | $3(COOH)_2H_2O$ | 138.6 |
| 365 | 2-thiazolyl | $CH_2$ | $4-CH_3O-C_6H_4CH_2-$ | N | base | 144.7 |
| 366 | $2-NO_2-C_6H_4$ | $CH_2$ | $4-F-C_6H_4CH_2-$ | CH | base | 120.5 |
| 367 | 2-benzothiazolyl | $CH_2$ | $4-F-C_6H_4CH_2-$ | CH | $3\frac{1}{2}(COOH)_2 \frac{1}{2}H_2O$ | 167.1 |
| 368 | 2-pyrazinyl | $CH_2$ | $4-F-C_6H_4CH_2$ | CH | $2(COOH)_2$ | 173.6 |

-continued

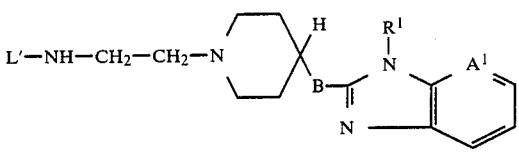

| Comp. No. | L' | B | R¹ | A¹ | base or salt | mp. °C. |
|---|---|---|---|---|---|---|
| 369 | 9-methyl-9H—purin-6-yl | CH₂ | 4-F—C₆H₄CH₂— | CH | 4HCl.H₂O | 210.3 |
| 370 | 9H—purin-6-yl | CH₂ | 4-F—C₆H₄CH₂— | CH | base | 186.5 |
| 371 | 8-OH, 9-CH₃—9H—purin-6-yl | CH₂ | 4-F—C₆H₄CH₂— | CH | 2½(COOH)₂ | 179.7 |
| 372 | 8,9-(CH₃)₂—9H—purin-6-yl | CH₂ | 4-F—C₆H₄CH₂— | CH | base | 134.3 |

In a similar manner there was also prepared:
N-[2-[4-[[3-[(4-fluorophenyl)methyl]-3H-imidazo[4,5-c]pyridin-2-yl]methyl]-1-piperidinyl]ethyl]-2-pyrazinamine ethanedioate(1:2); mp. 157.4° C. (373).

EXAMPLE 56

A mixture of 1.7 parts of 2-chloropyrimidine, 5.5 parts of 4-[[1-[(4-fluorophenyl)methyl]-1H-benzimidazol-2-yl]methyl]-1-piperidineethanamine, 2.12 parts of sodium carbonate, 0.1 parts of potassium iodide and 90 parts of N,N-dimethylformamide was stirred overnight at 60°-70° C. Water was added and the product was extracted with 4-methyl-2-pentanone. The extract was dried, filtered and evaporated. The residue was purified by column chromatography over silica gel using a mixture of trichloromethane and methanol (95:5 by volume) saturated with ammonia, as eluent. The pure fractions were collected and the eluent was evaporated. The residue was crystallized from 1,1'-oxybisethane. The product was filtered off and dried, yielding 2.6 parts (40%) of N-[2-[4-[[1-[(4-fluorophenyl)methyl]-1H-benzimidazol-2-yl[methyl]-1-piperdinyl]ethyl]-2-pyrimidinamine; mp. 125.1° C. (374).

In a similar manner there were also prepared:
N-[2-[4-[(1-phenyl-1H-benzimidazol-2-yl)methyl]-1-piperidinyl]ethyl]-2-pyrimidinamine (E)-2-butenedioate (1:1); mp. 211.4° C. (375);
N-[2-[4-[[3-[(4-fluorophenyl)methyl]-3H-imidazo[4,5-b]pyridin-2-yl]methyl]-1-piperidinyl]ethyl]-2-pyrimidinamine (E)-2-butenediote (2:3); mp. 162.4° C. (376);
4-[[1-[(4-fluorophenyl)methyl]-1H-benzimidazol-2-yl]methyl]-N-(1-methyl-4-nitro-1H-imidazol-5-yl)-1-piperidineethanamine; mp. 131.1° C. (377);
6-chloro-N-[2-[4-[[1-[(4-fluorophenyl)methyl]-1H-benzimidazol-2-yl]methyl]-1-piperidinyl]ethyl]-3-pyridazinamine; mp. 175.5° C. (378);
N-[2-[4-[[1-[(4-fluorophenyl)methyl]-1H-benzimidazol-2-yl]methyl]-1-piperidinyl]ethyl]-4-nitro-3-pyridinamine, 1-oxide; mp. 135.1° C. (379);
4-[[1-[(4-fluorophenyl)methyl]-1H-benzimidazol-2-yl]methyl]-1'-(1-methyl-4-nitro-1H-imidazol-5-yl)-[1,4'-bipiperidine]; mp. 144.0° C. (380); and
4-chloro-N-[2-[4-[[1-[(4-fluorophenyl)methyl]-1H-benzimidazol-2-yl]methyl]-1-piperidinyl]ethyl]-1-phthalazinamine; mp. 169.7° C. (381).

EXAMPLE 57

To a stirred and cooled (0°-10° C.) mixture of 18.3 parts of 4-[[1-[(4-fluorophenyl)methyl]-1H-benzimidazol-2-yl]methyl]-1-piperidineethanamine, 7.5 parts of N,N-diethylethanamine and 225 parts of tetrahydrofuran was added dropwise a solution of 8.15 parts of 2,6-dichloro-4-methylpyrimidine in a small amount of tetrahydrofuran. Upon completion, stirring was continued overnight at room temperature. The reaction mixture was evaporated. Water was added to the residue and the product was extracted with 4-methyl-2-pentanone. The extract was dried, filtered and evaporated. The residue was purified by HPLC over silica gel using a mixture of methylbenzene, ethanol and methanol, saturated with ammonia, (85:14:1 by volume) as eluent. The first fraction was collected and the eluent was evaporated. The residue was converted into the ethanedioate salt in ethanol. The salt was filtered off and dried, yieldiing 2.2 parts (6.5%) of 4-chloro-N-[2-[4-[[1-[(4-fluorophenyl)methyl]-1H-benzimidazol-2-yl]methyl]-1-piperidinyl]ethyl]-6-methyl-2-pyrimidinamine ethanedioate (1:2); mp. 165.8° C. (382).

In a similar manner there were also prepared:
2-chloro-N-[2-[4-[[1-[(4-fluorophenyl)methyl]-1H-benzimidazol-2-yl]methyl]-1-piperidinyl]ethyl]-6-methyl-4-pyrimidinamine; mp. 142.9° C. (383);
6-chloro-N-[2-[4-[[1-[(4-fluorophenyl)methyl]-1H-benzimidazol-2-yl]methyl]-1-piperidinyl[ethyl]-4-pyrimidinamine ethanedioate(2:5); mp. 174.4° C. (384).

EXAMPLE 58

A mixture of 4 parts of 5-(2-bromoethoxy)-1-methyl-1H-tetrazole, 5.5 parts of 4-[[1-[(4-fluorophenyl)methyl]-1H-benzimdazol-2-yl]methyl]-1-piperdineethanamine, 2.3 parts of sodium carbonate and 45 parts of N,N-dimethylformamide was stirred overnight at 70° C. The reaction mixture was poured into water. The product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the ethanedioate salt in ethanol. The salt was filtered off and dried, yielding 1.3 parts (13%) of 3-[2-[4-[[1-[(4-fluorophenyl)methyl]-1H-benzimidazol-2-yl]methyl]-1-piperidinyl]ethyl]2-oxazolidinone ethanedioate(2:5); mp. 147.9° C. (385).

EXAMPLE 59

To a stirred mixture of 22 parts of 4-[[1-[(4-fluorophenyl)methyl]-1H-benzimidazol-2-yl]methyl]-1- piperidineethanol dihydrochloride and 450 parts of trichloromethane were added dropwise 12 parts of thionyl chloride. Upon completion, stirring was continued overnight at reflux temperature. The reaction mixture was evaporated. The residue was stirred in methylbenzene. The product was filtered off and dried, yielding 13 parts (56.6%) of 2-[[1-(2-chloroethyl)-4-piperidinyl]methyl]-1-[(4-fluorophenyl)methyl]-1H-benzimidazole dihydrochloride (386).

EXAMPLE 60

A mixture of 2.0 parts of thiazolo[5,4-b]pyridine-2-thiol, 2 parts of a sodium hydride dispersion 50% and 45 parts of N,N-dimethylformamide was stirred for 2 hours. 6.5 Parts of 2-[[1-(2-chloroethyl)-4-piperidinyl]methyl]-1-[(4-fluorophenyl)methyl]-1H-benzimidazole dihydrochloride were added portionwise. Upon completion, stirring was continued over weekend. Water was added. The product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the ethanedioate salt in methanol. The salt was filtered off and crystallized from methanol. The product was filtered off and dried, yielding 1.7 parts (20%) of 2-[[2-[4-[[1-[(4-[[1-[(4-fluorophenyl)methyl]-1H-benzimidazol-2-yl]methyl]-1-piperidinyl]ethyl]thio]thiazolo[5,4-b]pyridine ethanedioate(1:2); mp. 199.0° C. (387).

In a similar manner there were also prepared:
2-[[2-[4-[[1-[(4-fluorophenyl)methyl]-1H-benzimidazol-2-yl]methyl]-1-piperidinyl]ethyl]thio]thiazolo[4,5-c]pyridine; mp. 121.0° C. (388).

EXAMPLE 61

To a stirred and warm mixture of 3.8 parts of 4-[[3-[(4-fluorophenyl)methyl]-3H-imidazo[4,5-b]pyridin-2-yl]methyl]-1-piperidineacetamide and 24 parts of N,N-dimethylacetamide were added portionwise 0.4 parts of a sodium hydride dispersion 59.7% at 40° C. The mixture was heated to 80° C. and stirred for 15 minutes at 80° C. 1.2 Parts of 2-chloropyrimidine were added and stirring was continued for 30 minutes at 80° C. After cooling to 40°, another 0.4 parts of a sodium hydride dispersion 59.7% were added and after stirring for 15 minutes at 80° C., another 1.2 parts of 2-chloropyrimidine were added. The whole was stirred for 30 minutes at 80° C. and then cooled to 40° C. Another 0.4 parts of a sodium hydride dispersion 59.7% were added and after stirring for 15 minutes at 80° C., another 1.2 parts of 2-chloropyrimidine were added. Stirring was continued for 15 minutes at 80° C. The reaction mixture was cooled to room temperature and poured into 150 parts of water. The product was extracted three times with dichloromethane. The combined extracts were washed three times with water, dried, filtered and evaporated. The residue was purified by column chromatography over silica gel using a mixture of trichloromethane, methanol and methanol, saturated with ammonia, (96:3:1 by volume) as eluent. The pure fractions were collected and the eluent was evaporated. The residue was converted into the (E)-2-butenedioate salt in 2-propanone. The salt was allowed to crystallize at −20° C. It was filtered off and dried, yielding 0.4 parts of 4-[[3-[(4-fluorophenyl)methyl]-3H-imidazo[4,5-b]pyridin-2-yl]methyl]-N-(2-pyrimidinyl)-1-piperidineacetamide (E)-2-butenedioate(1:2); mp. 159.0° C. (389).

In a similar manner there were also prepared:
1-[(4-fluorophenyl)methyl]-2-[[1-[2-(2-pyrimidinyloxy)ethyl]-4-piperidinyl]oxy]-1H-benzimidazole (E)-2-butenedioate (1:2); mp. 162.7° C. (390);
1-[(4-fluorophenyl)methyl]-2-[[1-[2-(2-pyrimidinyloxy)ethyl]-4-piperidinyl]methyl]-1H-benzimidazole ethanedioate(1:3); mp. 161.4° C. (391);
1-(2-furanylmethyl)-2-[[1-[2-(2-pyrimidinyloxy)ethyl]-4-piperidinyl]methyl]-1H-benzimidazole ethanedioate (1:2). monohydrate; mp. 179.3° C. (392);
1-[(4-fluorophenyl)methyl]-2-[[1-[2-(2-pyrimidinyloxy)ethyl]-4-piperidinyl]thio]-1H-benzimidazole ethanedioate (1:1); mp. 186.9° C. (393); and
3-[(4-fluorophenyl)methyl]-2-[[1-[2-(2-pyridinylmethoxy)ethyl]-4-piperidinyl]-methyl]-3H-imidazol[4,5-b]pyridine trihydrochloride; mp. 129.8° C. (394).

EXAMPLE 62

To a stirred and cooled (−10° C.) mixture of 20.8 parts of carbon disulfide, 9 parts of N,N'-methanetetraylbis[cyclohexanamine] and 135 parts of tetrahydrofuran was added dropwise a solution of 15 parts of 4-[[1-(phenylmethyl)-1H-benzimidazol-2-yl]methyl]-1-piperidineethanamine in tetrahydrofuran at a temperature below −10° C. The reaction mixture was allowed to reach room temperature and the solvent was evaporated. The residue was crystallized from acetonitrile. The precipitate was filtered off and the filtrate was evaporated, yielding 15 parts (89%) of 2-[[1-(2-isothiocyanatoethyl)4-piperidinyl]methyl]-1-(phenylmethyl)-1H-benzimidazole (395).

In a similar manner there were also prepared:

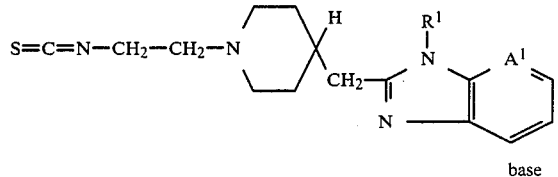

| Comp. No. | R¹ | A¹ |
|---|---|---|
| 396 | 4-F—C₆H₄—CH₂ | CH |
| 397 | 2-thienylmethyl | CH |
| 398 | 2-furanylmethyl | N |
| 399 | 2-furanylmethyl | CH |
| 400 | 4-F—C₆H₄—CH₂ | N |
| 401 | 2-pyridinylmethyl | N |
| 402 | 2-thienylmethyl | N |
| 403 | 4-CH₃—C₆H₄—CH₂ | CH |
| 404 | 4-CH₃—C₆H₄—CH₂ | N |

EXAMPLE 63

A mixture of 5.2 parts of 3,4-pyridinediamine, 19 parts of 2-[[1-(2-isothiocyanatoethyl)-4-piperidinyl]methyl]-1-[(4-methylphenyl)methyl]-1H-benzimidazole and 225 parts of tetrahydrofuran was stirred and refluxed overnight. The reaction mixture was evaporated, yielding 24 parts (100%) of N-(4-amino-3-pyridinyl)-N'-[2-[4-[[1-[(4-methylphenyl)methyl]-1H-benzimidazol-2-yl]methyl]-1-piperidinyl]-ethyl]thiourea (405).

Following the same procedure and using equivalent amounts of the appropriate starting materials, there were also prepared:

N-(4-amino-3-pyridinyl)-N'-[2-[4-[[1-[(4-fluorophenyl)methyl]-1H-benzimidazol-2-yl]methyl]-1-piperidinyl]ethyl]thiourea (406);

N-(4-amino-3-pyridinyl)-N'-[2-[4-[[1-(2-thienylmethyl)-1H-benzimidazol-2-yl]methyl-1-piperidinyl]ethyl]thiourea (407);

N-(4-amino-3-pyridinyl)-N'-[2-[4-[[3-(2-furanylmethyl)-3H-imidazo[4,5-b]pyridin-2-yl]methyl]-1-piperidinyl]ethyl]thiourea (408);

N-(4-amino-3-pyridinyl)-N'-[2-[4-[[1-(2-furanylmethyl)-1H-benzimidazol-2-yl]methyl]-1-piperidinyl[ethyl]-thiourea (409);

N-(4-amino-3-pyridinyl)-N'-[2-[4-[[3-[(4-fluorophenyl)methyl]-3H-imidazo[4,5-b]pyridin-2yl]methyl]-1-piperidinyl]ethyl]thiourea (410);

N-(4-amino-3-pyridinyl)-N'-[2-[4-[[3-(2-pyridinylmethyl)-3H-imidazo[4,5-b]pyridin-2-yl]methyl]-1-piperidinyl]ethyl]thiourea (411);

N-(4-amino-3-pyridinyl)-N'-[2-[4-[[3-(2-thienylmethyl)-3H-imidazo[4,5-b]pyridin-2-yl]methyl]-1-piperidinyl]ethyl]thiourea (412);

N-(4-amino-3-pyridinyl)-N'-[2-[4-[(1-(phenylmethyl)-1H-benzimidazol2-yl]methyl]-1-piperidinyl]ethyl]thiourea (413); and N-(4-amino-3-pyridinyl)-N'-[2-[4-[[3-[(4-methylphenyl)methyl]-3H-imidazo[4,5-b]pyridin-2-yl]methyl]-1-piperidinyl]ethyl]thiourea (414).

EXAMPLE 64

A mixture of 2 parts of N-(4-amino-3-pyridinyl)-N'-[2-[4-[[1-[(4-fluorophenyl)methyl]-1H-benzimidazol-2-yl]methyl]-1-piperidinyl]ethyl]thiourea, 3.3 parts of mercury(II) oxide, 0.1 parts of sulfur and 40 parts of ethanol was stirred and refluxed overnight. The reaction mixture was filtered hot over Hyflo and the filtrate was evaporated. The residue was converted into the (E)-2-butenedioate salt in ethanol. The salt was filtered off and dried, yielding 1.8 parts (57%) of N-[2-[4-[[1-[(4-fluorophenyl)methyl]-1H-benzimidazol-2yl]methyl]1-piperidinyl]ethyl]-1H-imidazo[4,5-c]pyridin-2-amine (E)-2-butenedioate (1:3); mp. 184.7° C. (415).

In a similar manner there were also prepared:
N-[2-[4-[[1-(2-thienylmethyl)-1H-benzimidazol-2-yl]methyl]-1-piperidinyl]ethyl]-1H-imidazo[4,5-c]pyridin-2-amine (E)-2-butenedioate (1:3). monohydrate; mp. 198.2° C. (416);

N-[2-[4-[[3-(2-furanylmethyl)-3H-imidazo[4,5-b]pyridin-2-yl]methyl]-1-piperidinyl]ethyl]-1H-imidazo[4,5-c]pyridin-2-amine (E)-2-butenedioate (1:3). monohydrate; mp. 174.6° C. (417);

N-[2-[4-[[1-(2-furanylmethyl)-1H-benzimidazol-2-yl]methyl]-1-piperidinyl]ethyl]-1H-imidazo[4,5-c]pyridin-2-amine ethanedioate (1:4); mp. 201.1° C. (418);

N-[2-[4-[[3-(2-pyridinylmethyl)-3H-imidazo[4,5-b]pyridin-2-yl]methyl]-1-piperidinyl]ethyl]-1H-imidazo[4,5-c]pyridin-2-amine ethanedioate (1:4); mp. 189.7° C. (419);

N-[2-[4-[[3-(2-thienylmethyl)-3H-imidazo[4,5-b]pyridin-2-yl]methyl]-1-piperidinyl]ethyl]-1H-imidazo[4,5-c]pyridin-2-amine ethanedioate (2:5); mp. 154.5° C. (420);

N-[2-[4-[[1-[(4-methylphenyl)methyl]-1H-benzimidazol-2-yl]methyl1-piperidinyl]ethyl]-1H-imidazo-[4,5-c]pyridin-2-amine ethanedioate (1:3); mp. 203.5° C. (421);

N-[2-[4-[[1-(phenylmethyl)-1H-benzimidazol-2-yl]methyl]-1-piperidinyl]ethyl]-1H-imidazo[4,5-c]pyridin-2-amine ethanedioate (1:4); mp. 199.0° C. (422);

N-[2-[4-[[3-[(4-methylphenyl)methyl]-3H-imidazo[4,5-b]pyridin-2-yl]methyl]-1-piperidinyl]ethyl]-1H-imidazo[4,5-c]pyridin-2-amine ethanedioate (1:5); mp. 160.1° C. (423); and N-[2-[4-[[3-[(4-fluorophenyl)methyl]-3H-imidazo[4,5-b]pyridin-2-yl]methyl]-1-piperidinyl]ethyl]-1H-imidazo[4,5-c]pyridin-2-amine ethanedioate (2:5); mp. 211.2° C. (424).

EXAMPLE 65

To a stirred and refluxing mixture of 3.7 parts of 4-[[3-[(4-fluorophenyl)methyl]-3H-imidazo[4,5-b]pyridin-2-yl]methyl]-1-piperidineethanamine and 90 parts of methylbenzene were added dropwise 1.1 parts of 2-pyridinecarboxyaldehyde using a water separator. Upon completion, stirring was continued for 20 hours at reflux. After cooling to 50° C., 44 parts of ethanol were added. At a temperature of 40° C., 0.4 parts of sodium borohydride were added portionwise. Upon completion, the whole was stirred for 2 hours at 45° C. The reaction mixture was poured into ice water and acetic acid while hot. The mixture was treated with ammonium hydroxide. The product was extracted three times with methylbenzene. The organic layer was washed with water, dried, filtered and evaporated. The residue was purified by column chromatography over silica gel using a mixture of trichloromethane, methanol and ammonium hydroxide (90:9:1 by volume) as eluent. The pure fractions were collected and the eluent was evaporated. The residue was converted into the (E)-2-butenedioate salt in 2-propanone. The salt was filtered off and dried, yielding 3.0 parts (43.4%) of N-[2-[4-[[3-[(4-fluorophenyl)methyl]-3H-imidazo[4,5-b]pyridin-2-yl]methyl]-1-piperidinyl]ethyl]-2-pyridinemethanamine (E)-2-butenedioate(1:2); mp. 160.7° C. (425).

In a similar manner there were also prepared:
4-[[1-[(4-fluorophenyl)methyl]-1H-benzimidazol-2-yl]methyl]-N-(phenylmethyl)-1-piperidineethanamine (426); and N-[2-[4-[[1-[(4-fluorophenyl)methyl]-1H-benzimidazol-2-yl]methyl]-1-piperidinyl]ethyl]-2-pyridinemethanamine (E)-2-butenedioate(1:2); mp. 145.1° C. (427).

EXAMPLE 66

A mixture of 1.1 parts of isothiocyanatomethane, 5.5 parts of 4-[[1-[(4-fluorophenyl)methyl]-1H-benzimidazol-2-yl]methyl]-1-piperidineethanamine and 90 parts of tetrahydrofuran was stirred overnight at room temperature. The reaction mixture was evaporated. The residue was purified by column chromatography over silica gel using a mixture of trichloromethane and methanol (90:10 by volume) as eluent. The pure fractions were collected and the eluent was evaporated. The residue was converted into the ethanedioate salt in ethanol. The salt was filtered off and dried, yielding 4 parts (43%) of N-[2-[4-[[1-[(4-fluorophenyl)methyl]-1H-benzimidazol-2-yl]methyl]-1-piperidinyl]ethyl]-N'-methylthiourea ethanedioate (1:2); mp. 169.0° C. (428).

In a similar manner there were also prepared:
N-ethyl-N'-[2-[4-[[3-[(4-fluorophenyl)methyl]-3H-imidazo[4,5-b]pyridin-2-yl]-methyl]-1-piperidinyl]ethyl]urea; mp. 148.6° C. (429); and N-ethyl-N'-[2-[4-[[1-[(4-fluorophenyl)methyl]-1H-benzimidazol-2-yl]methyl]-1-piperidinyl]ethyl]urea; mp. 111.4° C. (430).

EXAMPLE 67

To a stirred mixture of 1.92 parts of 3-thiophenecarboxylic acid, 3.03 parts of N,N-diethylethanamine and 260 parts of dichloromethane were added 3.82 parts of 2-chloro-1-methylpyridinium iodide. The whole was stirred for 1 hour and then 5.5 parts of 4-[[1-[(4-fluorophenyl)methyl]-1H-benzimidazol-2-yl]methyl]-1-piperidineethanamine were added. After stirring for 2 hours, water was added and the product was extracted with dichloromethane. The combined extracts were washed twice with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in ethanol and acetonitrile. The salt was filtered off and crystallized from methanol. The product was filtered off and dried, yielding 3.5 parts (35.5%) of N-[2-[4-[[1-[(4-fluorophenyl)methyl]-1H-benzimidazol-2-yl]methyl-1-piperidinyl]ethyl]-3-thiophenecarboxamide ethanedioate(1:2); mp. 177.9° C. (431).

In a similar manner there were also prepared:

N-[2-[4-[[3-[(4-fluorophenyl(methyl]-3H-imidazo[4,5-b]pyridin-2-yl]methyl]-1-piperidinyl]ethyl]-3-furancarboxamide; mp. 139.9° C. (432);

N-[2-[4-[[1-[(4-fluorophenyl)methyl]-1H-benzimidazol-2-yl]methyl]-1-piperidinyl]ethyl]-1-methyl-1H-pyrrole-2-carboxamide ethanedioate (2:5); mp. 164.9° C. (433);

N-[2-[4-[[1-[(4-fluorophenyl)methyl]-1H-benzimidazol-2-yl]methyl]-1-piperidinyl]ethyl]-3-furancarboxamide ethanedioate(2:5).hemihydrate; mp. 139.7° C. (434);

[2-[4-[[3-[(4-fluorophenyl)methyl]-3H-imidazol[4,5-b]pyridin-2-yl]methyl]-1-piperidinyl]ethyl]-3-pyridinecarboxylate ethanedioate (1:3); mp. 149.3° C. (435);

3-amino-N[2-[4-[[1-[(4-fluorophenyl)methyl]-1H-benzimidazol-2-yl]methyl]-1-piperidinyl]ethyl]-2-pyrazinecarboxamide ethanedioate (1:2); mp. 166.8° C. (436);

N-[2-[4-[[1-[(4-fluorophenyl)methyl]-1H-benzimidazol-2-yl]methyl]-1-piperidinyl]ethyl]-4-thiazolecarboxamide ethanedioate(1:2); mp. 168.1° C. (437);

N-[2-[4-[[1-[(4-fluorophenyl)methyl]-1H-benzimidazol-2-yl]methyl]-1-piperidinyl]ethyl]-2-methoxy-3-pyridinecarboxamide ethanedioate (2:5); mp. 182.7° C. (438);

N-[2-[4-[[1-[(4-fluorophenyl)methyl]-1H-benzimidazol-2-yl]methyl]-1-piperidinyl]ethyl-a-oxo-2-thiopheneacetamide ethanedioate(1:2); mp. 180.2° C. (439); (439);

N-[2-[4-[[1-[(4-fluorophenyl)methyl]-1H-benzimidazol-2-yl]methyl]-1-piperidinyl]ethyl]-3-thiopheneacetamide ethanedioate(2:5); mp. 185.5° C. (440);

N-[2-[4-[[1-[(4-fluorophenyl)methyl]-1H-benzimidazol-2-yl]methyl]-1-piperidinyl]ethyl]-2-methoxy-5-(1-oxobutyl)benzamide ethanedioate (1:2).hemihydrate; mp. 161.3° C. (441);

N-[2-[4-[[1-[(4-fluorophenyl)methyl]-1H-benzimidazol-2-yl]methyl]-1-piperidinyl]ethyl]-1-methyl-1H-indole-2-carboxamide; mp. 137.3° C. (442);

N-[2-[4-[[1-[(4-fluorophenyl)methyl]-1H-benzimidazol-2-yl]methyl]-1-piperidinyl]ethyl]-2-thiophenecarboxamide ethanedioate(1:2); mp. 157.6° C. (443);

N-[2-[4-[[1-[(4-fluorophenyl)methyl]-1H-benzimidazol-2-yl]methyl]-1-piperidinyl]ethyl]-4-hydroxy-2-quinolinecarboxamide; mp. 262.4° C. (444);

N-[2-[4-[[1-[(4-fluorophenyl)methyl]-1H-benzimidazol-2-yl]methyl]-1-piperidinyl]ethyl]-2-oxo-2H-1-benzopyran-3-carboxamide; mp. 134.0° C. (445);

N-[2-[4-[[1-[(4-fluorophenyl)methyl]-1H-benzimidazol-2-yl]methyl]-1-piperidinyl]ethyl]-2-thiazolecarboxamide ethanedioate(1:2); mp. 178.0° C. (446); and N-[2-[4-[[1-[(4-fluorophenyl)methyl]-1H-benzimidazol-2-yl]methyl]-1-piperidinyl]ethyl]-4-pyridinecarboxamide ethanedioate(1:3) monohydrate; mp. 164.3° C. (447).

EXAMPLE 68

A mixture of 5.5 parts of 4-[[3-[(4-fluorophenyl)methyl]-3H-imidazo[4,5-b]pyridin-2-yl]methyl]-1-piperidineethanamine, 2.6 parts of 1,1'-carbonylbis[1H-imidazole] and 180 parts of tetrahydrofuran was stirred for 2 hours at room temperature. Gazeous N-methylmethanamine was bubbled through this mixture for 30 minutes (exothermic reaction: the cooler was provided with a $CaCl_2$ tube). The whole was stirred overnight at room temperature. The reaction mixture was evaporated. The residue was converted into the ethanedioate salt in 2-propanone. The precipitate was filtered off and the filtrate was evaporated. The residue was taken up in water. Ammonium hydroxide was added till an alkaline solution was obtained. The product was extracted twice with methylbenzene. The combined extracts were washed with water, dried, filtered and evaporated. The residue was purified by column chromatography over silica gel using a mixture of trichloromethane, methanol and ammonium hydroxide (90:9:1 by volume) as eluent. The pure and the less pure fractions were collected and the eluent was evaporated. The residue was purified by column chromatography (HPLC) over silica gel using a mixture of trichloromethane, methanol and methanol, saturated with ammonia, (96:3:1 by volume) as eluent. The pure fractions were collected and the eluent was evaporated using a water bath at 30° C. The residue was converted into the ethanedioate salt in 2-propanone. The salt was allowed to crystallize while stirring. It was filtered off and dried in vacuo at 60° C., yielding 2.0 parts (20.0%) of N'-[2-[4-[[3-[(4-fluorophenyl)methyl]-3H-imidazo[4,5-b]pyridin-2-yl]methyl]-1-piperidinyl]ethyl]-N,N-dimethylurea ethanedioate(2:5); mp. 94.2° C. (448).

EXAMPLE 69

A mixture of 25 parts of 1-[(4-fluorophenyl)methyl]-2-[[1-(2-isothiocyanatoethyl)-4-piperidinyl]methyl]-1H-benzimidazole and 160 parts of methanol saturated with ammonia was stirred overnight at room temperature. The reaction mixture was evaporated, yielding 25 parts (100%) of N-[4-[(1-[(4-fluorophenyl)methyl]-1H-benzimidazol-2-yl]methyl]-1-piperidinyl]ethyl]thiourea (449).

EXAMPLE 70

A mixture of 6.4 parts of methyl N-(2,2-dimethoxyethyl)-N'-methylcarbamimdothioate monohydroiodide, 7.3 parts of 4-[[1-[(4-fluorophenyl)methyl]-1H-benzimidazol-2-yl]methyl]-1-piperidineethanamine and 80 parts of 2-propanol was stirred and refluxed overnight.

The reaction mixture was evaporated, yielding 12.77 parts (99%) of N-(2,2-dimethoxyethyl)-N'-[2-[4-[[1-[(4-fluorophenyl)methyl]-1H-benzimidazol-2-yl]methyl]-1-piperidinyl]ethyl]-N"-methylguanidine monohydroiodide (450).

In a similar manner there were also prepared:
N-(2,2-dimethoxyethyl)-N'-[2-[4-[[1-[(4-fluorophenyl)methyl]-1H-benzimidazol-2-yl]methyl]-1-piperidinyl]ethyl]guanidine monohydroiodide (451).

EXAMPLE 71

A mixture of 12.77 parts of N-(2,2-dimethoxyethyl)-N'-[2-[4-[[1-[(4-fluorophenyl)methyl]-1H-benzimidazol-2-methyl]-1-piperidinyl]ethyl]-N"-methylguanidine monohydroiodide and 150 parts of a hydrochloric acid solution 10% was stirred and refluxed for 2 hours. Ice water was added and the whole was treated with a sodium hydroxide solution. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in ethanol. The salt was filtered off and dried, yielding 3 parts (21%) of 4-[[1-[(4-fluorophenyl)methyl]-1H-benzimidazol-2-yl]methyl]-N-(1-methyl-1H-imidazol-2-yl)-1-piperidineethanamine (E)-2-butenedioate (1:2) monohydrate; mp. 119.6° C. (452).

In a similar manner there were also prepared:
4-[[1-[(4-fluorophenyl)methyl]-1H-benzimidazol-2-yl]methyl]-N-(1H-imidazol-2-yl)-1-piperidineethanamine ethanedioate(1:2).monohydrate mp. 126.1° C. (453).

EXAMPLE 72

A mixture of 3.3 parts of 2-bromo-1-phenylethanone, 7 parts of N-[2-[4-[[1-[(4-fluorophenyl)methyl]-1H-benzimidazol-2-yl]methyl]-1-piperidinyl]ethyl]thiourea, 4 parts of potassium carbonate and 90 parts of tetrahydrofuran was stirred for 2 hours at room temperature. The reaction mixture was filtered over Hyflo and the filtrate was evaporated. The reaction mixture was poured into water. The product was extracted with dichloromethane. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 2.8 parts (33.3%) of 4-[[1-[(4-fluorophenyl)methyl]-1H-benzimidazol-2-yl]methyl]-N-(4-phenyl-2-thiazolyl)-1-piperidineethanamine; mp. 122.2° C. (454).

In a similar manner there were also prepared: ethyl 2-[(2-[4-[(1-[(4-fluorophenyl)methyl]-1H-benzimidazol-2-yl]methyl]-1-piperidinyl]ethyl]amino]-4-thiazolecarboxylate ethanedioate(1:2); mp. 179.5° C. (455); and 4-[(1-[(4-fluorophenyl)methyl]-1H-benzimidazol-2-yl]methyl]-N-(4-methyl-2-thiazolyl)-1-piperidineethanamine ethanedioate (2:7); mp. 148.6° C. (456).

EXAMPLE 73

A mixture of 6 parts of ethyl 4-[[1-[(4-fluorophenyl)methyl]-1H-benzimidazol-2-yl]methyl]-1-piperidineacetate and 120 parts of a hydrochloric acid solution 6N was stirred and refluxed overnight. The reaction mixture was cooled and filtered. The filtrate was evaporated and the semi-solid residue was taken up in about 120 parts of 2-propanol. The solution was filtered and about 70 parts of 2,2'-oxybispropane were added to the filtrate. After stirring for 2 hours at room temperature, the precipitated product was filtered off, dried overnight in vacuo at 80° C. and pulverized in a mortar, yielding 3 parts (52%) of 4-[[1-[(4-fluorophenyl)methyl]-1H-benzimidazol-2-yl]methyl]-1-piperidineacetic acid dihydrochloride. monohydrate; mp. 207.4° C. (457).

EXAMPLE 74

A mixture of 85 parts of 4-[4-[[1-[(4-fluorophenyl)methyl]-1H-benzimidazol-2-yl]methyl]-1-piperidinyl]-2-butanone and 600 parts of acetic acid was acidified with glacial acetic acid saturated with hydrogen bromide. A solution of 32.6 parts of bromine in acetic acid was added dropwise. Upon completion, stirring was continued overnight at room temperature. The reaction mixture was evaporated. The residue was stirred in 4-methyl-2-pentanone. The product was filtered off and dried, yielding 111 parts (80%) of 1-bromo-4-[4-[[1-[(4-fluorophenyl)methyl]-1H-benzimidazol-2-yl]methyl]-1-piperidinyl]-2-butanone trihydrobromide (458).

EXAMPLE 75

A mixture of 0.75 parts of ethanethioamide, 7 parts of 1-bromo-4-[4-[[1-[(4-fluorophenyl)methyl]-1H-benzimidazol-2-yl]methyl]-1-piperidinyl]-2-butanone dihydrobromide and 80 parts of methanol was stirred overnight at room temperature. The reaction mixture was evaporated. Water was added. The whole was treated with sodium hydroxide. The product was extracted with dichloromethane. The extract was dried, filtered and evaporated. The residue was purified by column chromatography over silica gel using a mixture of trichloromethane and methanol, saturated with ammonia, (97:3 by volume) as eluent. The pure fractions were collected and the eluent was evaporated. The residue was further purified by column chromatography (HPLC) over silica gel using a mixture of hexane, trichloromethane and methanol (45:45:10 by volume) as eluent. The pure fractions were collected and the eluent was evaporated. The residue was converted into the ethanedioate salt in ethanol and 2-propanone. The salt was filtered off and dried, yielding 2 parts (33%) of 1-[(4-fluorophenyl)methyl]-2-[[1-[2-(2-methyl-4-thiazolyl)ethyl]-4-piperidinyl]methyl]-1H-benzimidazole ethanedioate(2:5); mp. 124.1° C. (459).

EXAMPLE 76

To a stirred mixture of 5.5 parts of 4-[[1-[(4-fluorophenyl)methyl]-1H-benzimidazol-2-yl]methyl]-1-piperidineethanamine and 90 parts of tetrahydrofuran was added dropwise a solution of 3.8 parts of methyl 2-isothiocyanatobenzenecarboxylate in 18 parts of tetrahydrofuran (exothermic reaction). Upon completion, stirring was continued for 1 hour. The reaction mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and recrystallized from methanol. The product was filtered off and dried, yielding 3.6 parts (46%)

of 3-[2-[4-[[1-[(4-fluorophenyl)methyl]-1H-benzimidazol-2-yl]methyl]-1-piperidinyl]ethyl]-2,3-dihydro-2-thioxo-4(1H)-quinazolinone; mp. 218.2° C. (460).

In a similar manner there were also prepared:

3-[2-[4-[[1-(2-furanylmethyl)-1H-benzimidazol-2-yl]methyl]-1-piperidinyl]ethyl]-2,3-dihydro-2-thioxo-4(1H)-quinazolinone; mp. 216.6° C. (461);

3-[2-[4-[[1-[(4-fluorophenyl)methyl]-1H-benzimidazol-2-yl]methyl]-1-piperidinyl]ethyl]-2,3-dihydro-6-methyl-2-thioxothieno[2,3-d]pyrimidin-4(1H)-one dihydrochloride. monohydrate; mp. 224.3° C. (462);

3-[2-[4-[[3-[(4-fluorophenyl)methyl]-3H-imidazo[4,5-b]pyridin-2-yl]methyl]-1-piperidinyl]ethyl]-2,3-dihydro-2-thioxo-4(1H)quinazolinone; mp. 204.2° C. (463);

3-[2-[4-[[1-(2-furanylmethyl)-1H-benzimidazol-2-yl]methyl]-1-piperidinyl]-ethyl]-2,3-dihydro-6-methyl-2-thioxothieno[2,3-d]pyrimidin-4(1H)-one; mp. 192.7° C. (464); and 3-[2-[4-[[3-(2-furanylmethyl)-3H-imidazo[4,5-b]pyridin-2-yl]methyl]-1-piperidinyl]ethyl]-2,3-dihydro-6-methyl-2-thioxothieno[2,3-d]-pyrimidin-4(1H)-one; mp. 197.1° C. (465).

EXAMPLE 77

To a stirred mixture of 4.9 parts of 2H-3,1-benzoxazine-2,4(1H)-dione and 45 parts of N,N-dimethylformamide were added dropwise 10.15 parts of 4-[[1-(2-furanylmethyl)-1H-benzimidazol-2-yl]methyl]-1-piperidineethanamine and 45 parts of C at 50° C. Upon completion, stirring was continued for 4 hours at 70° C. After cooling, the reaction mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from 1,1'-oxybisethane. The product was filtered off and dried, yielding 10 parts (73%) of 2-amino-N-[2-[4-[[1-(2-furanylmethyl)-1H-benzimidazol-2-yl]methyl]-1-piperidinyl]ethyl]benzamide; mp. 125.7° C. (466).

In a similar manner there were also prepared:

N-[2-[4-[[1-[(4-fluorophenyl)methyl]-1H-benzimidazol-2-yl]methyl]-1-piperidinyl]ethyl]-2-(methylamino)-benzamide; mp. 84.3° C. (467);

2-amino-N-[2-[4-[[1-[(4-fluorophenyl)methyl]-1H-benzimidazol-2-yl]methyl]-1-piperidinyl]ethyl]benzamide; mp. 126.9° C. (468);

2-amino-N-[2-[4-[[3-[(4-fluorophenyl)methyl]-3H-imidazo[4,5-b]pyridin-2-yl]methyl]-1-piperidinyl]ethyl]benzamide (469);

N-[2-[4-[3-[(4-fluorophenyl)methyl]-3H-imidazo[4,5-b]pyridin-2-yl]methyl]-1-piperidinyl]ethyl]-2-(methylamino)benzamide ethanedioate (2:5); mp. 172.3° C. (470);

2-amino-N-[4-[4-[[1-[(4-fluorophenyl)methyl]-1H-benzimidazol-2-yl]methyl]-1-piperidinyl]butyl]benzamide (471);

2-amino-N-[4-[4-[[1-(2-furanylmethyl)-1H-benzimidazol-2-yl]methyl]-1-piperidinyl]butyl]benzamide; mp. 127.7° C. (472);

2-amino-N-[4-[[3-(2-furanylmethyl)-3H-imidazo[4,5-b]pyridin-2-yl]methyl]-1-piperidinyl]ethyl]benzamide; mp. 137.1° C. (473);

N-[2-[4-[[3-(2-furanylmethyl)-3H-imidazo[4,5-b]pyridin-2-yl]methyl]-1-piperidinyl]ethyl]-2-(methylamino)benzamide; mp. 81.4° C. (474); and 2-amino-N-[4-[4-[[3-(2-furanylmethyl)-3H-imidazo[4,5-b]pyridin-2-yl]methyl]-1-piperidinyl]butyl]benzamide (475);

N-[2-[4-[[1-(2-furanylmethyl)-1H-benzimidazol-2-yl]methyl]-1-piperidinyl]-ethyl]-2-(methylamino)benzamide (476);

2-amino-N-[2-[4-[[3-[(4-fluorophenyl)methyl]-3H-imidazo[4,5-c]pyridin-2-yl]-methyl]-1-piperidinyl]-ethyl]benzamide ethanedioate(1:2); mp. 161.5° C. (477);

2-amino-N-[2-[4-[[1-(2-thienylmethyl)-1H-benzimidazol-2-yl]methyl]-1-piperidinyl]ethyl]benzamide; mp. 143.5° C.; (478);

2,3-dihydro-2,2-dimethyl-3-[2-[4-[[3-(2-pyridinylmethyl)-3H-imidazo[4,5-b]-pyridin-2-yl]methyl]-1-piperidinyl]ethyl]-4(1H)-quinazolinone ethanedioate(1:1); mp. 210.2° C. (479); and 2-amino-N-[2-[4-[[1-[(4-fluorophenyl)methyl]-1H-benzimidazol-2-yl]oxy]-1-piperidinyl]ethyl]benzamide; mp. 141.7° C. (480).

EXAMPLE 78

A mixture of 4 parts of 2-amino-N-[2-[4-[[1-[(4-fluorophenyl)methyl]-1H-benzimidazol-2-yl)methyl]-1-piperidinyl]ethyl]benzamide, 20 parts of acetic acid anhydride and 40 parts of water was stirred and heated overnight at 120° C. After cooling, ice water was added. The whole was treated with ammonium hydroxide. The product was extracted with dichloromethane. The extract was dried, filtered and evaporated. The residue was converted into the (E)-2-butenedioate salt in ethanol. The salt was filtered off and dried, yielding 3.7 parts (72%) of 3-[2-[4-[[1-[(4-fluorophenyl)methyl]-1H-benzimidazol-2-yl]methyl]-1-piperidinyl]ethyl]-2-methyl-4(3H)-quinazolinone (E)-2-butenedioate (1:1); mp. 210.3° C. (481).

Following the same procedure and using equivalent amounts of the appropriate starting materials, there were also prepared:

3-[2-[4-[[1-(2-furanylmethyl)-1H-benzimidazol-2-yl]methyl]-1-piperidinyl]ethyl]-2-methyl-4(3H)-quinazolinone trihydrochloride. dihydrate; mp. 219.5° C. (482);

3-[2-[4-[[3-[(4-fluorophenyl)methyl]-3H-imidazo[4,5-b]pyridin-2-yl]methyl]-1-piperidinyl]ethyl]-2-methyl-4(3H)-quinazolinone; mp. 147.6° C. (483); and 3-[2-[4-[[3-(2-furanylmethyl)-3H-imidazo[4,5-b]pyridin-2-yl]methyl]-1-piperidinyl]ethyl]-2-methyl-4(3H)-quinazolinone (E)-2-butenedioate (1:3); mp. 184.1° C. (484).

EXAMPLE 79

A mixture of 5 parts of 2-amino-N-[2-[4-[[1-[(4-fluorophenyl)methyl]-1H-benzimidazol-2-yl]oxy]-1-piperidinyl]ethyl]-benzamide, 80 parts of 2-propanone and 1.9 parts of ethanedioic acid was stirred for 1 hour at reflux temperature. After cooling, the product was filtered off and dried, yielding 4.8 parts (77%) of 3-[2-[4-[[1-[(4-fluorophenyl)methyl]-1H-benzimidazol-2-yl]oxy]-1-piperidinyl]ethyl]-2,3-dihydro-2,2-dimethyl-4(1H)-quinazolinone ethanedioate (1:1); mp. 166.5° C. (485).

EXAMPLE 80

To a stirred mixture of 8 parts of N-[2-[4-[[3-(2-furanylmethyl)-3H-imidazo[4,5-b]pyridin-2-yl]methyl]-1-piperidinyl]ethyl]-2-(methylamino)benzamide, 13 parts of N,N-diethylethanamine and 130 parts of dichloromethane was added dropwise a solution of 2.3 parts of carbonothioic dichloride in dichloromethane. Upon completion, stirring was continued for 2 hours. The reaction mixture was evaporated. The residue was crystallized from a mixture of methanol and ethanol. The product was filtered off and boiled in methanol. The product was filtered off and dried, yielding 3 parts (34.3%) of
3-[2-[4-[[3-(2-furanylmethyl)-3H-imidazo[4,5-b]pyridin-2-yl]methyl]-1-piperidinyl]ethyl]-2,3-dihydro-1-methyl-2-thioxo-4(1H)-quinazolinone; mp. 169.2° C. (486).

In a similar manner there were also prepared:
3-[2-[4-[[1-[(4-fluorophenyl)methyl]-1H-benzimidazol-2-yl]methyl]-1-piperidinyl]ethyl]-2,3-dihydro-1-methyl-2-thioxo-4(1H)quinazolinone; mp. 147.5° C. (487); and
3-[2-[4-[[3-[(4-fluorophenyl)methyl]-3H-imidazo[4,5-b]pyridin-2-yl]methyl]-1-piperidinyl]ethyl]-2,3-dihydro-1-methyl-2-thioxo-4(1H)quinazolinone; mp. 176.1° C. (488).

EXAMPLE 81

A mixture of 10.3 parts of 2-amino-N-[4-[4-[[1-[(4-fluorophenyl)methyl]-1H-benzimidazol-2-yl]methyl]-1-piperidinyl]-butyl]benzamide, 3.2 parts of 1,1'-carbonylbis[1H-imidazole] and 180 parts of tetrahydrofuran was stirred and refluxed overnight. The reaction mixture was evaporated. The residue was purified by column chromatography over silica gel using first a mixture of trichloromethane and methanol saturated with ammonia (97:3 by volume) and then a mixture of trichloromethane and methanol saturated with ammonia (95:5 by volume) as eluent. The pure fractions were collected and the eluent was evaporated. The residue was crystallized from 2-propanone, yielding 3.8 parts (35.5%) of 3-[4-[4-[[1-[(4-fluorophenyl)methyl]-1H-benzimidazol-2-yl]methyl]-1-piperidinyl]butyl]-2,4(1H,3H)-quinazolinedione; mp. 187.3° C. (489).

EXAMPLE 82

To a stirred mixture of 3.88 parts of 2-amino-N-[4-[4-[[1-(2-furanylmethyl)-1H-benzimidazol-2-yl]methyl]-1-piperidinyl]butyl]benzamide, 2 parts of N,N-diethylethanamine and 90 parts of tetrahydrofuran were added dropwise 1.64 parts of trichloromethyl carbonochloridate. Upon completion, stirring was continued overnight. Another portion of 1.6 parts of B was added and the whole was stirred overnight. The precipitate was filtered off and the filtrate was evaporated. Water was added to the residue. The solution was treated with ammonium hydroxide; The product was extracted with dichloromethane. The extract was dried, filtered and evaporated. The residue was crystallized from acetonitrile. The product was filtered off and dried, yielding 3 parts (73%) of 3-[4-[4-[[1-(2-furanylmethyl)-1H-benzimidazol-2-yl]methyl]-1-piperidinyl]butyl]-2,4(1H,3H)-quinazolinedione; mp. 185.5° C. (490).

In a similar manner there was also prepared:
3-[4-[4-[[3-(2-furanylmethyl)-3H-imidazo[4,5-b]pyridin-2-yl]methyl]-1-piperidinyl]butyl]-2,4-(1H,3H)-quinazolinedione; mp. 146.6° C. (491).

EXAMPLE 82

To a stirred mixture of 5.1 parts of 4-[[3-(2-furanylmethyl)-3H-imidazo[4,5-b]pyridin-2-yl]methyl]-1-piperidineethanamine and 270 parts of tetrahydrofuran was added dropwise a solution of 3.8 parts of ethyl 2-isothiocyanatobenzoate in tetrahydrofuran. Upon completion, stirring was continued for 1 hour. The reaction mixture was evaporated. The residue was purified by column chromatography over silica gel using a mixture of trichloromethane and methanol, saturated with ammonia, (97:3 by volume) as eluent. The pure fractions were collected and the eluent was evaporated. The residue was crystallized from 2-propanone. The product was filtered off and dried, yielding 1.4 parts (18.6%) of 3-[2-[4-[[3-(2-furanylmethyl)-3H-imidazo[4,5-b]pyridin-2-yl]methyl]-1-piperidinyl]ethyl]-2,3-dihydro-2-thioxo-4(1H)-quinazolinone; mp. 192.0° C. (492).

EXAMPLE 84

A mixture of 6 parts of $N^1$-[2-[4-[[1-[(4-fluorophenyl)methyl]-1H-benzimidazol-2-yl]methyl]-1-piperidinyl]ethyl]-1,2-benzenediamine, 2.7 parts of 1,1'-thiocarbonylbis[1H-imidazole] and 90 parts of tetrahydrofuran was stirred and refluxed for 1 hour. The reaction mixture was evaporated. The residue was purified by column chromatography over silica gel using a mixture of trichloromethane and methanol (95:5 by volume) as eluent. The pure fractions were collected and the eluent was evaporated. The oily residue was stirred in acetonitrile. The product was filtered off and crystallized from ethanol. The product was filtered off and dried, yielding 2.8 parts (41.5%) of 1-[2-[4-[[1-[(4-fluorophenyl)methyl]-1H-benzimidazol-2-yl]methyl]-1-piperidinyl]ethyl]-1,3-dihydro-2H-benzimidazole-2-thione; mp. 157.1° C. (493).

EXAMPLE 85

A mixture of 7.5 parts of 6-chloro-$N^4$-[2-[4-[[1-[(4-fluorophenyl)methyl]-1H-benzimidazol-2-yl]methyl]-1-piperidinyl]ethyl]-4,5-pyrimidinediamine and 3.6 parts of urea was stirred and heated for 20 minutes at 220° C. Water was added to the reaction mixture. The precipitated product was filtered off and crystallized from methanol. The product was filtered off and recrystallized from a mixture of N,N-dimethylformamide and methanol, yielding 2.5 parts (32%) of 6-chloro-9-[2-[4-[[1-[(4-fluorophenyl)methyl]-1H-benzimidazol-2-yl]methyl]-1-piperidinyl]ethyl]-9H-purin-8-ol; mp. 243.0° C. (494).

EXAMPLE 86

A mixture of 11.3 parts of $N^4$-[2-[4-[[1-[(4-fluorophenyl)methyl]-1H-benzimidazol-2-yl]methyl]-1-piperidinyl]ethyl]-4,5-pyrimidinediamine, 3.75 parts of carbon disulfide and 117 parts of N,N-dimethylformamide was stirred overnight at room temperature. The reaction mixture was poured into water. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 5 parts (40%) of 9-[2-[4-[[1-[(4-fluorophenyl)methyl]-1H-benzimidazol-2-yl]methyl]-1-piperidinyl]ethyl]-9H-purine-8-thiol; mp. 163.7° C. (495).

EXAMPLE 87

To a stirred mixture of 3 parts of 3-[2-[4-[[3-(2-furanylmethyl)-3H-imidazo[4,5-b]pyridin-2-yl]methyl]-1-piperidinyl]ethyl]-2,3-dihydro-6-methyl-2-thioxothieno[2,3-d]pyrimidin-4(1H)-one, 4.3 parts of potassium hydroxide, 56 parts of ethanol and 5.5 parts of water were added dropwise 45 parts of a hydrogen peroxide solution 3%. The whole was stirred overnight. The reaction mixture was evaporated. The residue was purified by column chromatography over silica gel using a mixture of trichloromethane and methanol (90:10 by volume) as eluent. The pure fractions were collected and the eluent was evaporated. The residue was crystallized from 2-propanone. The product was filtered off and dried, yielding 1.7 parts (58%) of 3-[2-[4-[[3-(2-furanylmethyl)-3H-imidazo[4,5-b]pyridin-2-yl]methyl]-1-piperidinyl]ethyl]-6-methylthieno[2,3-d]pyrimidine-2,4(1H,3H)-dione monohydrate; mp. 135.4° C. (496).

In a similar manner there was also prepared:

3-[2-[4-[[1-[(4-fluorophenyl)methyl]-1H-benzimidazol-2-yl]methyl]-1-piperidinyl]ethyl]-6-methyl-thieno[2,3-d]pyrimidine-2,4-(1H,3H)dione dihydrochloride. dihydrate; mp. 232.8° C. (497).

EXAMPLE 88

A mixture of 2.5 parts of 3-[2-[4-[[1-[(4-fluorophenyl)methyl]-1H-benzimidazol-2-yl]methyl]-1-piperidinyl]ethyl]-2-methyl-4H-pyrido[1,2-a]pyrimidin-4-one and 120 parts of methanol was hydrogenated at normal pressure and at room temperature with 1 part of palladium-on-charcoal catalyst 10%. After the calculated amount of hydrogen was taken up, the catalyst was filtered off and the filtrate was evaporated. The residue was converted into the ethanedioate salt in ethanol. The salt was filtered off and dried, yielding 3 parts (87%) of 3-[2-[4-[[1-[(4-fluorophenyl)methyl]-1H-benzimidazol-2-yl]methyl]-1-piperidinyl]ethyl]-6,7,8,9-tetrahydro-2-methyl-4H-pyrido[1,2-a]pyrimidin-4-one ethanedioate (1:2); mp. 192.7° C. (498).

EXAMPLE 89

A mixture of 2.4 parts of 5-chloro-N-[2-[4-[[1-[(4-fluorophenyl)methyl]-1H-benzimidazol-2-yl]methyl]-1-piperidinyl]ethyl]-2-pyridinamine, 1 part of calcium oxide and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. Water was added to the residue. The product was extracted with 4-methyl-2-pentanone. The extract was dried, filtered and evaporated. The residue was converted into the ethanedioate salt in a mixture of acetonitrile and ethanol. The salt was filtered off and dried in a dry pistol at 110°–120° C., yielding 1.8 parts (50%) of N-[2-[4-(4-fluorophenyl)methyl]-1H-benzimidazol-2-yl]methyl]-1-piperidinyl]ethyl]-2-pyridinamine ethanedioate; mp. 156.2° C. (499).

In a similar manner there were also prepared:

N-[2-[4-[[1-[(4-fluorophenyl)methyl]-1H-benzimidazol-2-yl]methyl]-1-piperidinyl]ethyl]-3-pyridazinamine trihydrochloride.monohydrate; mp. 197.9° C. (500);

N-[2-[4-[[1-[(4-fluorophenyl)methyl]-1H-benzimidazol-2-yl]methyl]-1-piperidinyl]ethyl]-4-pyrimidinamine; mp. 60.3° C. (501);

9-[2-[4-[[1-[(4-fluorophenyl)methyl]-1H-benzimidazol-2-yl]methyl]-1-piperidinyl]ethyl]-9H-purin-8-ol; mp. 213.6° C. (502);

$N^4$-[2-[4-[[1-[(4-fluorophenyl)methyl]-1H-benzimidazol-2-yl]methyl]-1-piperidinyl]ethyl]-4,5-pyrimidinediamine (503).

EXAMPLE 90

A mixture of 7.7 parts of 1-[(4-fluorophenyl)methyl]-2-[[1-[2-(4-methoxyphenyl)ethyl]-4-piperidinyl]methyl]-1H-benzimidazole and 150 parts of a hydrobromic acid solution 48% in water was stirred overnight at 80° C. The reaction mixture was evaporated and water was added to the residue. The whole was treated with ammonium hydroxide and the product was extracted with trichloromethane. The extract was dried, filtered and evaporated. The residue was purified by column chromatography HPLC) over silica gel using a mixture of hexane, trichloromethane and methanol (45:45:10 by volume) as eluent. The pure fractions were collected and the eluent was evaporated. The residue was crystallized from acetonitrile. The product was filtered off and dried, yielding 2.5 parts (35%) of 4-[2-[4-[[1-[(4-fluorophenyl)methyl]-1H-benzimidazol-2-yl]methyl]-1-piperidinyl]ethyl]phenol; mp. 130.3° C. (504).

In a similar manner there were also prepared:

1-[(4-fluorophenyl)methyl]-2-[[1-[2-(4-hydroxyphenyl)ethyl]-4-piperidinyl]-methyl]-1H-benzimidazol-6-ol monohydrate; mp. 169.4° C. (505).

EXAMPLE 91

A mixture of 7 parts of 4-[[1-[(4-fluorophenyl]methyl]-1H-benzimidazol-2-yl]methyl]-N-(2-nitrophenyl)-1-piperidineethanamine, 1 part of a solution of thiophene in methanol 4% and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 6 parts (90%) of $N^1$-[2-[4-[[1-[(4-fluorophenyl)methyl]-1H-benzimidazol-2-yl]methyl]-1-piperidinyl]ethyl]-1,2-benzenediamine (506).

EXAMPLE 92

To a stirred mixture of 34.5 parts of 9-[2-[4-[[1-[(4-fluorophenyl)methyl]-1H-benzimidazol-2-yl]methyl]-1-piperidinyl]ethyl]-9H-purine-8-thiol and 180 parts of N,N-dimethylformamide were added portionwise 3.2 parts of a sodium hydride dispersion 50%. Upon completion, stirring was continued for 0.5 hours at room temperature. 11.5 Parts of iodomethane were added dropwise. After complete addition, the whole was stirred for 1 hour. The reaction mixture was poured into water. The product was extracted with 4-methyl-2-pentanone. The extract was dried, filtered and evaporated. The residue was crystallized from acetonitrile. The product was filtered off and dried, yielding 28.3 parts (80%) of 9-[2-[4-[[1-[(4-fluorophenyl)methyl]-1H-benzimidazol-2-yl]methyl]-1-piperidinyl]ethyl]-8-(methylthio)-9H-purine; mp. 133.1° C. (507).

EXAMPLE 93

To a stirred and cooled mixture of 6.2 parts of N-[2-[4-[[1-[(4-fluorophenyl)methyl]-1H-benzimidazol-2-yl]methyl]-1-piperidinyl]ethyl]-2-pyridinamine, 2 parts of N,N-diethylethanamine and 90 parts of tetrahydrofuran was added dropwise slowly a solution of 1.9 parts of benzoyl chloride in 45 parts of tetrahydrofuran. Upon completion, stirring was continued for 2 hours. The reaction mixture was evaporated. Water was added to the residue. The solution was treated with ammonium hydroxide. The product was extracted with 4-methyl-2-pentanone. The extract was dried, filtered and evaporated. The residue was crystallized from 2,2'-oxybispropane. The product was filtered off and dried, yielding 5.3 parts (69%) of N-[2-[4-[[1-[(4-fluorophenyl)methyl]-1H-benzimidazol-2-yl]methyl]-1-piperidinyl]ethyl]-N-(2-pyrimidinyl)benzamide; mp. 108.1° C. (508).

In a similar manner there were also prepared:
N-[2-[4-[[1-(2-furanylmethyl)-1H-benzimidazol-2-yl]methyl]-1-piperidinyl]-ethyl]-N-(2-pyrimidinyl)-2-furancarboxamide ethanedioate (1:2); mp. 147.7° C. (509).

EXAMPLE 94

A mixture of 6.6 parts of N-[2-[4-[[1-[(4-fluorophenyl)methyl]-1H-benzimidazol-2-yl]methyl]-1-piperidinyl]ethyl]-2-pyrimidinamine, 20 parts of acetic acid anhydride and 60 parts of water was stirred and refluxed overnight. The reaction mixture was evaporated. Water was added and the whole was treated with ammonium hydroxide. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in 2-propanone. The salt was filtered off and dried, yielding 2.7 parts (27%) of N-[2-[4-[[1-[(4-fluorophenyl)methyl]-1H-benzimidazol-2-yl]methyl]-1-piperidinyl]ethyl]-N-(2-pyrimidinyl)acetamide ethanedioate (1:2); mp. 173.7° C. (510).

EXAMPLE 95

A mixture of 2.9 parts of N-[2-[4-[[1-(2-furanylmethyl)-1H-benzimidazol-2-yl]methyl]-1-piperidinyl]-ethyl]-2-(methylamino)benzamide, 10 parts of acetic acid anhydride and 20 parts of water was stirred and heated for 3 hours at 100° C. The reaction mixture was cooled, water was added and the whole was made alkaline with ammonium hydroxide. The product was extracted with dichloromethane. The extract was dried, filtered and evaporated. The residue was purified twice by column chromatography over silica gel using each time a mixture of trichloromethane and methanol, saturated with ammonia (95:5 by volume) as eluent. The pure fractions were collected and the eluent was evaporated. The residue was converted into the ethanedioate salt in ethanol, yielding 0.2 parts (4.3%) of 2-(acetylmethylamino)-N-[2-[4-[[1-(2-furanylmethyl)-1H-benzimidazol-2-yl[-methyl]-1-piperidinyl]ethyl]benzamide ethanedioate (2:5); mp. 146.8° C. (511).

EXAMPLE 96

A mixture of 13.4 parts of 4-[[1-[(4-fluorophenyl)methyl]-1H-benzimidazol-2-yl]methyl]-N-(phenylmethyl)-1-piperidineethanamine, 4 parts of poly(oxymethylene), 1 part of a solution of thiophene in methanol 4% and 120 parts of methanol was hydrogenated at normal pressure and at room temperature with 2 parts of palladium-on-charcoal catalyst 5%. After the calculated amount of hydrogen was taken up, the catalyst was filtered off and the filtrate was evaporated. The residue was taken up in 4-methyl-2-pentanone. The solution was washed with water, dried, filtered and evaporated. The residue was converted into the ethanedioate salt in methanol. The salt was filtered off and dried, yielding 13.02 parts (68.3%) of 4-[[1-[(4-fluorophenyl)methyl]-1H-benzimidazol-2-yl]methyl]-N-methyl-N-(phenylmethyl-1-piperidine-ethanamine ethanedioate (1:2); mp 172.6° C. (512).

A mixture of 10 parts of 4-[[1-[(4-fluorophenyl)methyl]-1H-benzimidazol-2-yl]methyl]-N-methyl-N-(phenylmethyl)-1-piperidineethanamine and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was converted into the ethanedioate salt in methanol. The salt was filtered off and dried, yielding 7 parts (87.8%) of 4[[1-[(4-fluorophenyl)methyl]-1H-benzimidazol-2-yl]methyl]-N-methyl-1-piperidineethanamine ethanedioate(1:2); mp. 205.8° C. (dec.) (513).

A mixture of 1.8 parts of 2-chloropyrimidine, 6 parts of 4-[[1-[(4-fluorophenyl)methyl]-1H-benzimidazol-2-yl]methyl]-N-methyl-1-piperidineethanamine, 1.7 parts of sodium hydrogen carbonate and 120 parts of ethanol was stirred and refluxed overnight. The reaction mixture was evaporated. Water was added. The product was extracted with 4-methyl-2-pentanone. The extract was dried, filtered and evaporated. The residue was crystallized from a mixture of 2,2'-oxybisprospane and 1,1'-oxybisethane (50:50 by volume). The product was filtered off and dried, yielding 5.5 parts (76.5%) of N-[2-[4-[[1-[(4-fluorophenyl)methyl]-1H-benzimidazol-2-yl]methyl]-1-piperidinyl]ethyl]-N-methyl-2-pyrimidinamine; mp. 135.4° C. (514).

EXAMPLE 97

To a stirred mixture of 3.5 parts of 2-[[1-[2-(4-methoxyphenyl)ethyl]-4-piperidinyl]methyl]-1H-benzimidazole and 18 parts of N,N-dimethylacetamide were added portionwise 0.5 parts of a sodium hydride dispersion 59.4% at room temperature. After stirring for 35 minutes at room temperature and for 10 minutes at 60° C., a solution of 1.7 parts of 1-(chloromethyl)-2-fluorobenzene in 9 parts of N,N-dimethylacetamide was added dropwise at 60° C. After stirring for 10 minutes, the reaction mixture was cooled and poured into 150 parts of water. The product was extracted twice with 4-methyl-2-pentanone. The combined extracts were washed with water, dried, filtered and evaporated. The residue was crystallized from a mixture of 2,2'-oxybispropane and 2-propanone. The product was filtered off and dried, yielding 3.0 parts (65.5%) of 1-[(2-fluorophenyl)methyl]-2-[[1-[2-(4-methoxyphenyl)ethyl]-4-piperidinyl]-methyl]-1H-benzimidazole; mp. 109.3° C. (515).

In a similar manner there are also prepared:
2-[[1-[2-(4-methoxyphenyl)ethyl]-4-piperidinyl]methyl]-1-(2-phenylethyl)-1H-benzimidazole dihydrochloride, monohydrate; mp. 176.0° C. (516);
1-(diphenylmethyl)-2-[[1-[2-(4-methoxyphenyl)ethyl]-4-piperidinyl]methyl]-1H-benzimidazole ethanedioate (2:5); mp. 174.0° C. (517);
1-[(2,5-dimethylphenyl)methyl]-2-[[1-[2-(4-methoxyphenyl)ethyl]-4-piperidinyl]methyl]-1-H-benzimidazole; mp. 118.3° C. (518);
1-[(2,6-dichlorophenyl)methyl]-2-[[1-[2-(4-methoxyphenyl)ethyl]-4-piperidinyl]methyl]-1H-benzimidazole; mp. 152.4° C. (519);
1-[(3-chlorophenyl)methyl]-2-[[1-[2-(4-methoxyphenyl)ethyl]-4-piperidinyl]-methyl]-1H-benzimidazole dihydrochloride; mp. 173.3° C. (520);

2-[[1-[2-(4-methoxyphenyl)ethyl]-4-piperidinyl]methyl]-1-(1-naphthalenyl-methyl)-1H-benzimidazole ethanedioate(2:5); mp. 186.8° C. (521);

1-cyclohexyl-2-[[1-[2-(4-methoxyphenyl)ethyl]-4-piperidinyl]methyl]-1H-benzimidazole dihydrochloride.monohydrate; mp. 189.6° C. (522);

2-[[1-[2-(4-methoxyphenyl)ethyl]-4-piperidinyl]methyl]-1-(3-thienylmethyl)-1H-benzimidazole ethanedioate(1:2); mp. 185.5° C. (523);

2-[[1-[2-(4-methoxyphenyl)ethyl]-4-piperidinyl]methyl]-1-(2-pyrazinylmethyl)-1H-benzimidazole (E)-2-butenedioate(1:1); mp. 180.9° C. (524);

2-[[1-[2-(4-methoxyphenyl)ethyl]-4-piperidinyl]methyl]-1-[(5-methyl-2-thienyl)-methyl]-1H-benzimidazole ethanedioate(1:2); mp. 194.9° C. (525); and 2-[[1-[2-(4-methoxyphenyl)ethyl]-4-piperidinyl]methyl]-1-[(3-methyl-2-thienyl)methyl]-1H-benzimidazole ethanedioate(1:2).monohydrate; mp. 166.2° C. (526).

EXAMPLE 98

Following the procedures described in Example 18 and using the appropriate starting materials there were also prepared:

5,6-dimethoxy-2-[[1-(phenylmethyl)-4-piperidinyl]methyl]-1H-benzimidazole; mp. 160.6° C. (527); and 6-chloro-5-methoxy-2-[[1-(phenylmethyl)-4-piperidinyl]methyl]-1H-benzimidazole; mp. 190.0° C. (528).

Following the procedures described in Example 18 and using the appropriate starting materials there are also prepared:

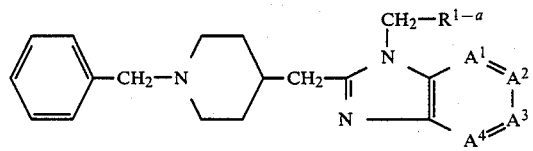

| No. | $R^{1-a}$ | $A^1=A^2-A^3=A^4$ |
|---|---|---|
| 529 | 4-F—C$_6$H$_4$— | CH=CH—CH=C(OCH$_3$) |
| 530 | 4-F—C$_6$H$_4$— | C(OCH$_3$)=CH—CH=CH |
| 531 | 2-furanyl | CH=CH—C(OCH$_3$)=CH |
| 532 | 2-furanyl | CH=C(OCH$_3$)—CH=CH |
| 533 | 2-pyridinyl | CH=CH—C(OCH$_3$)=CH |
| 534 | 2-pyridinyl | CH=C(OCH$_3$)—CH=CH |
| 535 | 4-F—C$_6$H$_4$— | N=C(OCH$_3$)—CH=CH |
| 536 | 2-furanyl | N=C(OCH$_3$)—CH=CH |
| 537 | 2-pyridinyl | N=C(OCH$_3$)—CH=CH |

EXAMPLE 99

Folowing the procedures described in Example 25 and using the appropriate starting materials there were also prepared:

1-[(4-fluorophenyl)methyl]-5,6-dimethoxy-2-[[1-(phenylmethyl)-4-piperidinyl]-methyl]-1H-benzimidazole ethanedioate(1:2); mp. 169.0° C.; (538);

5-chloro-1-[(4-fluorophenyl)methyl]-6-methoxy-2-[[1-(phenylmethyl)-4-piperidinyl]methyl]-1H-benzimidazole; mp. 131.9° C. (539); and 6-chloro-1-[(4-fluorophenyl)methyl]-5-methoxy-2-[[1-(phenylmethyl)-4-piperidinyl]methyl]-1H-benzimidazole ethanedioate(½)mp. 181.8° C. (540).

EXAMPLE 100

Following the procedures described in Example 26 and using the appropriate starting materials there was also prepared:

1-[(4-fluorophenyl)methyl]-5,6-dimethoxy-2-(4-piperidinylmethyl)-1H-benzimidazole ethanedioate(1:2); mp. 161.1° C. (541).

Following the procedures described in Example 26 and using the appropriate starting materials there are also prepared:

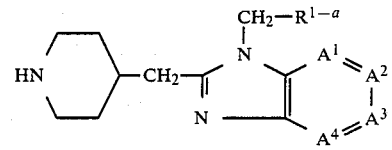

| No. | $R^{1-a}$ | $A^1=A^2-A^3=A^4$ |
|---|---|---|
| 542 | 4-F—C$_6$H$_4$— | CH=CH—CH=C(OCH$_3$) |
| 543 | 4-F—C$_6$H$_4$— | C(OCH$_3$)=CH—CH=CH |
| 544 | 2-furanyl | CH=CH—C(OCH$_3$)=CH |
| 545 | 2-furanyl | CH=C(OCH$_3$)—CH=CH |
| 546 | 2-pyridinyl | CH=CH—C(OCH$_3$)=CH |
| 547 | 2-pyridinyl | CH=C(OCH$_3$)—CH=CH |
| 548 | 4-F—C$_6$H$_4$— | N=C(OCH$_3$)—CH=CH |
| 549 | 2-furanyl | N=C(OCH$_3$)—CH=CH |
| 550 | 2-pyridinyl | N=C(OCH$_3$)—CH=CH |

EXAMPLE 101

Following the procedures described in Example 29 and using the appropriate starting materials there were also prepared:

ethyl 4-[[5-chloro-1-[(4-fluorophenyl)methyl]-6-methoxy-1H-benzimidazol-2-yl]methyl]-1-piperidinecarboxylate (551); and ethyl 4-[[6-chloro-1-[(4-fluorophenyl)methyl]-5-methoxy-1H-benzimidazol-2-yl]methyl]-1-piperidinecarboxylate (552).

EXAMPLE 102

Following the procedures described in Example 30 and using the appropriate starting materials there were also prepared:

5-chloro-1-[(4-fluorophenyl)methyl]-6-methoxy-2-(4-piperidinylmethyl)-1H-benzimidazole as a residue (553); and 6-chloro-1-[(4-fluorophenyl)methyl]-5-methoxy-2-(4-piperidinylmethyl)-1H-benzimidazole as a residue (554).

EXAMPLE 103

Following the procedures described in Example 34 and using the appropriate starting materials there are also prepared:

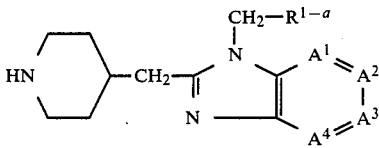

| No. | $R^{1-a}$ | $A^1=A^2—A^3=A^4$ |
|---|---|---|
| 555 | 4-F—C$_6$H$_4$— | CH=CH—CH=C(OH) |
| 556 | 4-F—C$_6$H$_4$— | C(OH)=CH—CH=CH |
| 557 | 4-F—C$_6$H$_4$— | CH=C(OH)—C(OH)=CH |

-continued

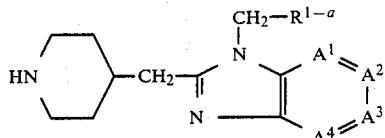

| No. | R¹⁻ᵃ | A¹=A²—A³=A⁴ |
|---|---|---|
| 558 | 4-F—C₆H₄— | CH=C(OH)—CCl=CH |
| 559 | 4-F—C₆H₄— | CH=CCl—C(OH)=CH |
| 560 | 2-furanyl | CH=CH—C(OH)=CH |
| 561 | 2-furanyl | CH=C(OH)—CH=CH |
| 562 | 2-pyridinyl | CH=CH—C(OH)=CH |
| 563 | 2-pyridinyl | CH=C(OH)—CH=CH |
| 564 | 4-F—C₆H₄— | N=C(OH)—CH=CH |
| 565 | 2-furanyl | N=C(OH)—CH=CH |
| 566 | 2-pyridinyl | N=C(OH)—CH=CH |

EXAMPLE 104

Following the procedures described in Example 37 and using the appropriate starting materials there was also prepared:
1-[(4-fluorophenyl)methyl]-2-[[1-[2-(2-pyridinyl)ethyl]-4-piperidinyl]methyl]-1H-benzimidazol-6-ol; mp. 197.5° C. (567).

EXAMPLE 105

Following the procedures described in Example 39 and using the appropriate starting materials there were also prepared:
1-[(4-fluorophenyl)methyl]-2-[[1-[2-(2-thienyl)ethyl]-4-piperidinyl]methyl]-1H-benzimidazol-5-ol; mp. 199.2° C. (568); and
1-[(4-fluorophenyl)methyl]-2-[[1-[2-(2-thienyl)ethyl]-4-piperidinyl]methyl]-1H-benzimidazol-6ol; mp. 212.1° C. (569).

EXAMPLE 106

A mixture of 6.48 parts of [(2-bromoethyl)thio]benzene, 6.8 parts of 1-[(4-fluorophenyl)methyl]-2-(4-piperidinylmethyl)-1H-benzimidazol-5-ol, 4.2 parts of sodium carbonate and 120 parts of 4-methyl-2-pentanone was stirred for 2 hours at reflux temperature using a water separator. After cooling to room temperature, the reaction mixture was poured into water. The layers were separated. The organic layer was washed with 500 parts of water, dried, filtered and evaporated. The residue was taken up in a mixture of trichloromethane and methanol (95:5 by volume) and 25 parts of silica gel. After stirring for 15 minutes, the whole was filtered, washed with the eluent and the filtrate was evaporated. The residue was boiled in 160 parts of 2-propanone. The mixture was stirred overnight at room temperature. The product was filtered off, washed with 2-propanone and crystallized from 280 parts of 2-propanone. The product was filtered off, washed with 2-propanone and dried in vacuo at 50° C., yielding 2.7 parts (27.8%) of 1-[(4-fluorophenyl)methyl]-2-[[1-[2-(phenylthio)ethyl]-4-piperidinyl]methyl]-1-H-benzimidazol-5-ol hemihydrate; mp. 193.8° C. (570).

Following the same procedure and using the appropriate starting materials there were also prepared:
3-[2-[4-[[1-[(4-fluorophenyl)methyl]-5-hydroxy-1H-benzimidazol-2-yl]methyl]-1-piperidinyl]ethyl]-6,7,8,9-tetrahydro-2-methyl-4H-pyrido-[1,2-a]pyrimidin-4-one; mp. 189.2° C. (571);
1-[(4-fluorophenyl)methyl]-2-[[1-[2-(4-methoxyphenyl)ethyl]-4-piperidinyl]methyl]-1H-benzimidazole as a residue (572);
1-[(4-fluorophenyl)methyl]-2-[[1-[2-(phenylthio)ethyl]-4-piperidinyl]methyl]-1H-benzimidazol-6-ol; mp. 179.7° C. (573);
3-[2-[4-[[1-[(4-fluorophenyl)methyl]-6-hydroxy-1-H-benzimidazol-2yl]methyl]-1-piperidinyl]ethyl]2-methyl-4H-pyrido[1,2-a]pyrimidin-4-one; mp. 217.1° C. (574);
3-[2-[4-[[1-[(4-fluorophenyl)methyl]-6-hydroxy-1H-benzimidazol-2-yl]methyl]-1-piperidinyl]ethyl]-6,7,8,9-tetrahydro-2-methyl-4H-pyrido[1,2-a]pyrimidin-4-one; mp. 183.4° C. (575); and
3-[2-[4-[[1-[(4-fluorophenyl)methyl]-6-hydroxy-1H-benzimidazol-2-yl]methyl]-1-piperidinyl]ethyl]-2,4(1H,3H)-pyrimidinedione; mp. 253.5° C. (576).

EXAMPLE 107

Following the procedures described in Example 46 and using the appropriate starting materials there were also prepared:
3-[2-[4-[[1-[(4-fluorophenyl)methyl]-5-hydroxy-1H-benzimidazol-2-yl]methyl]-1-piperidinyl]ethyl]-2-methyl-4-H-pyrido[1,2-a]pyrimidin-4-one ethanedioate(1:2); mp. 212.8° C. (577);
3-[2-[4-[[1-[(4-fluorophenyl)methyl]-5,6-dimethoxy-1H-benzimidazol-2-yl]-methyl]-1-piperidinyl]ethyl]-2-methyl-4H-pyrido[1,2-a]pyrimidin-4-one ethanedioate(1:2); mp. 163.6° C. (578);
5-chloro-1-[(4-fluorophenyl)methyl]-6-methoxy-2-[[1-[2-(4-methoxyphenyl)ethyl]-4-piperidinyl]methyl]-1H-benzimidazole (E)-2-butenedioate(1:2); mp. 210.3° C. (579);
6-chloro-1-[(4-fluorophenyl)methyl]-5-methoxy-2-[[1-[2-(4-methoxyphenyl)ethyl]-4-piperidinyl]methyl]-1H-benzimidazole ethanedioate (2:5); mp. 198.6° C. (580);
1-[(4-fluorophenyl)methyl]-2-[[1-[2-(2-methoxyphenyl)ethyl]-4-piperidinyl]-methyl]-1H-benzimidazol-5-ol (E)-2-butenedioate(2:1); mp. 214.6° C. (581);
1-[(4-fluorophenyl)methyl]-5,6-dimethoxy-2-[[1-[2-(4-methoxyphenyl)ethyl]-4-piperidinyl]methyl]-1H-benzimidazole ethanedioate(1:2); mp. 177.6° C. (582);
2-[[1-[2-(3,4-dimethoxyphenyl)ethyl]-4-piperidinyl]methyl]-1-[(4-fluorophenyl)-methyl]-6-methoxy-1H-benzimidazole ethanedioate (1:2); mp. 171.9° C. (583);
1-[(4-fluorophenyl)methyl]-6-methoxy-2-[[1-[2-(3-methoxyphenyl)ethyl]4-piperidinyl]methyl]-1H-benzimidazole ethanedioate(1:2); mp. 194.2° C. (584);
1-[(4-fluorophenyl)methyl]-6-methoxy-2-[[1-[2-(2-methoxyphenyl)ethyl]-4-piperidinyl]methyl]-1H-benzimidazole (E)-2-butenedioate(2:3); mp. 190.5° C. (585);
1-[3-[4-[[1-[(4-fluorophenyl)methyl]-6-hydroxy-1H-benzimidazol-2-yl]methyl]-1-piperidinyl]propyl]-1,3-dihydro-2H-benzimidazol-2-one; mp. 186.2° C. (586);
1-[3-[4-[[1-[(4-fluorophenyl)methyl]-5-hydroxy-1H-benzimidazol-2-yl]methyl]-1-piperidinyl]propyl]-1,3-dihydro-2H-benzimidazol-2-one; mp. 175.2° C. (587);
3-[2-[4-[[1-[(4-fluorophenyl)methyl]-6-hydroxy-1H-benzimidazol-2-yl]methyl]-1-piperidinyl]ethyl]-2,4-(1H,3H)-quinazolinedione; mp. 181.6° C. (588);
In a similar manner there are also prepared:

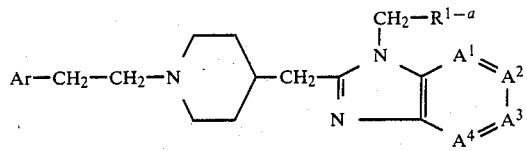

| No. | Ar | $R^{1-a}$ | $A^1=A^2-A^3=A^4$ |
|---|---|---|---|
| 589 | 4-CH$_3$O—C$_6$H$_4$ | 4-F—C$_6$H$_4$— | CH=CH—CH=C(OH) |
| 590 | 4-CH$_3$O—C$_6$H$_4$ | 4-F—C$_6$H$_4$— | CH=CH—C(OH)=CH |
| 591 | 4-CH$_3$O—C$_6$H$_4$ | 4-F—C$_6$H$_4$— | C(OH)=CH—CH=CH |
| 592 | 4-CH$_3$O—C$_6$H$_4$ | 4-F—C$_6$H$_4$— | CH=C(OH)—C(OH)=CH |
| 593 | 3,4-(CH$_3$O)$_2$—C$_6$H$_3$— | 4-F—C$_6$H$_4$— | CH=CH—C(OH)=CH |
| 594 | 3,4-(CH$_3$O)$_2$—C$_6$H$_3$— | 4-F—C$_6$H$_4$— | CH=C(OH)—CH=CH |
| 595 | 3-CH$_3$O—C$_6$H$_4$— | 4-F—C$_6$H$_4$— | CH=CH—C(OH)=CH |
| 596 | 3-CH$_3$O—C$_6$H$_4$— | 4-F—C$_6$H$_4$— | CH=C(OH)—CH=CH |
| 597 | 4-CH$_3$O—C$_6$H$_4$— | 2-furanyl | CH=CH—C(OH)=CH |
| 598 | 4-CH$_3$O—$_6$H$_4$— | 2-furanyl | CH=C(OH)—CH=CH |
| 599 | 4-CH$_3$O—C$_6$H$_4$— | 2-pyridinyl | CH=CH—C(OH)=CH |
| 600 | 4-CH$_3$O—C$_6$H$_4$— | 2-pyridinyl | CH=C(OH)—CH=CH |
| 601 | 4-CH$_3$O—C$_6$H$_4$ | 4-F—C$_6$H$_4$— | N=CH—CH=CH |
| 602 | 4-CH$_3$O—C$_6$H$_4$— | 2-pyridinyl | N=CH—CH=CH |
| 603 | 4-CH$_3$O—C$_6$H$_4$— | 2-furanyl | N=CH—CH=CH |
| 604 | 4-CH$_3$O—C$_6$H$_4$— | 4-F—C$_6$H$_4$— | N=C(OH)—CH=CH |
| 605 | 4-CH$_3$O—C$_6$H$_4$— | 2-pyridinyl | N=C(OH)—CH=CH |
| 606 | 4-CH$_3$O—C$_6$H$_4$— | 2-furanyl | N=C(OH)—CH=CH |
| 607 | 2-CH$_3$O—C$_6$H$_4$— | 4-F—C$_6$H$_4$— | CH=C(OH)—CH=CH |
| 608 | 4-CH$_3$O—C$_6$H$_4$ | 4-F—C$_6$H$_4$— | CH=CH—CH=C(OCH$_3$) |
| 609 | 4-CH$_3$O—C$_6$H$_4$ | 4-F—C$_6$H$_4$— | CH=CH—C(OCH$_3$)=CH |
| 610 | 4-CH$_3$O—C$_6$H$_4$ | 4-F—C$_6$H$_4$— | C(OCH$_3$)=CH—CH=CH |
| 611 | 4-CH$_3$O—C$_6$H$_4$ | 4-F—C$_6$H$_4$— | CH=CCl—C(OCH$_3$)=CH |
| 612 | 4-CH$_3$O—C$_6$H$_4$ | 4-F—C$_6$H$_4$— | CH=C(OCH$_3$)—CCl=CH |
| 613 | 3,4-(CH$_3$O)$_2$—C$_6$H$_3$— | 4-F—C$_6$H$_4$— | CH=CH—C(OCH$_3$)=CH |
| 614 | 3-CH$_3$O—C$_6$H$_4$— | 4-F—C$_6$H$_4$— | CH=CH—C(OCH$_3$)=CH |
| 615 | 4-CH$_3$O—C$_6$H$_4$— | 2-furanyl | CH=CH—C(OCH$_3$)=CH |
| 616 | 4-CH$_3$O—C$_6$H$_4$— | 2-furanyl | CH=C(OCH$_3$)—CH=CH |
| 617 | 4-CH$_3$O—C$_6$H$_4$— | 2-pyridinyl | CH=CH—C(OCH$_3$)=CH |
| 618 | 4-CH$_3$O—C$_6$H$_4$— | 2-pyridinyl | CH=C(OCH$_3$)—CH=CH |
| 619 | 4-CH$_3$O—C$_6$H$_4$— | 4-F—C$_6$H$_4$— | N=C(OCH$_3$)—CH=CH |
| 620 | 4-CH$_3$O—C$_6$H$_4$— | 2-pyridinyl | N=C(OCH$_3$)—CH=CH |
| 621 | 4-CH$_3$O—C$_6$H$_4$— | 2-furanyl | N=C(OCH$_3$)—CH=CH |
| 622 | 2-CH$_3$O—C$_6$H$_4$— | 4-F—C$_6$H$_4$— | CH=CH—C(OCH$_3$)=CH |

In a similar manner there are also prepared:

| No. | L' | n | $A^1=A^2-A^3=A^4$ |
|---|---|---|---|
| 623 | benzimidazol-2(3H)-thione-1-yl | 2 | CH=C(OH)—CH=CH |
| 624 | benzimidazol-2(3H)-thione-1-yl | 2 | CH=CH—C(OH)=CH |
| 625 | benzimidazol-2(3H)-thione-1-yl | 2 | CH=C(OH)—C(OH)=CH |
| 626 | benzimidazol-2(3H)-thione-1-yl | 3 | CH=C(OH)—CH=CH |

-continued

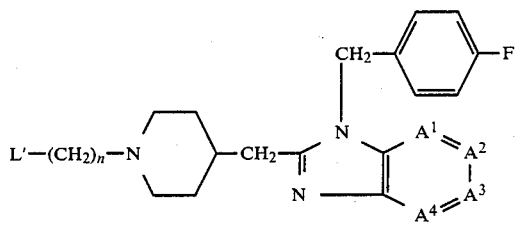

| No. | L' | n | A¹=A²—A³=A⁴ |
|---|---|---|---|
| 627 | (benzothiazol-2-yl-thione, HN-C(=S)-N<) | 3 | CH=CH—C(OH)=CH |
| 628 | (benzothiazol-2-yl-thione, HN-C(=S)-N<) | 3 | CH=C(OH)—C(OH)=CH |
| 629 | (benzimidazol-2(3H)-one, HN-C(=O)-N<) | 3 | CH=C(OH)—C(OH)=CH |
| 630 | 2-thienyl | 2 | CH=C(OH)—C(OH)=CH |
| 631 | (quinazoline-2,4-dione) | 2 | CH=CH—C(OH)=CH |
| 632 | (quinazoline-2,4-dione) | 2 | CH=C(OH)—C(OH)=CH |

EXAMPLE 108

A mixture of 6 parts of 5-chloro-1-[(4-fluorophenyl)-methyl]-6-methoxy-2-[[1-[2-(4-methoxyphenyl)ethyl]-4-piperidinyl]methyl]-1H-benzimidazole and 75 parts of a hydrobromic acid solution 48% in water was stirred and heated overnight at 80° C. Water and ammonium hydroxide were added. After stirring, the product was extracted with trichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the ethanedioate salt in ethanol. The salt was filtered off and dried, yielding 3.8 parts (49%) of 4-[2-[4-[[5-chloro-1-[(4-fluorophenyl)methyl]-6-methoxy-1H-benzimidazol-2-yl]methyl]-1-piperidinyl]ethyl]phenol ethanedioate(1:2); mp. 228.5° C. (633).

EXAMPLE 109

Following the procedures described in Example 90 and using equivalent amounts of the appropriate starting materials there were also prepared:

3-[2-[4-[[1-[(4-fluorophenyl)methyl]-5,6-dihydroxy-1H-benzimidazol-2-yl]-methyl]-1-piperidinyl]ethyl]-2-methyl-4H-pyrido[1,2-a]pyrimidin-4-one trihydrobromide; mp. 276.0° C. (634);

4-[2-[4-[[3-(2-pyridinylmethyl)-3H-imidazo[4,5-b]pyridin-2-yl]methyl]-1-piperidinyl]ethyl]phenol; mp. 167.1° C. (635);

4-[2-[4-[[3-[(4-fluorophenyl)methyl]-3H-imidazo[4,5-b]pyridin-2-yl]methyl]-1-piperidinyl]ethyl]phenol; mp. 191.1° C. (636);

1-[(4-fluorophenyl)methyl]-2-[[1-[2-(4-hydroxyphenyl)ethyl]-4-piperidinyl]-methyl]-1H-benzimidazol-5-ol dihydrobromide monohydrate; mp. 222.3° C. (637);

1-[(4-fluorophenyl)methyl]-2-[[1-[2-(4-hydroxyphenyl)ethyl]-4-piperidinyl]methyl]-1H-benzimidazole-5,6-diol dihydrobromide; mp. 231.8° C. (638);

6-chloro-1-[(4-fluorophenyl)methyl]-2-[[1-[2-(4-hydroxyphenyl)ethyl]-4-piperidinyl]methyl]-1H-benzimidazol-5-ol; mp. 241.7° C. (639);

5-chloro-1-[(4-fluorophenyl)methyl]-2-[[1-[2-(4-hydroxyphenyl)ethyl]-4-piperidinyl]methyl]-1H-benzimidazol-6-ol dihydrobromide; mp. 255.5° C. (640);

1-[(4-fluorophenyl)methyl]-2-[[1-[2-(3-hydroxyphenyl)ethyl]-4-piperidinyl]-methyl]-1H-benzimidazol-6-ol; mp. 250.8° C. (641);

1[(4-fluorophenyl)methyl]-2-[[1-[2-(2-hydroxyphenyl)ethyl]-4-piperidinyl]methyl]-1H-benzimidazol-5-ol; mp. 157.4° C. (642); and 1-[(4-fluorophenyl)methyl]-2-[[1-[2-(2-hydroxyphenyl)ethyl]-4-piperidinyl]-methyl]-1H-benzimidazol-6-ol; mp. 201.5° C. (643).

Following the procedures described in Example 90 and using equivalent amounts of the appropriate starting materials there are also prepared:

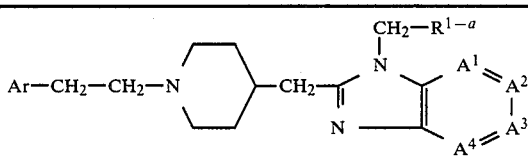

| No. | Ar | R¹⁻ᵃ | A¹=A²—A³=A⁴ |
|---|---|---|---|
| 644 | 4-HO—C₆H₄ | 4-F—C₆H₄— | CH=CH—CH=C(OH) |
| 645 | 4-HO—C₆H₄ | 4-F—C₆H₄— | C(OH)=CH—CH=CH |

-continued

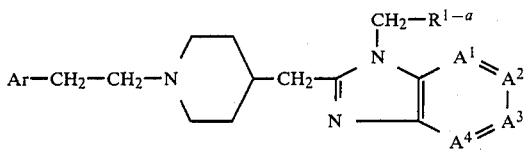

| No. | Ar | $R^{1-a}$ | $A^1=A^2-A^3=A^4$ |
|---|---|---|---|
| 646 | $4\text{-HO}-C_6H_4-$ | $4\text{-F}-C_6H_4-$ | $CH=CCl-C(OH)=CH$ |
| 647 | $3,4\text{-(HO)}_2-C_6H_3-$ | $4\text{-F}-C_6H_4-$ | $CH=CH-C(OH)=CH$ |
| 648 | $3,4\text{-(HO)}_2-C_6H_3-$ | $4\text{-F}-C_6H_4-$ | $CH=C(OH)-CH=CH$ |
| 649 | $3\text{-HO}-C_6H_4-$ | $4\text{-F}-C_6H_4-$ | $CH=CH-C(OH)=CH$ |
| 650 | $4\text{-HO}-C_6H_4-$ | 2-furanyl | $CH=CH-C(OH)=CH$ |
| 651 | $4\text{-HO}-C_6H_4-$ | 2-furanyl | $CH=C(OH)-CH=CH$ |
| 652 | $4\text{-HO}-C_6H_4-$ | 2-pyridinyl | $CH=CH-C(OH)=CH$ |
| 653 | $4\text{-HO}-C_6H_4-$ | 2-pyridinyl | $CH=C(OH)-CH=CH$ |
| 654 | $4\text{-HO}-C_6H_4-$ | $4\text{-F}-C_6H_4-$ | $N=CH-CH=CH$ |
| 655 | $4\text{-HO}-C_6H_4-$ | 2-pyridinyl | $N=CH-CH=CH$ |
| 656 | $4\text{-HO}-C_6H_4-$ | 2-furanyl | $N=CH-CH=CH$ |
| 657 | $4\text{-HO}-C_6H_4-$ | $4\text{-F}-C_6H_4-$ | $N=C(OH)-CH=CH$ |
| 658 | $4\text{-HO}-C_6H_4-$ | 2-pyridinyl | $N=C(OH)-CH=CH$ |
| 659 | $4\text{-HO}-C_6H_4-$ | 2-furanyl | $N=C(OH)-CH=CH$ |
| 660 | $2,4\text{-(HO)}_2-C_6H_3-$ | $4\text{-F}-C_6H_4-$ | $CH=CH-C(OH)=CH$ |
| 661 | $2,4\text{-(HO)}_2-C_6H_3-$ | $4\text{-F}-C_6H_4-$ | $CH=C(OH)-CH=CH$ |
| 662 | $2,4\text{-(HO)}_2-C_6H_3-$ | $4\text{-F}-C_6H_4-$ | $CH=C(OH)-C(OH)=CH$ |

The useful antihistaminic properties of the compounds of formula (I) are demonstrated in the following test procedure.

Protection of rats from compound 48/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240-260 g were used in the experiment. After overnight starvation the rats were transferred to conditioned laboratories (temp.=21±1° C., relative humidity=65+5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration. The $ED_{50}$-values of the compounds of formula (I) are listed in the first column of tables 1 to 4. Said $ED_{50}$-values are the values in mg/kg body weight at which the tested compounds protect 50% of the tested animals against compound 48/80-induced lethality. The compounds of formula (I) and the pharmaceutically acceptable acid addition salts thereof are also potent serotonin-antagonists. The potency of the subject compounds as serotonin-antagonists is clearly evidenced by the results obtained in the following tests wherein the antagonistic activity of the subject compounds on the effect of serotonin is examined.

Antagonistic activity on the effects of serotonin in the gastric lesion test.

A. Lesions induced by compound 48/80:

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1 antagonist. However the stimulatory effects on gastric secretion are not suppressed so that rats treated with compound 48/80 and protected from shock by an H 1 antagonist may exhibit all signs of intensive gastric gland activity: gross autopsy shows distended stomachs with abnormal contents and rough bright red patches all over the mucosa, corresponding to areas of disintegrated glands. A number of known serotonin-antagonists such as, for example, methysergide, cyproheptadine; cinanserin, mianserin, pipamperone, spiperone, pizotifen and metergoline, prevent completely the cyanosis of ears and extremities as well as the lesions in the glandular area of the stomach and the abnormal gastric distension.

B. Method:

Male rats of a Wistar inbred strain, weighing 220-250 g, were starved overnight, water being available ad libitum. The test compounds were administered orally as a solution or as a suspension in aqueous medium. A control rat and a "blank" rat received the test compound. One hour later 5-[4-(diphenylmethyl)1-piperazinylmethyl]-1-methyl-1H-benzimidazole-2-methanol was administered subcutaneously to all rats at the dose of 2.5 mg/kg. Two hours after the oral or subcutaneous administration of the test compound, the compound 48/80 (freshly solved in water at a concentration of 0.25 mg/ml) was injected intravenously into all rats (dose: 1 mg/kg) except the "blank" rats. Four hours after the intravenous injection of compound 48/80, the rats were decapitated and the stomachs were removed. Subsequently the stomachs were inspected for distension and contents (blood, fluid, food) and thoroughly rinsed. The macroscopic lesions were scored from 0 to +++, 0 corresponding to complete absence of visible lesions and the highest score corresponding to reddish rough patches covering more than half the glandular area.

The second column of tables 1–4 show for a number of compounds of formula (I) the doses (in mg/kg body weight) at which the distension of the stomach as well as the lesions in the glandular area of the stomach are completely absent in 50% of the test rats ($ED_{50}$-value).

The compounds listed in table 1 are not given for the purpose of limiting the invention thereto but only to exemplify the useful pharmacological activities of all the compounds within the scope of formula (I).

| Comp. No. | Compound 48/80 lethality test in rats $ED_{50}$ in mg/kg body weight | gastric lesion test $ED_{50}$ in mg/kg body weight |
|---|---|---|
| 8 | 0.04 | — |
| 23 | 0.08 | — |
| 25 | 0.16 | — |
| 34 | 0.04 | 0.63 |
| 40 | 0.08 | — |
| 42 | 0.02 | — |
| 45 | 0.04 | — |
| 47 | 0.08 | 0.63 |
| 48 | 0.16 | — |
| 50 | 0.04 | — |
| 59 | 0.02 | — |
| 64 | 0.04 | — |
| 66 | 0.02 | — |
| 81 | 0.08 | — |
| 82 | 0.005 | 0.63 |
| 83 | 0.01 | — |
| 85 | 0.01 | — |
| 86 | 0.01 | — |
| 89 | 0.04 | — |
| 90 | 0.01 | 0.31 |
| 93 | 0.04 | — |
| 94 | 0.08 | 0.63 |
| 96 | 0.04 | — |
| 98 | 0.04 | — |
| 99 | 0.04 | 0.31 |
| 100 | 0.16 | — |
| 101 | 0.02 | 0.31 |
| 102 | 0.02 | 0.31 |
| 103 | 0.005 | 0.16 |
| 104 | 0.08 | — |
| 105 | 0.01 | — |
| 107 | 0.04 | 0.08 |
| 110 | 0.02 | — |
| 112 | 0.08 | — |
| 113 | 0.08 | — |
| 115 | 0.16 | — |
| 116 | 0.16 | — |
| 117 | 0.01 | — |
| 118 | 0.04 | 0.63 |
| 123 | 0.01 | — |
| 124 | 0.04 | 0.31 |
| 126 | 0.04 | 0.63 |
| 127 | 0.08 | 0.63 |
| 128 | 0.16 | 0.63 |
| 129 | 0.16 | — |
| 130 | 0.16 | — |
| 131 | 0.02 | 0.16 |
| 133 | 0.02 | 0.16 |
| 134 | 0.04 | — |
| 139 | 0.08 | — |
| 140 | 0.04 | — |
| 142 | 0.02 | — |
| 143 | 0.04 | 0.63 |
| 144 | 0.04 | — |
| 145 | 0.02 | 0.16 |
| 147 | 0.08 | — |
| 149 | 0.04 | — |
| 151 | 0.02 | 0.16 |
| 152 | 0.04 | — |
| 154 | 0.08 | — |
| 158 | 0.04 | — |
| 161 | 0.04 | — |
| 162 | 0.08 | 0.31 |
| 163 | 0.02 | — |
| 164 | 0.02 | 0.02 |
| 165 | 0.02 | — |
| 166 | 0.04 | — |
| 167 | 0.01 | — |
| 168 | 0.04 | 0.63 |
| 169 | 0.02 | — |
| 170 | 0.08 | — |
| 171 | 0.08 | — |
| 173 | 0.01 | — |
| 174 | 0.01 | — |
| 175 | 0.02 | — |
| 176 | 0.04 | — |
| 177 | 0.04 | 0.31 |
| 178 | 0.02 | — |
| 180 | 0.01 | 0.31 |
| 181 | 0.04 | — |
| 182 | 0.04 | 0.63 |
| 183 | 0.01 | — |
| 184 | 0.02 | 0.63 |
| 186 | 0.04 | 0.31 |
| 187 | 0.04 | 0.31 |
| 189 | 0.02 | 0.63 |
| 198 | 0.04 | 0.08 |
| 202 | 0.08 | — |
| 203 | 0.04 | — |
| 204 | 0.08 | — |
| 205 | 0.08 | — |
| 207 | 0.08 | 0.08 |
| 208 | 0.04 | 0.08 |
| 209 | 0.08 | 0.63 |
| 214 | 0.08 | 0.04 |
| 215 | 0.08 | — |
| 216 | 0.04 | — |
| 218 | 0.04 | 0.04 |
| 219 | 0.08 | 0.63 |
| 221 | 0.04 | — |
| 224 | 0.04 | 0.08 |
| 226 | 0.08 | 0.04 |
| 228 | 0.04 | 0.01 |
| 229 | 0.04 | 0.63 |
| 232 | 0.08 | — |
| 234 | 0.02 | — |
| 236 | 0.08 | 0.63 |
| 238 | 0.08 | 0.63 |
| 243 | 0.04 | — |
| 244 | 0.16 | 0.31 |
| 245 | 0.02 | — |
| 248 | 0.04 | — |
| 255 | 0.16 | — |
| 256 | 0.08 | — |
| 257 | 0.02 | — |
| 258 | 0.08 | — |
| 259 | 0.08 | — |
| 260 | 0.01 | 0.63 |
| 261 | 0.08 | — |
| 262 | 0.04 | 0.16 |
| 263 | 0.04 | 0.04 |
| 264 | 0.04 | 0.63 |
| 265 | 0.02 | — |
| 266 | 0.04 | — |
| 268 | 0.16 | — |
| 270 | 0.08 | — |
| 272 | 0.08 | 0.63 |
| 273 | 0.01 | 0.31 |
| 274 | 0.16 | — |
| 276 | 0.04 | 0.31 |
| 283 | 0.04 | 0.63 |
| 290 | 0.08 | — |
| 293 | 0.08 | — |
| 297 | 0.08 | — |
| 328 | 0.16 | — |
| 329 | 0.31 | — |
| 330 | 0.08 | 0.16 |
| 331 | 0.04 | 0.02 |

-continued

| Comp. No. | Compound 48/80 lethality test in rats ED$_{50}$ in mg/kg body weight | gastric lesion test ED$_{50}$ in mg/kg body weight |
|---|---|---|
| 332 | 0.08 | 0.08 |
| 333 | 0.04 | — |
| 334 | 0.005 | 0.31 |
| 335 | 0.02 | 0.16 |
| 336 | 0.01 | 0.08 |
| 338 | 0.02 | — |
| 339 | 0.01 | — |
| 340 | 0.08 | — |
| 342 | 0.02 | 0.16 |
| 344 | 0.02 | — |
| 345 | 0.08 | — |
| 347 | 0.08 | 0.63 |
| 348 | 0.04 | 0.04 |
| 349 | 0.08 | — |
| 351 | 0.02 | 0.08 |
| 352 | 0.01 | — |
| 355 | 0.08 | — |
| 356 | 0.02 | 0.08 |
| 357 | 0.02 | 0.63 |
| 361 | 0.02 | — |
| 362 | 0.08 | 0.63 |
| 363 | 0.04 | — |
| 364 | 0.04 | — |
| 365 | 0.08 | — |
| 366 | 0.31 | — |
| 367 | 0.16 | 0.16 |
| 368 | 0.01 | — |
| 369 | 0.04 | — |
| 370 | 0.02 | — |
| 371 | 0.16 | 0.63 |
| 372 | 0.04 | 0.16 |
| 373 | 0.08 | — |
| 374 | 0.02 | 0.02 |
| 376 | 0.02 | 0.63 |
| 377 | 0.16 | — |
| 378 | 0.04 | — |
| 379 | 0.08 | 0.31 |
| 380 | 0.31 | 0.63 |
| 381 | 0.08 | 0.16 |
| 382 | 0.08 | 0.63 |
| 383 | 0.04 | 0.16 |
| 384 | 0.08 | 0.63 |
| 385 | 0.01 | 0.08 |
| 388 | 0.16 | — |
| 390 | 0.04 | — |
| 391 | 0.02 | 0.02 |
| 392 | 0.02 | 0.63 |
| 393 | 0.08 | — |
| 394 | 0.02 | — |
| 397 | 0.04 | 0.04 |
| 399 | 0.02 | 0.04 |
| 402 | 0.04 | — |
| 416 | 0.04 | 0.04 |
| 417 | 0.04 | — |
| 418 | 0.02 | 0.04 |
| 422 | 0.04 | 0.04 |
| 427 | 0.16 | — |
| 428 | 0.04 | 0.01 |
| 429 | 0.02 | — |
| 430 | 0.01 | 0.005 |
| 431 | 0.04 | 0.005 |
| 432 | 0.04 | 0.31 |
| 433 | 0.01 | 0.16 |
| 434 | 0.0025 | — |
| 436 | 0.01 | 0.63 |
| 438 | 0.08 | 0.16 |
| 439 | 0.16 | 0.31 |
| 440 | 0.02 | — |
| 441 | 0.08 | 0.16 |
| 443 | 0.02 | 0.16 |
| 444 | 0.16 | — |
| 445 | 0.16 | — |
| 448 | 0.08 | 0.16 |
| 452 | 0.16 | — |
| 453 | 0.04 | 0.02 |
| 455 | 0.04 | 0.63 |
| 456 | 0.01 | 0.63 |
| 459 | 0.02 | — |
| 460 | 0.08 | 0.63 |
| 461 | 0.08 | 0.08 |
| 463 | 0.08 | — |
| 466 | 0.02 | — |
| 467 | 0.04 | 0.08 |
| 468 | 0.02 | 0.63 |
| 470 | 0.04 | — |
| 472 | 0.04 | — |
| 473 | 0.02 | — |
| 477 | 0.02 | 0.63 |
| 478 | 0.02 | 0.04 |
| 479 | 0.04 | — |
| 480 | 0.02 | — |
| 489 | 0.08 | 0.63 |
| 490 | 0.31 | — |
| 491 | 0.16 | — |
| 493 | 0.08 | 0.04 |
| 495 | 0.04 | 0.16 |
| 498 | 0.08 | 0.16 |
| 499 | 0.04 | 0.01 |
| 500 | 0.01 | — |
| 501 | 0.04 | — |
| 502 | 0.08 | 0.16 |
| 504 | 0.08 | 0.63 |
| 505 | 0.04 | 0.04 |
| 507 | 0.16 | — |
| 508 | 0.08 | 0.16 |
| 509 | 0.02 | — |
| 510 | 0.02 | 0.16 |
| 511 | 0.16 | — |
| 512 | 0.08 | — |
| 513 | 0.08 | — |
| 514 | 0.02 | 0.63 |
| 515 | 0.16 | — |
| 516 | 0.16 | — |
| 523 | 0.04 | 0.31 |
| 524 | 0.16 | — |

In view of their antihistaminic and serotonin-antagonistic properties, the compounds of formula (I) and their acid-addition salts are very useful in the treatment of allergic diseases such as, for example, allergic rhinitis, allergic conjunctivities, chronic urticaria, allergic astma and the like.

In view of their useful antihistaminic and serotonin-antagonistic activity, the subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

"Active ingredient" (A.I.) as used throughout these examples relates to a compound of formula (I), a possible stereochemically isomeric form or pharmaceutically acceptable acid addition salt thereof.

EXAMPLE 110: ORAL DROPS

500 Grams of the A.I. was dissolved in 0.5 liters of 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 111: ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 112: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 113: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating

To a solution of 10 grams methyl cellulose in 75 milliliters of denatured ethanol there was added a solution of 5 grams of ethyl cellulose in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated.

The tablet cores were coated with the thus obtained mixture in a coating apparatus.

EXAMPLE 114: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 115: SUPPOSITORIES

3 Grams A.I. was dissolved in a solution of b 3 grams 2,3-dihydroxybutanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°–38° C. to form 100 suppositories each containing 30 milligrams of the active ingredient.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Suitable doses administered daily to subjects are varying from 0.1 to 100 mg, more preferably from 1 to 50 mg.

What we claim is:

1. A method of treating allergic diseases in warm-blooded animals suffering from same which method comprises the systemic administration to warm-blooded animals of an anti-allergic effective amount of a compound having the formula

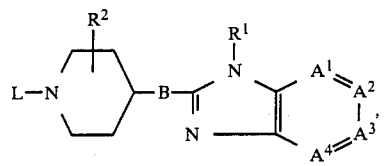

a pharmaceutically acceptable acid addition salt or a possible stereochemically isomeric form thereof, wherein:

$A^1=A^2-A^3=A^4$ is a bivalent radical having the formula

| —CH=CH—CH=CH— | (a-1), |
| —N=CH—CH=CH— | (a-2), |
| —CH=N—CH=CH— | (a-3), |
| —CH=CH—N=CH— | (a-4), or |
| —CH=CH—CH=N— | (a-5), | wherein one or two hydrogen atoms in said radicals (a-1)–(a-5) may, each independently from each other, be replaced by halo, lower alkyl, lower alkyloxy, trifluoromethyl or hydroxy;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen and lower alkyl;

B is $CH_2$, O, S, SO or $SO_2$;

L is a member selected from the group consisting of a radical of formula $$L^1-C_rH_{2r}-T-C_sH_{2s}- \quad (b-1); \text{ and}$$

a radical of formula

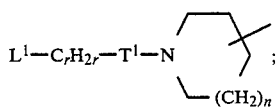

wherein one or two hydrogen atoms in the bivalent radical —$C_sH_{2s}$— may, each independently from each other, be replaced by halo, hydroxy, mercapto, isothiocyanato, isocyanato, lower alkyloxy, lower alkylthio, $Ar^1$, $Ar^1O$—, $Ar^1S$—, $Ar^1SO_2$—, or $NR^3R^5$; and n is 0 or the integer 1 or 2;

r and s are, independently from each other, 0 or an integer of from 1 to 6 inclusive;

T is

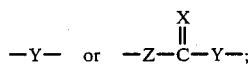

$T^1$ is

or a direct bond;

wherein one or two hydrogen atoms in the bivalent radical —$C_sH_{2s}$— may, each independently from each other, be replaced by halo, hydroxy, mercapto, isothiocyanato, isocyanato, lower alkyloxy, lower alkylthio, $Ar^1$, $Ar^1O$—, $Ar^1S$—, $Ar^1SO_2$—, or $NR^3R^5$; and n is 0 or the integer 1 or 2;

r and s are, independently from each other, 0 or an integer of from 1 to 6 inclusive;

T is

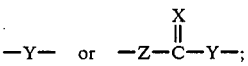

$T^1$ is

or a direct bond;

said Y being O, S, $NR^3$ or a direct bond;

X being O, S, CH—$NO_2$ or $NR^4$;

Z being O, S, $NR^5$ or a direct bond; and said $R^3$ being hydrogen, lower alkyl, ($Ar^2$)lower alkyl, 2-lower alkyloxy-1,2-dioxoethyl or a radical of formula —C(=X)—$R^6$, $R^6$ being hydrogen, lower alkyl, $Ar^2$, $Ar^2$-lower alkyl, lower alkyloxy, $Ar^2$-lower alkyloxy, mono- or di(lower alkyl)amino, $Ar^2$-amino, $Ar^2$-lower alkylamino or $Ar^2$-lower alkyl(lower alkyl)amino;

said $R^4$ being hydrogen, lower alkyl, cyano, nitro, $Ar^2$-sulfonyl, lower alkylsulfonyl, lower alkylcarbonyl or $Ar^2$-carbonyl; and said $R^5$ being hydrogen or lower alkyl;

wherein $L^1$ is a member selected from the group consisting of hydrogen; halo; hydroxy; lower alkyloxy; lower alkylthio; cyano; mercapto; isocyanato; isothiocyanato; $Ar^1$; $Ar^1$-carbonyl; $Ar^1$-sulfonyl; lower alkylsulfonyl; cycloalkyl being optionally substituted with up to two substituents each independently selected from the group consisting of lower alkyl, cyano and $Ar^2$; [10,11-dihydro-5H-dibenzo[a,d]cyclohepten-5-ylidene]-methyl; Het; and furan substituted with substituted lower alkyl; said substituted lower alkyl being lower alkyl substituted with a member selected from the group consisting of hydroxy, mercapto, lower alkyloxy, lower alkylthio, aminolower alkylthio, $Ar^2$-oxy and a radical of formula

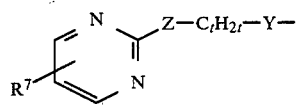

wherein: t is 0 or an integer of from 1 to 6 inclusive; and $R^7$ is hydrogen or lower alkyl;

provided that: when in said radical of formula (c) t is 0, then Z or Y is a direct bond; and where r is 0, $L^1$ may also be lower alkenyl, $Ar^1$-lower alkenyl or lower alkyl substituted with two lower alkyloxy radicals; and where r is 0 and T is $NR^3$, or T is $-N(R^5)-C(=X)-Y$ or $T^1$ is $-N(R^5)-C(=X)-$, $L^1$ may also be amino, lower alkylamino or $Ar^1$-amino; and where r is 0, and T is $-N(R^5)-C(=X)-Y$ or $T^1$ is $-N(R^5)-C(=X)-$, $L^1$ may also be nitro;

said Het being a five- or six-membered heterocyclic ring containing a number of heteroatoms which varies of from 1 to 4, said heteroatoms being selected from the group consisting of oxygen, sulfur and nitrogen, provided that no more than two oxygens or sulfurs are present, said five or six-membered ring being optionally condensed with a five- or six-membered carbocyclic or heterocyclic ring also containing a number of heteroatoms which varies from 1 to 4, the latter heteroatoms being selected from the group consisting of oxygen, sulfur and nitrogen, provided that no more than 2 oxygens or sulfurs are present, and wherein said Het being a bicyclic ring system may optionally be substituted with up to six substituents, or said Het being a monocyclic ring system may optionally be substituted with up to 3 substituents, said substituents of Het being selected from the group consisting of a bivalent radical of formula $=X$, said $=X$ independently having the same meaning of the previously defined X; halo; isocyanato; isothiocyanato; nitro, cyano, trifluoromethyl; a radical of formula R—Y— R is hydrogen, then Y is other than a direct bond, or (ii) when in the radical R—Z—C(=X)—Y— R is hydrogen and Y is $NR^3$, O or S, then Z is other than O or S provided that:

(i) when L is a radical of formula (b-1) wherein $L^1$ is hydrogen and wherein T is $-Z-C(=X)-Y-$ wherein Y is other then a direct bond and Z and X are each independently O or S, then r is not 0; or when L is a radical of formula (b-2) wherein $L^1$ is hydrogen and wherein $T^1$ is $-Z-C(=X)-$ wherein Z and X are each independently O or S, then r is not 0;

(ii) when L is a radical of formula (b-1) wherein $L^1$ is halo, hydroxy, lower alkyloxy, mercapto, lower alkylthio, isocyanato, isothiocyanato or Het connected to $C_rH_{2r}$ on a nitrogen atom, and wherein r is 0, then T is a direct bond or a radical $-C(=X)-Y-$; or when L is a radical of formula (b-2) wherein $L^1$ is halo, hydroxy, lower alkyloxy, mercapto, lower alkylthio, isocyanato, isothiocyanato or Het connected to $C_rH_{2r}$ on a nitrogen atom, and wherein r is 0, then $T^1$ is a radical $-C(=X)-$;

(iii) when L is a radical of formula (b-1) wherein T is Y, said Y being other than a direct bond, or wherein T is $-Z-C(=X)-Y-$, wherein Y is other than a direct bond, then s is not 0;

wherein $Ar^1$ is a member selected from the group consisting of phenyl, substituted phenyl, naphthalenyl, thienyl, halothienyl, lower alkylthienyl, pyridinyl, mono- and di(lower alkyloxy)pyridinyl, pyrrolyl, lower alkylpyrrolyl, furanyl, furanyl substituted with lower alkyl, pyrazinyl, thiazolyl, imidazolyl, lower alkylimidazolyl; said substituted phenyl, being phenyl substituted with up to 3 substituents each independently selected from the group consisting of halo, hydroxy, nitro, cyano, trifluoromethyl, lower alkyl, lower alkyloxy, lower alkylthio, mercapto, amino, mono- and di(lower alkyl)amino, lower alkylsulfonyl, lower alkylsulfonyllower alkyl, phenyllower alkylsulfonyl, phenylsulfonyllower alkyl, a radical of formula $R^8-C_pH_{2p}-Y-$, a radical of formula $R^9-Z-C(=X)-Y-$, and a radical of formula $R^{10}SO_2Y-$; wherein p is an integer of from 1 to 6 inclusive and $R^8$ is a member selected from the group consisting of amino, cyano, phenyl aminocarbonyl, mono- and di(lower alkyl)aminocarbonyl, lower alkyloxycarbonyl, phenyllower alkyloxycarbonyl, 4-morpholinylcarbonyl, 1-piperidinylcarbonyl, 1-pyrrolidinylcarbonyl, and lower alkenyl; wherein $R^9$ is member selected from the group consisting of hydrogen, lower alkyl and $Ar^2$; provided that, when $R^9$ is hydrogen and Y is other than a direct bond, then Z is not O or S; and wherein $R^{10}$ is lower alkyl or $Ar^2$;

wherein $Ar^2$ is a member selected from the group consisting of phenyl, substituted phenyl, thienyl and furanyl, said substituted phenyl being phenyl optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

2. A method according to claim 1, wherein Het is a member selected from the group consisting of:

(i) pyridinyl which is optionally substituted with one or two substituents each independently selected from the group consisting of halo, amino, mono- and dilower alkyl amino, $Ar^2$ lower alkylamino, nitro, cyano, aminocarbonyl, lower alkyl, lower alkyloxy, lower alkylthio, lower alkyloxycarbonyl, hydroxy, lower alkylcarbonyloxy, $Ar^2$-lower alkyl and carboxyl;

pyridinyloxide optionally substituted with nitro;

quinolinyl which is optionally substituted with lower alkyl;

pyrimidinyl which is optionally substituted with one or two substituents each independently selected from the group consisting of halo, amino, hydroxy, lower alkyl, lower alkyloxy, lower alkylthio and $(Ar^2)$-lower alkyl;

quinazolinyl which is optionally substituted with hydroxy or lower alkyl;

pyridazinyl which is optionally substituted with lower alkyl or halo;

quinoxalinyl which is optionally substituted with lower alkyl;

pyrazinyl which is optionally substituted with halo, amino or lower alkyl;

phthalazinyl which is optionally substituted with halo;

morfolinyl;

thiomorfolinyl;

piperidinyl;

2,3-dihydro-3-oxo-4H-benzoxazinyl and 2,3-dihydro-1,4-benzodioxinyl, both being optionally substituted with lower alkyl or halo;

dioxanyl being optionally substituted with lower alkyl;

2-oxo-2H-1-benzopyranyl and 4-oxo-4H-1-benzopyranyl both being optionally substituted with lower alkyl;

1,4-dihydro-2,4-dioxo-3(2H)-pyrimidinyl being optionally substituted with lower alkyl; and
4-oxo-2(1H)-pyrimidinyl;

(ii) 5,6-dihydro-4H-1,3-thiazin-2-yl, thiazolyl, 4,5-dihydrothiazolyl, oxazolyl, imidazolyl, tetrazolyl, 1,3,4-thiadiazolyl, benzimidazolyl, benzothiazolyl, benzoxazolyl, 4,5-dihydro-5-oxo-1H-tetrazolyl, 2-oxo-3-oxazolidinyl and indolyl whereby each of the Het-radicals of group (ii) may optionally be substituted where possible with up to two substituents selected from the group consisting of lower alkyl, $Ar^1$, $Ar^1$-lower alkyl, benzimidazolyllower alkyl, amino, (aminoiminomethyl)amino, mono- and di(lower alkyl)amino, $Ar^1$-amino, nitro, lower alkyloxycarbonyl and pyrimidinyl;

(iii) a radical of formula

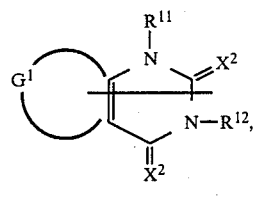
(e-1)

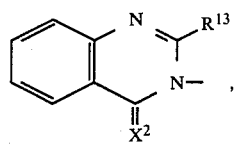
(e-2)

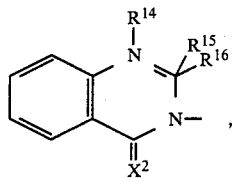
(e-3)

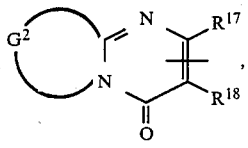
(e-4)

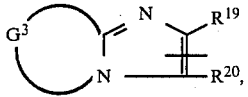
(e-5)

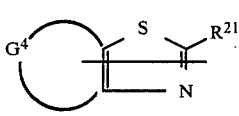
(e-6)

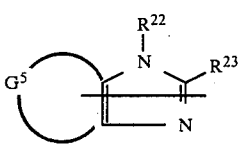
(e-7)

-continued

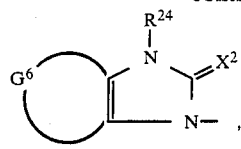
(e-8)

and

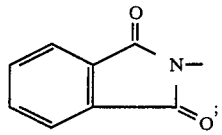
(e-9)

wherein each $X^2$ is independently O or S;
$R^{11}$, $R^{12}$, $R^{14}$, $R^{22}$ and $R^{24}$ are each independently hydrogen, lower alkyl, $Ar^2$-lower alkyl, hydroxylower alkyl or lower alkyloxycarbonyl; $R^{13}$, $R^{16}$, $R^{17}$, $R^{18}$, $R^{19}$, $R^{20}$, $R^{21}$ and $R^{23}$ are each independently hydrogen, lower alkyl, hydroxy, mercapto, lower alkyloxy, lower alkylthio, halo and (lower alkyloxycarbonyl)lower alkyl;

$G^1$ is —CH=CH—CH=CH—, —S—CH=CH— or —N=CH—NH—;

$G^2$ is —CH=CH—CH=CH—, —S—(CH$_2$)$_2$, —S—(CH$_2$)$_3$, —(CH$_2$)$_4$ or S—CH=CH—;

$G^3$ is —CH=CH—CH=CH—, —CH$_2$—NH—(CH$_2$)$_2$—, —S—CH=CH—, —N=CH—N=CH—CH=CH—, —CH=N—CH=CH—, —CH=CH—N=CH—, —CH=CH—CH=N—, —N=CH—N=CH— or —CH=N—CH=N—;

$G^4$ is —CH$_2$—NH—(CH$_2$)$_2$—, —N=CH—CH=CH— —CH=N—CH=CH—, —CH=CH—N=CH—, —CH=CH—CH=N—, —N=CH—N=CH— or —CH=N—CH=N—;

$G^5$ is —N=CH—CH=CH—, —CH=N—CH=CH—, —CH=CH—N=CH—, —CH=CH—CH=N—, —N=CH—N=CH— or —CH=N—CH=N—;

$G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in said radicals $G^1$, $G^2$, $G^3$, $G^4$, $G^5$ or $G^6$ or in the benzene part of the radicals of formula (e-2), (e-3) or (e-9) may be replaced by lower alkyl, lower alkylthio, lower alkyloxy or halo where said hydrogen atom is bonded on a carbon atom, or by lower alkyl, lower alkyloxycarbonyl, $Ar^2$-lower alkyl, where said hydrogen is bonded on a nitrogen atom; and wherein $R^{11}$, $R^{12}$, $R^{17}$, $R^{18}$, $R^{19}$, $R^{20}$, $R^{21}$, $R^{22}$ or $R^{23}$ is absent where the radical of formula (e-1), respectively (e-4), (e-5), (e-6) or (e-7) is connected to C$_s$H$_{2s}$ on the atom bearing $R^{11}$, $R^{12}$, $R^{17}$, $R^{18}$, $R^{19}$, $R^{20}$, $R^{21}$, $R^{22}$ or $R^{23}$.

3. A method according to claim 2, wherein r is 0 and $L^1$ is hydrogen, hydroxy, lower alkyloxy, lower alkylthio, mercapto, Het, $Ar^1$, cyanato, isothiocyanato, or isocyanato.

4. A method according to claim 3, wherein $R^1$ is lower alkyl substituted with one $Ar^1$ radical.

5. A method according to claim 4, wherein L is a radical of formula (b-1).

6. A method according to claim 1, wherein the compound is 1-[(4-fluorophenyl)methyl]-2-[[1-[2-(4-hydroxyphenyl)ethyl]-4-piperidinyl]methyl]-1H-benzimidazol-6-ol.

* * * * *